(12) United States Patent
Havenstrite et al.

(10) Patent No.: US 11,433,628 B2
(45) Date of Patent: Sep. 6, 2022

(54) CONTACT LENS WITH A HYDROPHILIC LAYER

(71) Applicant: Tangible Science, Inc., Redwood City, CA (US)

(72) Inventors: Karen L. Havenstrite, Saratoga, CA (US); Victor Wayne Mccray, San Jose, CA (US); Brandon McNary Felkins, Half Moon Bay, CA (US); Paul A. Cook, Palo Alto, CA (US)

(73) Assignee: Tangible Science, Inc., Redwood City, CA (US)

( * ) Notice: Subject to any disclaimer, the term of this patent is extended or adjusted under 35 U.S.C. 154(b) by 531 days.

(21) Appl. No.: 16/447,738

(22) Filed: Jun. 20, 2019

(65) Prior Publication Data
US 2019/0310495 A1    Oct. 10, 2019

Related U.S. Application Data

(60) Division of application No. 15/095,759, filed on Apr. 11, 2016, now Pat. No. 10,330,951, which is a
(Continued)

(51) Int. Cl.
*B29D 11/00* (2006.01)
*C09D 171/00* (2006.01)
(Continued)

(52) U.S. Cl.
CPC ............. *B29D 11/00* (2013.01); *A61B 5/01* (2013.01); *A61B 5/02* (2013.01); *A61B 5/14507* (2013.01);
(Continued)

(58) Field of Classification Search
CPC ............. B29D 11/00; B29D 11/00788; C09D 171/00; G02B 1/043; A61B 5/01; A61B 5/02; A61B 5/14507; A61B 5/14532
See application file for complete search history.

(56) References Cited

U.S. PATENT DOCUMENTS 2,976,576 A    3/1961    Wichterle et al.
3,408,429 A    10/1968   Otto
(Continued)

FOREIGN PATENT DOCUMENTS

CN    1180416 A    4/1998
CN    1233191 A    10/1999
(Continued)

OTHER PUBLICATIONS

Bearinger et al.; P(Aam-co-EG) interpenetrating polymer networks grafted to oxide surfaces: surface characterization, protein adsorption, and cell detachment studies; Langmuir; 13(19); pp. 5175-5183; Sep. 17, 1997.
(Continued)

*Primary Examiner* — Mathieu D Vargot
(74) *Attorney, Agent, or Firm* — Shay Glenn LLP

(57) ABSTRACT

Embodiments of the technology relate to a contact lens having a core that is coated by a hydrogel layer, and to methods of making such a lens. The coated lens can include a rigid gas permeable contact lens. The coated lens can also include a hybrid silicone and rigid gas permeable contact lens. In one aspect, embodiments provide for a coated contact lens comprising a lens core with a water equilibrium constant of less than about 2% comprising an outer surface; and a hydrogel layer covalently attached to at least a portion of the outer surface, the hydrogel layer adapted to contact an ophthalmic surface, wherein the hydrogel layer comprises a hydrophilic polymer population of one or more species.

20 Claims, 50 Drawing Sheets

Related U.S. Application Data continuation of application No. 14/660,728, filed on Mar. 17, 2015, now Pat. No. 9,310,627, which is a continuation of application No. PCT/US2014/065588, filed on Nov. 14, 2014.

(60) Provisional application No. 61/905,092, filed on Nov. 15, 2013.

(51) Int. Cl.
  *G02B 1/04* (2006.01)
  *A61B 5/01* (2006.01)
  *A61B 5/02* (2006.01)
  *A61B 5/145* (2006.01)
  *G02C 7/04* (2006.01)

(52) U.S. Cl.
  CPC .... *A61B 5/14532* (2013.01); *B29D 11/00788* (2013.01); *C09D 171/00* (2013.01); *G02B 1/043* (2013.01); *G02C 7/04* (2013.01); *G02C 7/049* (2013.01); *G02C 2202/16* (2013.01)

(56) References Cited

U.S. PATENT DOCUMENTS

| | | |
|---|---|---|
| 4,136,250 A | 1/1979 | Mueller et al. |
| 4,143,949 A | 3/1979 | Chen |
| 4,153,641 A | 5/1979 | Deichert et al. |
| 4,182,822 A | 1/1980 | Chang |
| 4,189,546 A | 2/1980 | Deichert et al. |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | Leboeuf |
| 4,276,402 A | 6/1981 | Chromecek et al. |
| 4,327,203 A | 4/1982 | Deichert et al. |
| 4,338,419 A | 7/1982 | Korb et al. |
| 4,341,889 A | 7/1982 | Deichert et al. |
| 4,343,927 A | 8/1982 | Chang |
| 4,347,198 A | 8/1982 | Ohkada et al. |
| 4,355,147 A | 10/1982 | Deichert et al. |
| 4,444,711 A | 4/1984 | Schad |
| 4,460,534 A | 7/1984 | Boehm et al. |
| 4,468,229 A | 8/1984 | Su |
| 4,486,577 A | 12/1984 | Mueller et al. |
| 4,543,398 A | 9/1985 | Bany et al. |
| 4,553,975 A | 11/1985 | Su |
| 4,605,712 A | 8/1986 | Mueller et al. |
| 4,661,575 A | 4/1987 | Tom |
| 4,684,538 A | 8/1987 | Klemarczyk |
| 4,703,097 A | 10/1987 | Wingler et al. |
| 4,833,218 A | 5/1989 | Lee |
| 4,837,289 A | 6/1989 | Mueller et al. |
| 4,929,250 A | 5/1990 | Hung et al. |
| 4,954,586 A | 9/1990 | Toyoshima et al. |
| 4,954,587 A | 9/1990 | Mueller |
| 5,010,141 A | 4/1991 | Mueller |
| 5,034,461 A | 7/1991 | Lai et al. |
| 5,039,761 A | 8/1991 | Ono et al. |
| 5,070,170 A | 12/1991 | Robertson et al. |
| 5,098,445 A | 3/1992 | Hung et al. |
| 5,135,297 A | 8/1992 | Valint |
| 5,135,965 A | 8/1992 | Tahan |
| 5,196,458 A | 3/1993 | Nunez et al. |
| 5,219,965 A | 6/1993 | Valint et al. |
| 5,260,000 A | 11/1993 | Nandu et al. |
| 5,326,584 A | 7/1994 | Kamel et al. |
| 5,346,946 A | 9/1994 | Yokoyama et al. |
| 5,352,714 A | 10/1994 | Lai et al. |
| 5,358,995 A | 10/1994 | Lai et al. |
| 5,409,731 A | 4/1995 | Nakagawa et al. |
| 5,416,132 A | 5/1995 | Yokoyama et al. |
| 5,446,090 A | 8/1995 | Harris |
| 5,451,617 A | 9/1995 | Lai et al. |
| 5,486,579 A | 1/1996 | Lai et al. |
| 5,508,317 A | 4/1996 | Muller |
| 5,583,463 A | 12/1996 | Merritt |
| 5,645,882 A | 7/1997 | Llanos |
| 5,674,942 A | 10/1997 | Hill et al. |
| 5,681,871 A | 10/1997 | Molock et al. |
| 5,760,100 A | 6/1998 | Nicolson et al. |
| 5,805,264 A | 9/1998 | Janssen et al. |
| 5,843,346 A | 12/1998 | Morrill |
| 5,874,500 A | 2/1999 | Rhee et al. |
| 5,894,002 A | 4/1999 | Boneberger et al. |
| 5,962,548 A | 10/1999 | Vanderlaan et al. |
| 5,981,675 A | 11/1999 | Valint et al. |
| 6,019,472 A | 2/2000 | Koester et al. |
| 6,022,553 A | 2/2000 | Anders et al. |
| 6,039,913 A | 3/2000 | Hirt et al. |
| 6,201,065 B1 | 3/2001 | Pathak et al. |
| 6,218,508 B1 | 4/2001 | Kragh et al. |
| 6,309,660 B1 | 10/2001 | Hsu et al. |
| 6,340,465 B1 | 1/2002 | Hsu et al. |
| 6,406,739 B1 | 6/2002 | LeBoeuf et al. |
| 6,428,839 B1 | 8/2002 | Künzler et al. |
| 6,440,571 B1 | 8/2002 | Valint et al. |
| 6,447,920 B1 | 9/2002 | Chadbrecek et al. |
| 6,451,871 B1 | 9/2002 | Winterton et al. |
| 6,458,889 B1 | 10/2002 | Trollsas et al. |
| 6,468,667 B1 | 10/2002 | Chabrecek et al. |
| 6,478,423 B1 | 11/2002 | Turner et al. |
| 6,500,481 B1 | 12/2002 | Vanderlaan et al. |
| 6,623,747 B1 | 9/2003 | Chatelier et al. |
| 6,624,245 B2 | 9/2003 | Wallace et al. |
| 6,627,124 B1 | 9/2003 | Herbrechtsmeier et al. |
| 6,630,243 B2 | 10/2003 | Valint et al. |
| 6,638,563 B2 | 10/2003 | McGee et al. |
| 6,719,929 B2 | 4/2004 | Winterton et al. |
| 6,723,815 B2 | 4/2004 | Callaghan et al. |
| 6,740,116 B2 | 5/2004 | Morcher |
| 6,759,388 B1 | 7/2004 | Marchant et al. |
| 6,762,264 B2 | 7/2004 | Künzler et al. |
| 6,793,973 B2 | 9/2004 | Winterton et al. |
| 6,800,225 B1 | 10/2004 | Hagmann et al. |
| 6,811,259 B2 | 11/2004 | Tucker |
| 6,811,805 B2 | 11/2004 | Gilliard et al. |
| 6,815,074 B2 | 11/2004 | Aguado et al. |
| 6,827,966 B2 | 12/2004 | Qiu et al. |
| 6,852,353 B2 | 2/2005 | Qiu et al. |
| 6,858,248 B2 | 2/2005 | Qiu et al. |
| 6,896,926 B2 | 5/2005 | Qiu et al. |
| 6,940,580 B2 | 9/2005 | Winterton et al. |
| 7,037,517 B2 | 5/2006 | Kataoka et al. |
| 7,053,150 B2 | 5/2006 | Kozlowski et al. |
| 7,091,283 B2 | 8/2006 | Müller et al. |
| 7,132,475 B2 | 11/2006 | Hubbell et al. |
| 7,247,387 B1 | 7/2007 | Huang |
| 7,251,519 B2 | 7/2007 | Axelsson et al. |
| 7,276,474 B2 | 10/2007 | Marchant et al. |
| 7,384,590 B2 | 6/2008 | Kelly et al. |
| 7,402,318 B2 | 7/2008 | Morris et al. |
| 7,507,469 B2 | 3/2009 | Mao et al. |
| 7,642,332 B2 | 1/2010 | Kennedy et al. |
| 7,674,478 B2 | 3/2010 | Kataoka et al. |
| 7,695,775 B2 | 4/2010 | Kobrin et al. |
| 7,744,912 B1 | 6/2010 | Hubbell et al. |
| 7,833,715 B1 | 11/2010 | Schweitzer et al. |
| 7,847,025 B2 | 12/2010 | Liu et al. |
| 7,857,447 B2 | 12/2010 | Myung et al. |
| 7,857,849 B2 | 12/2010 | Myung et al. |
| 7,858,000 B2 | 12/2010 | Winterton |
| 7,942,929 B2 | 5/2011 | Linhardt et al. |
| 7,955,704 B2 | 6/2011 | Lowery et al. |
| 8,071,121 B2 | 12/2011 | Chauhan et al. |
| 8,083,348 B2 | 12/2011 | Linhardt et al. |
| 8,133,580 B2 | 3/2012 | Dias et al. |
| 8,163,302 B2 | 4/2012 | Marchant et al. |
| 8,178,602 B2 | 5/2012 | Mao et al. |
| 8,309,117 B2 | 11/2012 | Rubner et al. |
| 8,357,760 B2 | 1/2013 | Qiu |
| 8,409,599 B2 | 4/2013 | Wu et al. |
| 8,425,926 B2 | 4/2013 | Qiu et al. |
| 8,480,227 B2 | 7/2013 | Qiu et al. |

(56) References Cited

U.S. PATENT DOCUMENTS

| | | |
|---|---|---|
| 8,790,678 B2 | 7/2014 | Elbert et al. |
| 8,871,016 B2 | 10/2014 | Trexler et al. |
| 8,871,869 B2 | 10/2014 | Dias et al. |
| 8,906,284 B2 | 12/2014 | Crosby et al. |
| 9,244,195 B2 | 1/2016 | Bauman et al. |
| 9,310,627 B2 | 4/2016 | Havenstrite et al. |
| 9,358,735 B2 | 6/2016 | Bothe et al. |
| 9,395,468 B2 | 7/2016 | Havenstrite et al. |
| 9,395,627 B2 | 7/2016 | Liu et al. |
| 10,330,951 B2 | 6/2019 | Havenstrite et al. |
| 11,181,754 B2 | 11/2021 | Havenstrite et al. |
| 2001/0044021 A1 | 11/2001 | Ogawa et al. |
| 2002/0006493 A1 | 1/2002 | Chabrecek et al. |
| 2002/0057417 A1 | 5/2002 | Galin |
| 2002/0086160 A1 | 7/2002 | Qiu et al. |
| 2002/0155222 A1 | 10/2002 | Caron |
| 2003/0008063 A1 | 1/2003 | Chabrecek et al. |
| 2003/0087099 A1 | 5/2003 | Merill et al. |
| 2004/0067365 A1 | 4/2004 | Qiu |
| 2004/0086479 A1 | 5/2004 | Grinstaff et al. |
| 2004/0108607 A1 | 6/2004 | Winterton et al. |
| 2004/0116564 A1 | 6/2004 | Devlin et al. |
| 2004/0135967 A1 | 7/2004 | Carney et al. |
| 2004/0142016 A1 | 7/2004 | Luthra et al. |
| 2004/0181172 A1 | 9/2004 | Carney et al. |
| 2005/0008676 A1 | 1/2005 | Qiu et al. |
| 2005/0031793 A1 | 2/2005 | Moeller et al. |
| 2005/0053642 A1 | 3/2005 | Ulbricht et al. |
| 2005/0129731 A1 | 6/2005 | Horres et al. |
| 2006/0063852 A1 | 3/2006 | Iwata et al. |
| 2006/0275337 A1 | 12/2006 | Cohen et al. |
| 2006/0290882 A1 | 12/2006 | Meyers et al. |
| 2006/0292701 A1 | 12/2006 | Huang et al. |
| 2007/0001155 A1 | 1/2007 | Walters et al. |
| 2007/0031498 A1 | 2/2007 | Zong et al. |
| 2007/0082019 A1 | 4/2007 | Huang et al. |
| 2007/0087113 A1 | 4/2007 | Uilk et al. |
| 2007/0116741 A1 | 5/2007 | Valint et al. |
| 2007/0122540 A1 | 5/2007 | Salamone et al. |
| 2007/0129792 A1 | 6/2007 | Picart et al. |
| 2007/0197681 A1 | 8/2007 | Lowery et al. |
| 2007/0229758 A1 | 10/2007 | Matsuzawa |
| 2008/0002146 A1 | 1/2008 | Stachowski et al. |
| 2008/0015315 A1 | 1/2008 | Chang et al. |
| 2008/0038221 A1 | 2/2008 | Suda et al. |
| 2008/0076851 A1 | 3/2008 | Goldberg et al. |
| 2008/0143003 A1 | 6/2008 | Phelan |
| 2008/0143958 A1 | 6/2008 | Medina et al. |
| 2008/0152685 A1 | 6/2008 | Blackwell et al. |
| 2008/0152800 A1 | 6/2008 | Bothe et al. |
| 2008/0181931 A1 | 7/2008 | Qiu et al. |
| 2008/0203592 A1 | 8/2008 | Qiu et al. |
| 2008/0226922 A1 | 9/2008 | Ferreiro et al. |
| 2008/0231798 A1 | 9/2008 | Zhou et al. |
| 2008/0234457 A1 | 9/2008 | Zhou et al. |
| 2008/0255305 A1 | 10/2008 | Brook et al. |
| 2009/0060981 A1 | 3/2009 | Chauhan |
| 2009/0081275 A1 | 3/2009 | Rolfes et al. |
| 2009/0123519 A1 | 5/2009 | Rolfes et al. |
| 2009/0155595 A1 | 6/2009 | Lee |
| 2009/0280157 A1 | 11/2009 | Mass et al. |
| 2010/0013114 A1 | 1/2010 | Bowers et al. |
| 2010/0069522 A1 | 3/2010 | Linhardt et al. |
| 2010/0099852 A1 | 4/2010 | Cassingham et al. |
| 2010/0114042 A1 | 5/2010 | Dias et al. |
| 2010/0120938 A1 | 5/2010 | Phelan et al. |
| 2010/0140114 A1 | 6/2010 | Pruitt et al. |
| 2010/0149482 A1 | 6/2010 | Ammon et al. |
| 2010/0152708 A1 | 6/2010 | Li et al. |
| 2010/0198168 A1 | 8/2010 | Rooijmans |
| 2010/0226963 A1 | 9/2010 | Cooper et al. |
| 2010/0239637 A1 | 9/2010 | Ciolino et al. |
| 2010/0249273 A1 | 9/2010 | Scales et al. |
| 2010/0298446 A1 | 11/2010 | Chang et al. |
| 2011/0133350 A1 | 6/2011 | Qiu et al. |
| 2011/0134387 A1 | 6/2011 | Samuel et al. |
| 2011/0177150 A1 | 7/2011 | Pathak et al. |
| 2011/0189493 A1 | 8/2011 | Ott et al. |
| 2011/0293669 A1 | 12/2011 | Bennett et al. |
| 2011/0293687 A1 | 12/2011 | Bennett et al. |
| 2011/0293688 A1 | 12/2011 | Bennett et al. |
| 2011/0293692 A1 | 12/2011 | Bennett et al. |
| 2011/0293699 A1 | 12/2011 | Bennett et al. |
| 2012/0023869 A1 | 2/2012 | Samuel et al. |
| 2012/0026457 A1 | 2/2012 | Qiu et al. |
| 2012/0038888 A1 | 2/2012 | Gu et al. |
| 2012/0049689 A1 | 3/2012 | Bennett et al. |
| 2012/0116019 A1 | 5/2012 | Suzuki et al. |
| 2012/0137635 A1 | 6/2012 | Qiu et al. |
| 2012/0139137 A1 | 6/2012 | Qiu |
| 2012/0147323 A1 | 6/2012 | Domschke |
| 2013/0090344 A1 | 4/2013 | Thakur et al. |
| 2013/0095235 A1 | 4/2013 | Bothe et al. |
| 2013/0118127 A1 | 5/2013 | Kolluru et al. |
| 2013/0162943 A1 | 6/2013 | Goodenough et al. |
| 2013/0176529 A1 | 7/2013 | Li et al. |
| 2013/0188124 A1 | 7/2013 | Li et al. |
| 2014/0155313 A1 | 6/2014 | Eggink et al. |
| 2016/0161639 A1 | 6/2016 | Scales et al. |
| 2016/0216534 A1 | 7/2016 | Legerton et al. |
| 2016/0320635 A1 | 11/2016 | Havenstrite et al. |
| 2017/0160432 A1 | 6/2017 | Havenstrite et al. |
| 2017/0242269 A1 | 8/2017 | Havenstrite et al. |
| 2017/0360994 A1 | 12/2017 | Havenstrite et al. |
| 2020/0129671 A1 | 4/2020 | Havenstrite et al. |
| 2022/0075098 A1 | 3/2022 | Mabry et al. |
| 2022/0075208 A1 | 3/2022 | Havenstrite et al. |

FOREIGN PATENT DOCUMENTS

| | | |
|---|---|---|
| CN | 1543362 A | 11/2004 |
| CN | 1602228 A | 3/2005 |
| CN | 1961223 A | 5/2007 |
| CN | 101096451 A | 1/2008 |
| CN | 101688042 A | 3/2010 |
| CN | 101726864 A | 6/2010 |
| CN | 102323629 A | 1/2012 |
| CN | 103254436 A | 8/2013 |
| CN | 103547585 A | 1/2014 |
| EP | 0807140 A1 | 11/1997 |
| EP | 808222 B1 | 5/1999 |
| EP | 1251973 A1 | 10/2002 |
| EP | 1319037 A1 | 6/2003 |
| EP | 0906122 B1 | 9/2003 |
| EP | 1412404 A1 | 4/2004 |
| EP | 1268621 B1 | 11/2005 |
| EP | 0876165 B1 | 6/2006 |
| EP | 1744836 A2 | 1/2007 |
| EP | 1427532 B1 | 2/2007 |
| EP | 0918550 B1 | 4/2007 |
| EP | 2061526 A2 | 5/2009 |
| EP | 1261557 B1 | 11/2009 |
| EP | 1458797 B1 | 12/2009 |
| EP | 2187980 A1 | 5/2010 |
| EP | 2219865 A2 | 8/2010 |
| EP | 2389895 A2 | 11/2011 |
| EP | 2443482 A2 | 4/2012 |
| EP | 1355965 B1 | 9/2012 |
| EP | 1932874 B1 | 2/2013 |
| EP | 2461767 B1 | 5/2013 |
| EP | 2455104 B1 | 7/2013 |
| EP | 2624871 A2 | 8/2013 |
| JP | H09-507784 A | 8/1997 |
| JP | 2000512677 A | 9/2000 |
| JP | 2000351862 A | 12/2000 |
| JP | 2001131271 A | 5/2001 |
| JP | 2001518528 A | 10/2001 |
| JP | 2003512513 A | 4/2003 |
| JP | 2003527890 A | 9/2003 |
| JP | 2005520703 A | 7/2005 |
| JP | 2006508720 A | 3/2006 |
| JP | 2008511870 A | 4/2006 |
| JP | 201 3533518 A | 8/2013 |
| WO | WO93/00391 A1 | 1/1993 |

(56) References Cited

FOREIGN PATENT DOCUMENTS

| WO | WO98/28026 A1 | 7/1998 |
|---|---|---|
| WO | WO99/55742 A1 | 11/1999 |
| WO | WO01/05578 A1 | 1/2001 |
| WO | WO01/32230 A2 | 5/2001 |
| WO | WO01/44861 A1 | 6/2001 |
| WO | WO01/57118 A2 | 8/2001 |
| WO | WO01/92924 A1 | 12/2001 |
| WO | WO02/16974 A2 | 2/2002 |
| WO | WO02/096477 A2 | 12/2002 |
| WO | WO02/097481 A1 | 12/2002 |
| WO | WO03/041754 A1 | 5/2003 |
| WO | WO03/057270 A1 | 7/2003 |
| WO | WO03/075888 A2 | 9/2003 |
| WO | WO2004/024203 A1 | 3/2004 |
| WO | WO2004/025332 A1 | 3/2004 |
| WO | WO2004/056403 A2 | 7/2004 |
| WO | WO2004/056404 A2 | 7/2004 |
| WO | WO2004/080297 A1 | 9/2004 |
| WO | WO2005/014074 A1 | 2/2005 |
| WO | WO2005/035607 A1 | 4/2005 |
| WO | WO2007/002671 A1 | 1/2007 |
| WO | WO2007/146137 A2 | 12/2007 |
| WO | WO2008/024071 A1 | 2/2008 |
| WO | WO2008/079809 A2 | 7/2008 |
| WO | WO2008/094876 A1 | 8/2008 |
| WO | WO2008/101417 A1 | 8/2008 |
| WO | WO2008/130604 A2 | 10/2008 |
| WO | WO2008/156604 A1 | 12/2008 |
| WO | WO2009/042191 A1 | 4/2009 |
| WO | WO2009/055082 A2 | 4/2009 |
| WO | WO2009/094368 A1 | 7/2009 |
| WO | WO2010/003078 A2 | 1/2010 |
| WO | WO2010/011492 A1 | 1/2010 |
| WO | WO2010/018293 A1 | 2/2010 |
| WO | WO2010/056686 A1 | 5/2010 |
| WO | WO2010/065686 A1 | 6/2010 |
| WO | WO2010/065960 A2 | 6/2010 |
| WO | WO2010/103089 A1 | 9/2010 |
| WO | WO2011/007454 A1 | 1/2011 |
| WO | WO2011/056761 A1 | 5/2011 |
| WO | WO2011/071790 A1 | 6/2011 |
| WO | WO2011/071791 A1 | 6/2011 |
| WO | WO2012/035598 A1 | 3/2012 |
| WO | WO2012/149256 A2 | 4/2012 |
| WO | WO2012/055884 A1 | 5/2012 |
| WO | WO2012/074859 A1 | 6/2012 |
| WO | WO2012/082704 A1 | 6/2012 |
| WO | WO2012/153072 A1 | 11/2012 |
| WO | WO2013/055746 A1 | 4/2013 |
| WO | WO2013/074535 A1 | 5/2013 |
| WO | WO2013/166358 A1 | 11/2013 |
| WO | WO2015/031196 A1 | 3/2015 |
| WO | WO2016/026884 A1 | 2/2016 |

OTHER PUBLICATIONS

Bundgaard et al.; N-Sulfonyl imidates as a novel prodrug form for an ester function or a sulfonamide group; J Med Chem; 31(11); pp. 2066-2069; Nov. 1988.
Chang et al.; U.S. Appl. No. 61/180,453 entitled "Actinically-crosslinkable siloxane-containing copolymers," filed May 22, 2009.
Dilsiz et al.; Plasma Polymerization of Selected Organic Compounds; Polymer; 37(2); pp. 333-342; Jan. 1996.
Ghormely; The advent contact lens-clinical viewpoints; 3 pages; retrieved from http://www.sciencedirect.com/science/article/pii/0892896789900321/pdf?md5=5ff798a43537ff29c508eb02d36dd&pid=1-2.0-0892896789900321-main.pdf on May 23, 2017.
Greene et al.; Protective Groups in Organic Synthesis; 2nd Ed.; John Wiley & Sons; New York, NY; pp. 178-210; Oct. 1991.
Hermanson; Chapter 3: The Reactions of Bioconjugation; in Bioconjugate Techniques; 3rd Ed.; Academic Press, San Diego, CA; pp. 229-258; Sep. 2013.

Kayaman et al.; Phase transition of polyacrylamide gels in PEG solutions; Polymer Gels and Networks; 5(2); pp. 167-184; Apr. 1997.
Keana et al.; New Reagents for Photoaffinity Labeling: Synthesis and Photolysis of Functionalized Perfluorophenyl Azides; J. Org. Chem.; 55(11); pp. 3640-3647; May 1990.
The Merck Index, An Encyclopedia of chemicals, drugs, and biologicals; Ed. Susan Budavari; 12th Edition; "7519 Phosphorycholine"; p. 1267; (year of pub. sufficiently earlier than effective US filing date and any foreign priority date) 1996.
Pantar; The polymerization of acrylamide in the presence of poly (ethylene glycol) II; European Polymer Journal; 22(11); pp. 939-942; Jan. 1986.
Park et al.; Surface modifications of poly(ethylene terephthalate) angioplasty balloons with a hydrophilic poly (acrylamide-co-ethylene glycol) interpenetrating polymer network coating; J. Biomed. Mater. Res.; 53(5); pp. 568-576; Sep. 1,2000.
Petracek et al.; Hydroxymethylketones as pro-drugs; Annals NY Acad Sci; 507; pp. 353-354; Dec. 1987.
Pissis; Hydration studies in polymer hydrogels; Journal of Polymer Science Part B: Polymer Physics; 51(3); pp. 159-175; Feb. 2013.
Szczotka-Flynn; Introducing the latest silicone hydrogel lens; Contact Lens Spectrum; 20(8); 2 pages; retrieved from the internet (https://www.clspectrum.com/issues/2005/august-2005/contact-lens-materials); Aug. 1, 2005.
Vladkova; Surface engineered polymeric biomaterials with improved biocontact properties; International Journal of Polymer Science; Article ID 296094 doi: 10.1155/2010/296094; 22 pages; (year of pub. sufficiently earlier than effective US filing date and any foreign priority date) 2010.
Yamada et al.;Selective modification of aspartic acid-101 in lysozyme by carbodiimide reaction; Biochemistry; 20(17); pp. 4836-4842; Aug. 1981.
Yasuda; Glow discharge polymerization; Journal of Polymer Science: Macromolecular Reviews; 16(1); pp. 199-293; 1981.
Guruvenket et al.; Plasma surface modification of polystyrene and polyethylene; Applied Surface Science; 236(1-4); pp. 278-284; Sep. 15, 2004.
Hall et al.; Activated gas plasma surface treatment of polymers for treatment of polymers for adhesive bonding; Journal of Applied Polymer Science; 13(10); pp. 2085-2096; Oct. 1969.
Read et al.; Dynamic contact angle analysis of silicone hydrogel contact lenses; Journal of Biomaterials Applications; 26(1); pp. 85-99; Jul. 2011.
Chattopadhyay et al., Functional polymers bearing reactive azetidinium groups, synthesis and characterization; Macromoleular Chemistry and Physics; 213(5); pp. 500-512; Mar. 2012.
Polymer Properties Database; Polyacrylamides; 2 pages; retrieved from the internet (https://polymerdatabase.com/polymer%20classes/Polyacrylamide%20type.html); on Jul. 9, 2021.
Wilson; Resolution and optical sectioning in the confocal microscope; Journal of Microscopy; 244(2); pp. 113-121; Nov. 2011.
Yongruida; Polyacrylamide (PAM) (Product Description); 5 pages; retrieved from the internet (https://www.yrdcarbon.com/products/chemical/polyacrylamide.html) on Jul. 29, 2021.
Hoepfner et al. (Editors); Tetronic; Fiedler Encyclopedia of Excipients for Pharmaceuticals, Cosmetics and Related Areas 5th ed.; Der Pharmazeutische vol. 9; vol. 2 (L-Z); p. 1586; 2002 (the year of publication is sufficiently earlier than the effective U.S. filing date and any foreign priority date so that the particular month of publication is not in issue).
Hoeppner et al. (Editors); Pluronics; Fiedler Encyclopedia of Excipients for Pharmaceuticals, Cosmetics and Related Areas 5th ed.; Der Pharmazeutische vol. 9, vol. 2 (L-Z); pp. 1224-1227; 2002 (the year of publication is sufficiently earlier than the effective U.S. filing date and any foreign priority date so that the particular month of publication is not in issue).
Herman; Fluorescence microscopy Second ed.; Bios Scientific Publishers; Chapter Two: Fluorescence microscopy; pp. 15-19; 1998 the year of publication is sufficiently earlier than the effective U.S. filing date and any foreign priority date so that the particular month of publication is not in issue).

(56) References Cited

OTHER PUBLICATIONS

Justynska et al.; U.S. Appl. No. 61/180,449 entitled "Actinically-crosslinkable siloxane-containing copolymers," filed May 22, 2009.

Nucleophile
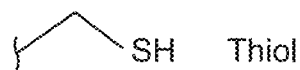   Thiol
Electron pair acceptor
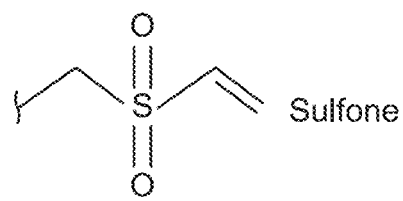  Sulfone
FIG. 4A
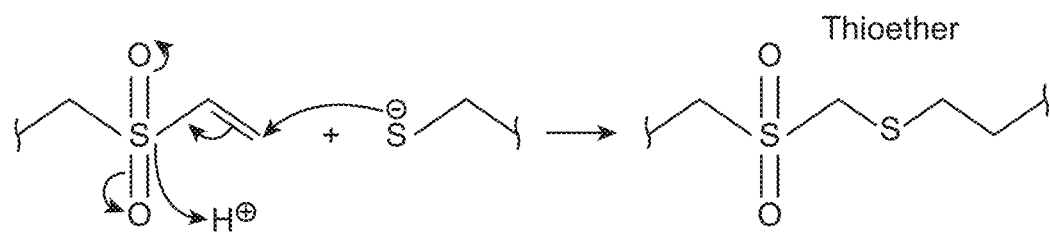
FIG. 4B

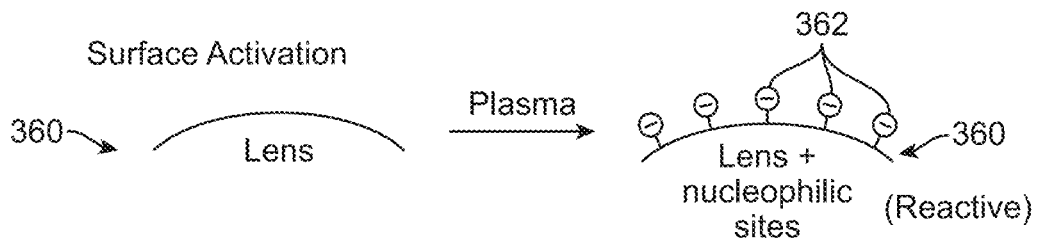
FIG. 9A
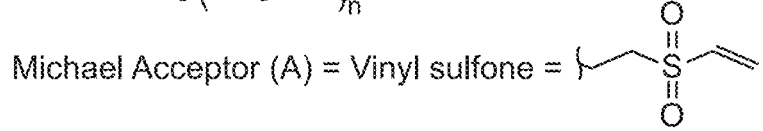
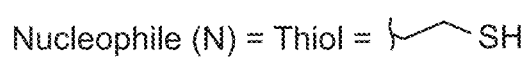
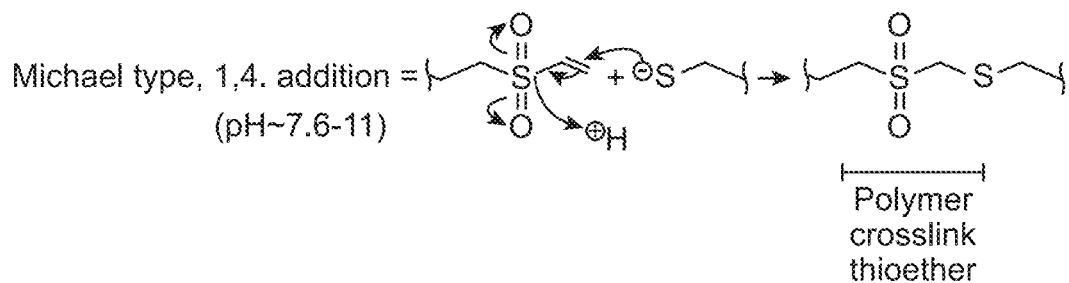
FIG. 9B
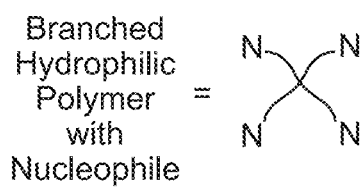
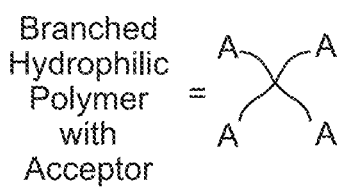
FIG. 9C

Figure 13A

| Example No. | Lot No. | Date | Advancing Angle |
|---|---|---|---|
| 10 | 1 | 5/12/2012 | |
| 10 | 2 | 5/12/2012 | |
| 10 | 3 | 5/16/2012 | |
| 10 | 4 | 5/23/2012 | |
| 10 | 5 | 5/25/2012 | |
| 10 | 6 | 5/28/2012 | |
| 10 | 7 | 6/1/2012 | |
| 10 | 8 | 6/6/2012 | |
| 12 | 9 | 6/6/2012 | |
| 12 | 10 | 6/6/21012 | |
| 12 | 11 | 6/8/2012 | |
| 12 | 12 | 6/8/2012 | |
| 14 | 13 | 6/8/2012 | |
| 12 | 14 | 7/6/2012 | |
| 65 | 15 | | |
| 66 | 17 | 8/20/2012 | |
| 65 | 19 | 8/24/2012 | |
| 64 | 21 | 9/14/2012 | |
| 64 | 22 | 9/14/2012 | |
| 64 | 23 | 9/14/2012 | |
| 63 | 24 | 9/19/2012 | |
| 63 | 25 | 9/19/2012 | |
| 67 | 26 | 9/19/2012 | |
| 67 | 27 | 9/20/2012 | |
| 67 | 28 | 9/20/2012 | |
| 67 | 29 | 9/20/2012 | |
| 67 | 30 | 9/20/2012 | |
| 62 | 31 | 10/3/2012 | |
| 62 | 32 | 10/3/2012 | |
| 62 | 33 | 10/3/2012 | |
| 62 | 34 | 10/3/2012 | |
| 67 | 35 | 10/3/2012 | |
| 67 | 36 | 10/3/2012 | |
| 67 | 37 | 10/3/2012 | |
| 67 | 38 | 10/3/2012 | |
| 57 | 39 | 10/10/2012 | 58.30 |
| | 39 | | 58.10 |
| | 39 | | 58.50 |
| 57 | 40 | 10/10/2012 | 52.50 |
| | 40 | | 52.60 |
| | 40 | | 52.40 |
| 57 | 41 | 10/10/2012 | 67.40 |
| | 41 | | 69.10 |
| | 41 | | 65.80 |
| 57 | 42 | 10/10/2012 | 41.70 |
| | 42 | | 43.02 |

| Example No. | Lot No. | Date | Advancing Angle |
|---|---|---|---|
|  | 42 |  | 40.38 |
| 57 | 43 | 10/10/2012 | 43.38 |
|  | 43 |  | 43.67 |
|  | 43 |  | 45.14 |
|  | 43 |  | 41.34 |
| 57 | 44 | 10/10/2012 | 47.60 |
|  | 44 |  | 50.22 |
|  | 44 |  | 48.40 |
|  | 44 |  | 44.18 |
| 59 | 45 | 10/11/2012 |  |
| 59 | 46 | 10/11/2012 | 79.75 |
|  | 46 |  | 74.83 |
|  | 46 |  | 73.14 |
|  | 46 |  | 86.09 |
|  | 46 |  | 84.94 |
| 57 | 47 | 10/11/2012 | 67.86 |
|  | 47 |  | 85.56 |
|  | 47 |  | 85.98 |
|  | 47 |  | 55.19 |
|  | 47 |  | 55.76 |
|  | 47 |  | 56.82 |
| 60 | 48 | 10/15/2012 | 53.20 |
|  | 48 |  | 57.20 |
|  | 48 |  | 60.50 |
|  | 48 |  | 44.60 |
|  | 48 |  | 43.20 |
|  | 48 |  | 58.40 |
|  | 48 |  | 55.60 |
| 60 | 49 | 10/15/2012 | 59.00 |
|  | 49 |  | 49.70 |
|  | 49 |  | 50.30 |
|  | 49 |  | 55.70 |
|  | 49 |  | 58.60 |
|  | 49 |  | 57.40 |
|  | 49 |  | 82.20 |
| 58 | 50 | 10/16/2012 | 63.60 |
|  | 50 |  | 87.90 |
|  | 50 |  | 83.60 |
|  | 50 |  | 47.60 |
|  | 50 |  | 48.90 |
|  | 50 |  | 55.90 |
|  | 50 |  | 57.80 |
| 68 | 51 | 10/16/2012 | 55.80 |
|  | 51 |  | 52.60 |
|  | 51 |  | 53.10 |
|  | 51 |  | 55.40 |

Figure 13B

| Example No. | Lot No. | Date | Advancing Angle |
|---|---|---|---|
| | 51 | | 58.20 |
| | 51 | | 57.20 |
| | 51 | | 58.40 |
| 68 | 52 | 10/16/2012 | 79.90 |
| | 52 | | 88.30 |
| | 52 | | 54.00 |
| | 52 | | 65.80 |
| | 52 | | 98.20 |
| | 52 | | 87.00 |
| | 52 | | 86.40 |
| 68 | 53 | 10/16/2012 | |
| 57 | 54 | 10/16/2012 | |
| 32 | 55 | 10/16/2012 | |
| 57 | 56 | 10/16/2012 | |
| 18 | 57 | 10/16/2012 | 43.80 |
| | 57 | | 40.30 |
| | 57 | | 39.10 |
| | 57 | | 43.00 |
| | 57 | | 50.60 |
| | 57 | | 42.40 |
| | 57 | | 47.70 |
| 18 | 58 | 10/16/2012 | |
| 68 | 59 | 10/16/2012 | |
| 68 | 60 | 10/19/2020 | 61.40 |
| | 60 | | 56.60 |
| | 60 | | 61.70 |
| | 60 | | 61.00 |
| | 60 | | 59.70 |
| | 60 | | 66.20 |
| | 60 | | 63.10 |
| 25 | 61 | 11/7/2012 | |
| 25 | 62 | 11/12/2012 | 69.40 |
| | 62 | | 108.68 |
| | 62 | | 102.98 |
| | 62 | | 105.31 |
| | 62 | | 107.34 |
| | 62 | | 104.23 |
| | 62 | | 99.68 |
| | 62 | | 86.25 |
| | 62 | | 42.42 |
| | 62 | | 36.22 |
| | 62 | | 31.95 |
| | 62 | | 30.82 |
| | 62 | | 44.47 |
| | 62 | | 41.93 |
| | 62 | | 29.33 |

Figure 13C

| Example No. | Lot No. | Date | Advancing Angle |
|---|---|---|---|
| 69 | 63 | 11/12/2012 | 41.94 |
|  | 63 |  | 36.76 |
|  | 63 |  | 34.31 |
|  | 63 |  | 32.57 |
|  | 63 |  | 32.52 |
|  | 63 |  | 40.29 |
|  | 63 |  | 41.53 |
|  | 63 |  | 75.57 |
| 69 | 64 | 11/12/2012 | 72.26 |
|  | 64 |  | 57.00 |
|  | 64 |  | 54.96 |
|  | 64 |  | 41.59 |
|  | 64 |  | 91.89 |
|  | 64 |  | 92.60 |
|  | 64 |  | 82.57 |
|  | 64 |  | 85.19 |
| 69 | 65 | 11/12/2012 | 79.48 |
|  | 65 |  | 80.33 |
|  | 65 |  | 78.63 |
| 29 | 66 | 11/13/2012 |  |
| 29 | 67 | 11/13/2012 |  |
| 29 | 68 | 11/13/2012 |  |
| 32 | 69 | 11/13/2012 |  |
| 32 | 70 | 11/13/2012 |  |
| 32 | 71 | 11/13/2012 |  |
| 31 | 72 | 11/13/2012 |  |
| 31 | 73 | 11/13/2012 |  |
| 69 | 74 | 11/16/2012 | 44.97 |
|  | 74 |  | 54.56 |
|  | 74 |  | 56.44 |
|  | 74 |  | 75.21 |
|  | 74 |  | 37.36 |
|  | 74 |  | 35.55 |
|  | 74 |  | 71.72 |
|  | 74 |  | 24.93 |
|  | 74 |  | 29.66 |
|  | 74 |  | 29.93 |
|  | 74 |  | 34.31 |
| 69 | 75 | 11/16/2012 | 36.17 |
|  | 75 |  | 34.32 |
|  | 75 |  | 34.17 |
|  | 75 |  | 38.35 |
|  | 75 |  | 37.84 |
| 69 | 76 | 11/16/2012 | 36.14 |
|  | 76 |  | 36.77 |
|  | 76 |  | 36.73 |

Figure 13D

| Example No. | Lot No. | Date | Advancing Angle |
|---|---|---|---|
|  | 76 |  | 34.92 |
| 56 | 77 | 11/16/2012 | 52.96 |
|  | 77 |  | 40.59 |
|  | 77 |  | 47.16 |
|  | 77 |  | 37.64 |
|  | 77 |  | 87.41 |
|  | 77 |  | 38.74 |
|  | 77 |  | 103.28 |
|  | 77 |  | 37.71 |
|  | 77 |  | 31.12 |
| 69 | 81 | 11/30/2012 | 67.60 |
|  | 81 |  | 61.74 |
|  | 81 |  | 64.15 |
|  | 81 |  | 71.83 |
|  | 81 |  | 72.67 |
| 69 | 82 | 11/30/2012 | 45.99 |
|  | 82 |  | 72.90 |
|  | 82 |  | 61.73 |
|  | 82 |  | 24.95 |
|  | 82 |  | 24.38 |
| 69 | 83 | 11/30/2012 | 24.94 |
|  | 83 |  | 26.44 |
|  | 83 |  | 27.70 |
|  | 83 |  | 22.97 |
|  | 83 |  | 22.64 |
| 56 | 84 | 11/30/2012 | 74.27 |
|  | 84 |  | 68.61 |
|  | 84 |  | 76.09 |
|  | 84 |  | 76.66 |
|  | 84 |  | 75.72 |
| 69 | 85 | 12/1/2012 | 57.60 |
|  | 85 |  | 28.60 |
|  | 85 |  | 27.90 |
|  | 85 |  | 27.10 |
|  | 85 |  | 26.60 |
|  | 85 |  | 53.90 |
|  | 85 |  | 48.40 |
|  | 85 |  | 25.00 |
|  | 85 |  | 23.00 |
|  | 85 |  | 26.70 |
|  | 85 |  | 27.10 |
|  | 85 |  | 81.90 |
|  | 85 |  | 102.10 |
|  | 85 |  | 78.80 |
|  | 85 |  | 87.40 |
|  | 85 |  | 89.00 |

Figure 13E

| Example No. | Lot No. | Date | Advancing Angle |
|---|---|---|---|
| | 85 | | 85.60 |
| | 85 | | 63.30 |
| | 85 | | 68.00 |
| | 85 | | 66.20 |
| | 85 | | 66.30 |
| | 85 | | 65.20 |
| | 85 | | 61.90 |
| | 85 | | 69.70 |
| | 85 | | 70.19 |
| | 85 | | 70.06 |
| 69 | 86 | 12/1/2012 | 43.37 |
| | 86 | | 35.30 |
| | 86 | | 34.40 |
| | 86 | | 25.10 |
| | 86 | | 23.30 |
| | 86 | | 24.90 |
| | 86 | | 25.50 |
| | 86 | | 43.80 |
| | 86 | | 27.10 |
| | 86 | | 23.10 |
| | 86 | | 27.00 |
| | 86 | | 32.20 |
| | 86 | | 45.20 |
| | 86 | | 41.80 |
| | 86 | | 37.10 |
| | 86 | | 66.20 |
| | 86 | | 73.60 |
| | 86 | | 48.40 |
| | 86 | | 37.10 |
| | 86 | | 49.60 |
| | 86 | | 45.60 |
| | 86 | | 53.61 |
| | 86 | | 109.72 |
| | 86 | | 61.85 |
| | 86 | | 49.47 |
| 27 | 87 | 12/3/2012 | |
| 27 | 88 | 12/3/2012 | |
| 27 | 89 | 12/3/2012 | |
| 27 | 90 | 12/3/2012 | 74.02 |
| | 90 | | 36.56 |
| | 90 | | 94.03 |
| | 90 | | 91.47 |
| 27 | 91 | 12/3/2012 | 27.20 |
| | 91 | | 24.03 |
| | 91 | | 30.07 |
| | 91 | | 27.51 |

Figure 13F

| Example No. | Lot No. | Date | Advancing Angle |
|---|---|---|---|
| 27 | 92 | 12/3/2012 | |
| 30 | 93 | 12/3/2012 | 65.00 |
| | 93 | | 65.00 |
| 30 | 94 | 12/3/2012 | |
| 30 | 95 | 12/4/2012 | |
| 30 | 96 | 12/4/2012 | |
| 31 | 97 | 12/4/2012 | |
| 31 | 98 | 12/4/2012 | |
| 32 | 99 | 12/4/2012 | |
| 31 | 100 | 12/4/2012 | |
| 33 | 101 | 12/6/2012 | 69.30 |
| | 101 | | 65.56 |
| | 101 | | 73.04 |
| 33 | 102 | 12/6/2012 | 33.95 |
| | 102 | | 26.03 |
| | 102 | | 52.78 |
| | 102 | | 38.51 |
| | 102 | | 26.99 |
| | 102 | | 25.45 |
| 35 | 103 | 12/6/2012 | 47.76 |
| | 103 | | 58.66 |
| | 103 | | 57.98 |
| | 103 | | 24.03 |
| | 103 | | 25.56 |
| | 103 | | 71.67 |
| | 103 | | 71.16 |
| | 103 | | 25.27 |
| 35 | 104 | 12/6/2012 | 41.88 |
| | 104 | | 53.13 |
| | 104 | | 24.66 |
| | 104 | | 37.41 |
| | 104 | | 40.17 |
| | 104 | | 54.02 |
| 32 | 105 | 12/6/2012 | |
| 36 | 106 | 12/7/2012 | 49.59 |
| | 106 | | 51.93 |
| | 106 | | 47.25 |
| 37 | 107 | 12/11/2012 | 82.21 |
| | 107 | | 84.14 |
| | 107 | | 83.81 |
| | 107 | | 93.88 |
| | 107 | | 90.38 |
| | 107 | | 72.50 |
| | 107 | | 68.54 |
| 37 | 108 | 12/11/2012 | 80.11 |
| | 108 | | 74.62 |

Figure 13G

| Example No. | Lot No. | Date | Advancing Angle |
|---|---|---|---|
|  | 108 |  | 92.17 |
|  | 108 |  | 73.53 |
| 38 | 109 | 12/12/2012 | 89.45 |
|  | 109 |  | 99.72 |
|  | 109 |  | 92.89 |
|  | 109 |  | 84.12 |
|  | 109 |  | 84.69 |
|  | 109 |  | 85.84 |
| 38 | 110 | 12/12/2012 | 45.07 |
|  | 110 |  | 42.44 |
|  | 110 |  | 45.24 |
|  | 110 |  | 46.63 |
|  | 110 |  | 45.94 |
| 41 | 111 | 12/12/2012 | 34.55 |
|  | 111 |  | 30.24 |
|  | 111 |  | 28.88 |
|  | 111 |  | 44.54 |
| 40 | 112 | 12/13/2012 | 68.44 |
|  | 112 |  | 61.10 |
|  | 112 |  | 75.77 |
| 40 | 113 | 12/13/2012 | 76.51 |
|  | 113 |  | 73.05 |
|  | 113 |  | 80.13 |
|  | 113 |  | 76.34 |
| 40 | 114 | 12/13/2012 |  |
| 40 | 115 | 12/13/2012 |  |
| 39 | 116 | 12/13/2012 |  |
| 39 | 117 | 12/13/2012 |  |
| 41 | 118 | 12/19/2012 | 86.77 |
|  | 118 |  | 85.54 |
|  | 118 |  | 104.14 |
|  | 118 |  | 70.63 |
| 41 | 119 | 12/19/2012 | 85.89 |
|  | 119 |  | 87.02 |
|  | 119 |  | 84.77 |
| 41 | 120 | 12/19/2012 | 87.61 |
|  | 120 |  | 84.35 |
|  | 120 |  | 108.91 |
|  | 120 |  | 69.58 |
| 41 | 121 | 12/19/2012 | 82.71 |
|  | 121 |  | 79.13 |
|  | 121 |  | 86.28 |
| 41 | 122 | 1/2/2013 | 54.53 |
|  | 122 |  | 57.28 |
|  | 122 |  | 57.16 |
|  | 122 |  | 55.64 |

| Example No. | Lot No. | Date | Advancing Angle |
|---|---|---|---|
| | 122 | | 50.35 |
| | 122 | | 65.10 |
| | 122 | | 56.03 |
| | 122 | | 77.13 |
| | 122 | | 60.33 |
| | 122 | | 43.84 |
| | 122 | | 39.50 |
| | 122 | | 48.61 |
| | 122 | | 43.41 |
| 41 | 123 | 1/2/2013 | 56.71 |
| | 123 | | 63.25 |
| | 123 | | 58.89 |
| | 123 | | 63.36 |
| | 123 | | 60.13 |
| | 123 | | 48.83 |
| | 123 | | 45.51 |
| | 123 | | 43.18 |
| | 123 | | 39.72 |
| | 123 | | 78.52 |
| | 123 | | 59.87 |
| | 123 | | 66.41 |
| | 123 | | 52.83 |
| 41 | 124 | 1/2/2013 | 47.94 |
| | 124 | | 47.76 |
| | 124 | | 43.30 |
| | 124 | | 49.54 |
| | 124 | | 42.04 |
| | 124 | | 83.77 |
| | 124 | | 48.28 |
| | 124 | | 43.13 |
| | 124 | | 38.94 |
| | 124 | | 42.93 |
| | 124 | | 39.68 |
| 41 | 125 | 1/2/2013 | 47.41 |
| | 125 | | 47.43 |
| | 125 | | 42.92 |
| | 125 | | 46.74 |
| | 125 | | 42.16 |
| | 125 | | 54.67 |
| | 125 | | 53.33 |
| | 125 | | 55.17 |
| | 125 | | 52.66 |
| | 125 | | 47.09 |
| | 125 | | 41.11 |
| | 125 | | 45.29 |
| | 125 | | 40.39 |

| Example No. | Lot No. | Date | Advancing Angle |
|---|---|---|---|
| 30 | 129 | 1/3/2013 | |
| 30 | 130 | 1/3/2013 | |
| 42 | 131 | 1/5/2013 | 49.91 |
| | 131 | | 66.25 |
| | 131 | | 64.21 |
| | 131 | | 78.03 |
| | 131 | | 17.30 |
| | 131 | | 31.97 |
| | 131 | | 41.70 |
| 42 | 132 | 1/5/2013 | 42.11 |
| | 132 | | 36.09 |
| | 132 | | 22.61 |
| | 132 | | 31.47 |
| | 132 | | 62.39 |
| | 132 | | 46.32 |
| | 132 | | 53.79 |
| 48 | 133 | 1/7/2013 | 69.56 |
| | 133 | | 80.06 |
| | 133 | | 82.47 |
| | 133 | | 46.14 |
| 48 | 134 | 1/7/2013 | 68.47 |
| | 134 | | 98.35 |
| | 134 | | 38.16 |
| | 134 | | 68.88 |
| 51 | 135 | 1/9/2013 | 75.47 |
| | 135 | | 126.52 |
| | 135 | | 77.15 |
| | 135 | | 32.07 |
| | 135 | | 52.66 |
| | 135 | | 86.43 |
| | 135 | | 77.99 |
| 51 | 136 | 1/9/2013 | 55.75 |
| | 136 | | 32.94 |
| | 136 | | 43.99 |
| | 136 | | 36.97 |
| | 136 | | 53.34 |
| | 136 | | 114.83 |
| | 136 | | 52.43 |
| 48 | 137 | 1/9/2013 | 56.10 |
| | 137 | | 71.954 |
| | 137 | | 58.70 |
| | 137 | | 82.08 |
| | 137 | | 27.51 |
| 48 | 138 | 1/0/1900 | |
| 55 | 139 | 1/9/2013 | 75.04 |
| | 139 | | 88.41 |

Figure 13J

| Example No. | Lot No. | Date | Advancing Angle |
|---|---|---|---|
| | 139 | | 75.62 |
| | 139 | | 61.08 |
| 55 | 140 | 1/9/2013 | 34.26 |
| | 140 | | 27.16 |
| | 140 | | 65.25 |
| | 140 | | 29.94 |
| | 140 | | 27.06 |
| | 140 | | 29.90 |
| | 140 | | 26.25 |
| 48 | 143 | 1/9/2013 | 50.43 |
| | 143 | | 27.27 |
| | 143 | | 63.78 |
| | 143 | | 24.61 |
| | 143 | | 86.05 |
| 52 | 144 | 1/9/2013 | 46.54 |
| | 144 | | 35.95 |
| | 144 | | 37.65 |
| | 144 | | 48.03 |
| | 144 | | 28.12 |
| | 144 | | 76.40 |
| | 144 | | 84.49 |
| | 144 | | 31.41 |
| | 144 | | 30.28 |
| 52 | 145 | 1/12/2013 | 42.92 |
| | 145 | | 28.25 |
| | 145 | | 31.39 |
| | 145 | | 31.15 |
| | 145 | | 31.66 |
| | 145 | | 28.85 |
| | 145 | | 42.21 |
| | 145 | | 75.20 |
| | 145 | | 74.63 |
| 54 | 146 | 1/12/2013 | 31.52 |
| | 146 | | 50.88 |
| | 146 | | 28.72 |
| | 146 | | 41.05 |
| | 146 | | 26.02 |
| | 146 | | 28.09 |
| | 146 | | 27.07 |
| | 146 | | 26.58 |
| | 146 | | 27.69 |
| | 146 | | 27.61 |
| 54 | 147 | 1/12/2013 | 37.66 |
| | 147 | | 26.74 |
| | 147 | | 54.17 |

Figure 13K

| Example No. | Lot No. | Date | Advancing Angle |
|---|---|---|---|
| | 147 | | 36.13 |
| | 147 | | 33.42 |
| | 147 | | 36.11 |
| | 147 | | 29.36 |
| | 147 | | 27.73 |
| | 147 | | 28.863 |
| | 147 | | 27.27 |
| | 147 | | 28.02 |
| | 147 | | 77.66 |
| 53 | 148 | 1/12/2013 | 82.46 |
| | 148 | | 83.05 |
| | 148 | | 79.61 |
| | 148 | | 77.05 |
| | 148 | | 90.13 |
| 53 | 149 | 1/0/1900 | 51.03 |
| | 149 | | 30.84 |
| | 149 | | 39.34 |
| | 149 | | 35.24 |
| | 149 | | 51.14 |
| | 149 | | 70.37 |
| | 149 | | 79.26 |
| 51 | 150 | 1/12/2013 | 69.20 |
| | 150 | | 54.80 |
| | 150 | | 89.01 |
| | 150 | | 63.80 |
| 51 | 151 | 1/0/1900 | 34.64 |
| | 151 | | 45.50 |
| | 151 | | 24.33 |
| | 151 | | 43.30 |
| | 151 | | 39.30 |
| | 151 | | 31.60 |
| | 151 | | 23.80 |
| 48 | 152 | 1/12/2013 | |
| 48 | 153 | 1/15/2013 | |
| 50 | 154 | 1/15/2013 | |
| 50 | 155 | 1/15/2013 | |
| 51 | 156 | 1/15/2013 | 62.36 |
| | 156 | | 52.06 |
| | 156 | | 60.99 |
| | 156 | | 68.27 |
| | 156 | | 66.60 |
| | 156 | | 63.90 |
| 51 | 157 | 1/16/2013 | 30.66 |
| | 157 | | 37.67 |
| | 157 | | 31.31 |

Figure 13L

| Example No. | Lot No. | Date | Advancing Angle |
|---|---|---|---|
| | 157 | | 31.76 |
| | 157 | | 27.90 |
| | 157 | | 27.90 |
| | 157 | | 27.40 |
| 51 | 158 | 1/16/2013 | 73.40 |
| | 158 | | 65.00 |
| | 158 | | 68.00 |
| | 158 | | 100.00 |
| | 158 | | 79.00 |
| | 158 | | 55.00 |
| 51 | 159 | 1/17/2013 | 53.20 |
| | 159 | | 34.00 |
| | 159 | | 54.00 |
| | 159 | | 58.00 |
| | 159 | | 66.00 |
| | 159 | | 54.00 |
| 48 | 160 | 1/17/2013 | 71.70 |
| | 160 | | 87.00 |
| | 160 | | 37.00 |
| | 160 | | 99.00 |
| | 160 | | 92.00 |
| | 160 | | 65.00 |
| | 160 | | 50.20 |
| 48 | 161 | 1/17/2013 | 52.50 |
| | 161 | | 63.00 |
| | 161 | | 57.00 |
| | 161 | | 55.00 |
| | 161 | | 41.00 |
| | 161 | | 47.00 |
| | 161 | | 52.00 |
| 49 | 162 | 1/17/2013 | 37.00 |
| | 162 | | 32.00 |
| | 162 | | 27.00 |
| | 162 | | 59.00 |
| | 162 | | 29.00 |
| | 162 | | 38.00 |
| 51 | 163 | 2/7/2013 | 63.69 |
| | 163 | | 74.34 |
| | 163 | | 69.32 |
| | 163 | | 63.32 |
| | 163 | | 25.53 |
| | 163 | | 74.89 |
| | 163 | | 75.88 |
| | 163 | | 70.06 |
| | 163 | | 62.04 |

Figure 13M

| Example No. | Lot No. | Date | Advancing Angle |
|---|---|---|---|
| | 163 | | 67.36 |
| | 163 | | 54.11 |
| 51 | 164 | 2/7/2013 | |
| | | | |
| | | | |
| | | | |
| | | | |
| | | | |
| | | | |
| | | | |
| | | | |
| | | | |
| | | | |
| 72 | 167 | 2/19/2013 | 62.89 |
| | 167 | | 56.76 |
| | 167 | | 57.20 |
| | 167 | | 69.59 |
| | 167 | | 71.71 |
| | 167 | | 54.50 |
| | 167 | | 55.38 |
| | 167 | | 44.74 |
| | 167 | | 43.16 |
| | 167 | | 63.82 |
| | 167 | | 66.28 |
| | 167 | | 87.29 |
| | 167 | | 84.21 |
| 72 | 168 | 2/19/2013 | 70.95 |
| | 168 | | 102.42 |
| | 168 | | 87.63 |
| | 168 | | 74.96 |
| | 168 | | 76.22 |
| | 168 | | 85.25 |
| | 168 | | 88.20 |
| | 168 | | 51.64 |
| | 168 | | 51.85 |
| | 168 | | 44.67 |
| | 168 | | 46.70 |
| | 168 | | 69.54 |
| | 168 | | 72.31 |
| 72 | 169 | 2/19/2013 | 49.88 |
| | 169 | | 70.90 |
| | 169 | | 67.32 |
| | 169 | | 47.00 |
| | 169 | | 45.99 |
| | 169 | | 38.65 |
| | 169 | | 40.77 |

Figure 13N

| Example No. | Lot No. | Date | Advancing Angle |
|---|---|---|---|
| | 169 | | 42.54 |
| | 169 | | 45.87 |
| | 169 | 2/19/2013 | 60.11 |
| | 169 | | 80.87 |
| | 169 | | 78.10 |
| | 169 | | 52.69 |
| | 169 | | 52.66 |
| | 169 | | 49.40 |
| | 169 | | 46.95 |
| 72 | 170 | 2/19/2013 | 63.32 |
| | 170 | | 85.59 |
| | 170 | | 84.31 |
| | 170 | | 69.34 |
| | 170 | | 72.00 |
| | 170 | | 48.64 |
| | 170 | | 48.81 |
| | 170 | | 51.29 |
| | 170 | | 52.36 |
| | 170 | | 34.27 |
| | 170 | | 72.97 |
| | 170 | | 76.98 |
| 72 | 171 | 2/19/2013 | 61.26 |
| | 171 | | 35.74 |
| | 171 | | 47.08 |
| | 171 | | 80.39 |
| | 171 | | 80.88 |
| | 171 | | 62.28 |
| | 171 | | 66.55 |
| | 171 | | 74.34 |
| | 171 | | 72.09 |
| | 171 | | 35.51 |
| | 171 | | 52.71 |
| | 171 | | 63.01 |
| | 171 | | 64.49 |
| 72 | 172 | 2/19/2013 | 78.21 |
| | 172 | | 72.62 |
| | 172 | | 73.96 |
| | 172 | | 58.79 |
| | 172 | | 59.47 |
| | 172 | | 103.28 |
| | 172 | | 101.10 |
| | 172 | | 101.71 |
| | 172 | | 101.78 |
| | 172 | | 59.69 |
| | 172 | | 58.67 |
| | 172 | | 72.92 |

Figure 13O

| Example No. | Lot No. | Date | Advancing Angle |
|---|---|---|---|
|  | 172 |  | 74.58 |
| 72 | 172 | 2/19/2013 | 80.77 |
|  | 172 |  | 79.41 |
|  | 172 |  | 79.11 |
|  | 172 |  | 80.52 |
|  | 172 |  | 79.48 |
|  | 172 |  | 92.23 |
|  | 172 |  | 96.06 |
|  | 172 |  | 88.38 |
|  | 172 |  | 90.77 |
|  | 172 |  | 63.80 |
|  | 172 |  | 63.60 |
|  | 172 |  | 78.51 |
|  | 172 |  | 77.33 |
| 72 | 173 | 2/19/2013 | 40.16 |
|  | 173 |  | 41.09 |
|  | 173 |  | 38.22 |
|  | 173 |  | 36.86 |
|  | 173 |  | 34.10 |
|  | 173 |  | 45.61 |
|  | 173 |  | 48.44 |
|  | 173 |  | 37.82 |
|  | 173 |  | 29.50 |
|  | 173 |  | 38.68 |
|  | 173 |  | 39.35 |
|  | 173 |  | 45.22 |
|  | 173 |  | 47.03 |
| 72 | 174 | 2/19/2013 | 56.43 |
|  | 174 |  | 47.80 |
|  | 174 |  | 48.36 |
|  | 174 |  | 40.77 |
|  | 174 |  | 46.60 |
|  | 174 |  | 62.85 |
|  | 174 |  | 62.18 |
|  | 174 |  | 70.66 |
|  | 174 |  | 72.25 |
| 72 | 175 | 2/19/2013 | 48.95 |
|  | 175 |  | 42.35 |
|  | 175 |  | 44.14 |
|  | 175 |  | 41.28 |
|  | 175 |  | 44.11 |
|  | 175 |  | 56.39 |
|  | 175 |  | 61.18 |
|  | 175 |  | 61.68 |
|  | 175 |  | 61.04 |
|  | 175 |  | 39.58 |

Figure 13P

| Example No. | Lot No. | Date | Advancing Angle |
|---|---|---|---|
| | 175 | | 37.73 |
| 72 | 175 | 2/19/2013 | 40.51 |
| | 175 | | 39.98 |
| | 175 | | 35.42 |
| | 175 | | 32.33 |
| | 175 | | 31.91 |
| | 175 | | 46.09 |
| | 175 | | 45.72 |
| | 175 | | 60.23 |
| | 175 | | 58.03 |
| | 175 | | 24.92 |
| | 175 | | 30.46 |
| 72 | 176 | 2/19/2013 | 52.34 |
| | 176 | | 57.74 |
| | 176 | | 55.93 |
| | 176 | | 48.25 |
| | 176 | | 47.14 |
| | 176 | | 33.65 |
| | 176 | | 41.33 |
| | 176 | | 76.82 |
| | 176 | | 61.76 |
| | 176 | | 62.15 |
| | 176 | | 45.21 |
| | 176 | | 45.74 |
| 72 | 177 | 2/19/2013 | 45.75 |
| | 177 | | 42.93 |
| | 177 | | 46.81 |
| | 177 | | 50.16 |
| | 177 | | 48.96 |
| | 177 | | 50.10 |
| | 177 | | 44.43 |
| | 177 | | 39.80 |
| | 177 | | 47.92 |
| | 177 | | 45.89 |
| | 177 | | 48.58 |
| | 177 | | 41.69 |
| | 177 | | 41.79 |
| 72 | 178 | 2/19/2013 | 40.36 |
| | 178 | | 38.98 |
| | 178 | | 44.55 |
| | 178 | | 38.50 |
| | 178 | | 22.37 |
| | 178 | | 39.39 |
| | 178 | | 50.00 |
| | 178 | | 40.08 |
| | 178 | | 46.42 |

Figure 13Q

| Example No. | Lot No. | Date | Advancing Angle |
|---|---|---|---|
| | 178 | | 40.70 |
| | 178 | | 42.63 |
| 72 | 178 | 2/19/2013 | 35.39 |
| | 178 | | 36.25 |
| | 178 | | 36.21 |
| | 178 | | 39.45 |
| | 178 | | 40.21 |
| | 178 | | 38.39 |
| | 178 | | 38.42 |
| | 178 | | 33.52 |
| | 178 | | 34.89 |
| | 178 | | 27.15 |
| | 178 | | 29.46 |
| 73 | 179 | 3/4/2013 | 69.28 |
| | 179 | | 91.86 |
| | 179 | | 92.42 |
| | 179 | | 41.88 |
| | 179 | | 38.48 |
| | 179 | | 79.64 |
| | 179 | | 75.65 |
| | 179 | | 85.11 |
| | 179 | | 85.01 |
| | 179 | | 52.19 |
| | 179 | | 50.51 |
| 73 | 179 | 3/4/2013 | 70.47 |
| | 179 | | 66.27 |
| | 179 | | 67.24 |
| | 179 | | 56.93 |
| | 179 | | 57.89 |
| | 179 | | 97.32 |
| | 179 | | 97.72 |
| | 179 | | 74.83 |
| | 179 | | 75.57 |
| | 179 | | 54.97 |
| | 179 | | 55.92 |
| 73 | 180 | 3/4/2013 | 72.29 |
| | 180 | | 58.24 |
| | 180 | | 51.32 |
| | 180 | | 59.18 |
| | 180 | | 62.37 |
| | 180 | | 97.80 |
| | 180 | | 99.90 |
| | 180 | | 73.40 |
| | 180 | | 72.42 |
| | 180 | | 74.60 |
| | 180 | | 73.66 |

Figure 13R

| Example No. | Lot No. | Date | Advancing Angle |
|---|---|---|---|
| 73 | 180 | 3/4/2013 | 60.65 |
|  | 180 |  | 43.87 |
|  | 180 |  | 39.54 |
|  | 180 |  | 68.43 |
|  | 180 |  | 67.70 |
|  | 180 |  | 60.82 |
|  | 180 |  | 61.41 |
|  | 180 |  | 64.75 |
|  | 180 |  | 64.31 |
|  | 180 |  | 67.96 |
|  | 180 |  | 67.69 |
| 73 | 181 | 3/5/2013 | 99.18 |
|  | 181 |  | 99.69 |
|  | 181 |  | 104.80 |
|  | 181 |  | 98.92 |
|  | 181 |  | 100.89 |
|  | 181 |  | 98.68 |
|  | 181 |  | 92.11 |
| 73 | 181 | 3/5/2013 | 95.20 |
|  | 181 |  | 56.08 |
|  | 181 |  | 100.83 |
|  | 181 |  | 86.85 |
|  | 181 |  | 97.63 |
|  | 181 |  | 99.44 |
|  | 181 |  | 100.70 |
|  | 181 |  | 103.82 |
|  | 181 |  | 105.82 |
|  | 181 |  | 100.57 |
|  | 181 |  | 100.30 |
| 73 |  |  |  |
|  | 182 | 3/15/2013 | 71.6 |
|  | 182 |  | 71.6 |
|  | 182 |  | 52.6 |
|  | 182 |  | 51.1 |
| 73 | 183 |  | 37.2 |
|  | 183 |  | 37.4 |
|  | 183 |  | 38.0 |
|  | 183 |  | 34.4 |
|  | 183 |  | 38.5 |
|  | 183 |  | 31.6 |
| 73 | 184 |  | 65.7 |
|  | 184 |  | 66.3 |
|  | 184 |  | 74.3 |
|  | 184 |  | 74.1 |
|  | 184 |  | 71.3 |
|  | 184 |  | 71.8 |

Figure 13S

| Example No. | Lot No. | Date | Advancing Angle |
|---|---|---|---|
| 73 | 185 | | 42.6 |
| | 185 | | 41.9 |
| | 185 | | 37.8 |
| | 185 | | 38.3 |
| | 185 | | 32.3 |
| | 185 | | 28.9 |

Matlab Code Used to Determine Advancing and Receding Contact Angles

```
%%For Windows: change / to \, mmreader to VideoReader, mov to wmv clear all;
clc;

warning('off','Images:initSize:adjustingMag');

input('Hit enter to choose folder containing video files: ');

FolderName = uigetdir('..\Contact Angle Videos','Pick folder containing videos to analyze: ');
mkdir(strcat(FolderName,'\BW Images'))
mkdir(strcat(FolderName,'\Frame Plots'))

% clc;
% ThreshPrompt = input('Increase sensitivity of B/W conversion? Y or N: ','s');
%
% if ThreshPrompt == 'Y'
%     ThreshOffset = 0.2;
% else
%     ThreshOffset = 0;
% end ThreshOffset = 0;

clc;
downSample = input('Enter frame increment (1 = all frames, 24 = once per second): ');
sampleLength = 5;    % length of data to calculate angles, in sec
oneSec = floor(24/downSample);
sampleNumber = oneSec*sampleLength-1;    % length of data to calculate angles, in frames vidStruct = dir(strcat(FolderName,'\*.wmv'));
nFiles = size(vidStruct,1);
for i = 1:nFiles
    vidNames{i} = char(vidStruct(i).name);
end AllAngles = {'File' 'Advancing Angle' 'Receding Angle' 'Pixel Width Change'};

fid = fopen(strcat(FolderName,'\Results.csv'),'wt');
fprintf(fid,'%s,%s,%s,%s\n', AllAngles{1,:});
```

Figure 14B

```
vidName = char(vidNames(1,1));
vidObj = VideoReader(strcat(FolderName,'\',vidName));

nFrames = vidObj.NumberOfFrames;

mov{1} = read(vidObj,floor(nFrames/2));

RGB = mov{1,1}(:,:,1:3);

% I = rgb2gray(RGB);
% threshold = graythresh(I)+ThreshOffset;
% BW = im2bw(I,threshold);
% % remove all small objects
% BW = bwareaopen(BW,floor(vidObj.Width*vidObj.Height/100));
% % fill any gaps
% SE = strel('disk',2);
% BW = imclose(BW,SE);
% % fill any holes
% BW = imfill(BW,'holes');

IDX = otsu(RGB,3);
IDX = (IDX ~= 3);
BW = imfill(IDX,'holes');
BW = (BW == 0);

% clc;
% disp('Hit enter to crop video around bubble-lens interface: ');
% input('(As much white as possible without going below center of bubble)');
% [BWcrop rect] = imcrop(BW);
% close all;

% left = floor(rect(1));
% right = floor(rect(1)+rect(3));
% top = floor(rect(2));
% bottom = floor(rect(2)+rect(4));

shortbubblelength = 40;
longbubblelength = 80;
lenslength = 80;

% height = top-bottom+1;
% width = right-left+1;
```

Figure 14C

```
height = vidObj.height;
width = vidObj.width;

for x = 1:nFiles

LeftContactAngles=0;
    RightContactAngles=0;
    ContactAngles=0;
    Widths=0;
    slope=0;
    deltaWidth=0;
    SmoothWidths=0;

vidName = char(vidNames(1,x));
    vidObj = VideoReader(strcat(FolderName,'\',vidName));

nFrames = vidObj.NumberOfFrames;

for v = 1:downSample:nFrames-1
        newIndex = 1 + floor(v/downSample);
        mov{newIndex} = read(vidObj,v);
    end downSampleFrames = newIndex;

bubblelength = shortbubblelength;

RGB = mov{1,downSampleFrames}(:,:,1:3);

for k = 1:downSampleFrames clc;
        StatusStr = ['Analyzing ',num2str(x),' of ',num2str(nFiles),' files, ',num2str(k),' of ',num2str(downSampleFrames-1),' frames.'];
        disp(StatusStr);

% mov = read(vidObj,k);

% RGB = mov(top:bottom,left:right,1:3);
        RGB = mov{1,k}(:,:,1:3);

% I = rgb2gray(RGB);
        % threshold = graythresh(I)+ThreshOffset;
        % BW = im2bw(I,threshold);
```

Figure 14D

```
% % remove all small objects
% BW = bwareaopen(BW,floor(vidObj.Width*vidObj.Height/100));
% % fill any gaps
% SE = strel('disk',2);
% BW = imclose(BW,SE);
% % fill any holes
% BW = imfill(BW,'holes');

IDX = otsu(RGB,3);
IDX = (IDX ~= 3);
BW = imfill(IDX,'holes');
BW = (BW == 0);

whitecount = sum(BW,1);

if(isempty(find(whitecount==0,1)))
    break;
end leftcornercolumn = find(whitecount==0,1,'first')-1;
rightcornercolumn = find(whitecount==0,1,'last')+1;
centercolumn = (leftcornercolumn+rightcornercolumn)/2;

while(find(BW(:,leftcornercolumn-1)==1,1,'first')<find(BW(:,leftcornercolumn)==1,1,'first'))
    leftcornercolumn=leftcornercolumn-1;
end while(find(BW(:,rightcornercolumn+1)==1,1,'first')<find(BW(:,rightcornercolumn)==1,1,'first'))
    rightcornercolumn=rightcornercolumn+1;
end leftcornerrow = find(BW(:,leftcornercolumn-1)==1,1,'first');
rightcornerrow = find(BW(:,rightcornercolumn+1)==1,1,'first');

%%%%%% LEFT %%%%%%
leftbubbleboundary = [];
leftlensboundary = [];
adjustcount=1;
while isempty(leftbubbleboundary) || isempty(leftlensboundary)
    leftbubbleboundary = bwtraceboundary(BW, [leftcornerrow, leftcornercolumn], 'NE', 8, bubblelength);
```

Figure 14E

```
        leftlensboundary = bwtraceboundary(BW, [leftcornerrow, leftcornercolumn], 'NE', 8,
lenslength, 'counter');
        if isempty(leftbubbleboundary) || isempty(leftlensboundary)
            leftcornercolumn=leftcornercolumn-adjustcount;
            adjustcount=adjustcount+1;
            leftbubbleboundary = bwtraceboundary(BW, [leftcornerrow, leftcornercolumn], 'NE',
8, bubblelength);
            leftlensboundary = bwtraceboundary(BW, [leftcornerrow, leftcornercolumn], 'NE', 8,
lenslength, 'counter');
        end
        if isempty(leftbubbleboundary) || isempty(leftlensboundary)
            leftcornercolumn=leftcornercolumn+adjustcount;
            adjustcount=adjustcount-1;
            leftbubbleboundary = bwtraceboundary(BW, [leftcornerrow, leftcornercolumn], 'NE',
8, bubblelength);
            leftlensboundary = bwtraceboundary(BW, [leftcornerrow, leftcornercolumn], 'NE', 8,
lenslength, 'counter');
        end
    end leftbubblecoeff =
polyfit(transpose(leftbubbleboundary(:,2)),transpose(leftbubbleboundary(:,1)),1);
    leftlenscoeff = polyfit(transpose(leftlensboundary(:,2)),transpose(leftlensboundary(:,1)), 1);

leftfitbubblelength = max(leftbubbleboundary(:,2))-min(leftbubbleboundary(:,2))+1;
    leftfitlenslength = max(leftlensboundary(:,2))-min(leftlensboundary(:,2))+1;

leftybubble = zeros(leftfitbubblelength,1);
    leftylens = zeros(leftfitlenslength,1);
    leftxbubble = zeros(leftfitbubblelength,1);
    leftxlens = zeros(leftfitlenslength,1);
    leftxbubble(1) = min(leftbubbleboundary(:,2));
    leftxlens(1) = min(leftlensboundary(:,2));

for i = 1:leftfitbubblelength;
        if i>1
            leftxbubble(i) = leftxbubble(i-1)+1;
        end
        leftybubble(i) = leftbubblecoeff(1)*leftxbubble(i)+leftbubblecoeff(2);
    end for i = 1:leftfitlenslength;
        if i>1
```

Figure 14F

```
      leftxlens(i) = leftxlens(i-1)+1;
    end
    leftylens(i) = leftlenscoeff(1)*leftxlens(i)+leftlenscoeff(2);
end leftbubbleslope = leftbubblecoeff(1);
leftlensslope = leftlenscoeff(1);

leftbubbleangle = atan(leftbubbleslope)*180/pi();
leftlensangle = atan(leftlensslope)*180/pi();

if(leftbubbleslope < 0)
    LeftContactAngle = -leftbubbleangle+leftlensangle;
else
    LeftContactAngle = 180-leftbubbleangle+leftlensangle;
end LeftContactAngles(k) = LeftContactAngle;
%%%%%% LEFT %%%%%%

%%%%%% RIGHT %%%%%%
rightbubbleboundary = [];
rightlensboundary = [];
adjustcount=1;
while isempty(rightbubbleboundary) || isempty(rightlensboundary)
    rightlensboundary = bwtraceboundary(BW, [rightcornerrow, rightcornercolumn], 'NE', 8, lenslength);
    rightbubbleboundary = bwtraceboundary(BW, [rightcornerrow, rightcornercolumn], 'NE', 8, bubblelength, 'counter');
    if isempty(rightbubbleboundary) || isempty(rightlensboundary)
        rightcornercolumn=rightcornercolumn+adjustcount;
        adjustcount=adjustcount+1;
        rightlensboundary = bwtraceboundary(BW, [rightcornerrow, rightcornercolumn], 'NE', 8, lenslength);
        rightbubbleboundary = bwtraceboundary(BW, [rightcornerrow, rightcornercolumn], 'NE', 8, bubblelength, 'counter');
    end
    if isempty(rightbubbleboundary) || isempty(rightlensboundary)
        rightcornercolumn=rightcornercolumn-adjustcount;
        adjustcount=adjustcount-1;
        rightlensboundary = bwtraceboundary(BW, [rightcornerrow, rightcornercolumn], 'NE', 8, lenslength);
```

Figure 14G

```
        rightbubbleboundary = bwtraceboundary(BW, [rightcornerrow, rightcornercolumn], 'NE',
8, bubblelength, 'counter');
    end
    end rightbubblecoeff =
polyfit(transpose(rightbubbleboundary(:,2)),transpose(rightbubbleboundary(:,1)),1);
    rightlenscoeff =
polyfit(transpose(rightlensboundary(:,2)),transpose(rightlensboundary(:,1)), 1);

rightfitbubblelength = max(rightbubbleboundary(:,2))-min(rightbubbleboundary(:,2))+1;
    rightfitlenslength = max(rightlensboundary(:,2))-min(rightlensboundary(:,2))+1;

rightybubble = zeros(rightfitbubblelength,1);
    rightylens = zeros(rightfitlenslength,1);
    rightxbubble = zeros(rightfitbubblelength,1);
    rightxlens = zeros(rightfitlenslength,1);
    rightxbubble(1) = min(rightbubbleboundary(:,2));
    rightxlens(1) = min(rightlensboundary(:,2));

for i = 1:rightfitbubblelength;
       if i>1
          rightxbubble(i) = rightxbubble(i-1)+1;
       end
       rightybubble(i) = rightbubblecoeff(1)*rightxbubble(i)+rightbubblecoeff(2);
    end for i = 1:rightfitlenslength;
       if i>1
          rightxlens(i) = rightxlens(i-1)+1;
       end
       rightylens(i) = rightlenscoeff(1)*rightxlens(i)+rightlenscoeff(2);
    end rightbubbleslope = rightbubblecoeff(1);
    rightlensslope = rightlenscoeff(1);

rightbubbleangle = atan(rightbubbleslope)*180/pi();
    rightlensangle = atan(rightlensslope)*180/pi();

if(rightbubbleslope > 0)
       RightContactAngle = rightbubbleangle+leftlensangle;
```

Figure 14H

```
    else
        RightContactAngle = 180+rightbubbleangle+leftlensangle;
    end RightContactAngles(k) = RightContactAngle;
    %%%%%% RIGHT %%%%%% if k == floor(downSampleFrames/2)
        close all;
        BWImage = figure;
        imshow(BW);
        title(vidName(1:length(vidName)-4));
        hold on;
        plot(transpose(leftxbubble),transpose(leftybubble),'r','LineWidth',2);
        plot(transpose(leftxlens),transpose(leftylens),'c','LineWidth',2);
        plot(transpose(rightxbubble),transpose(rightybubble),'r','LineWidth',2);
        plot(transpose(rightxlens),transpose(rightylens),'c','LineWidth',2);
        saveas(BWImage,strcat(FolderName,'\BW Images\BW-',vidName(1:length(vidName)-
4)),'png');
        hold off;
    end if LeftContactAngle>60 || RightContactAngle>60
        bubblelength=longbubblelength;
    end width = rightcornercolumn-leftcornercolumn;
    Widths(k) = width;

end

ContactAngles = (LeftContactAngles + RightContactAngles)/2;

k = length(ContactAngles);

%   %%%%INFLECTION%%%%
%   SmoothWidths = smooth(Widths,20);
%   for i=1:k-2
%       slope(i) = SmoothWidths(i+2)-SmoothWidths(i);
%   end
%
%   if(isempty(find(fliplr(slope)>-2,1)))
%       AdvancingStart = k-sampleNumber;
%   else
```

Figure 14I

```
%       AdvancingStart = k-find(fliplr(slope)>-2,1,'first');
%   end
%
%   if AdvancingStart > k-sampleNumber;
%       AdvancingStart = k-sampleNumber;
%   end
%   %%%%INFLECTION%%%%

%%%%INFLECTION%%%%
  for i=1:k-oneSec
     deltaWidth(i) = Widths(i+oneSec) - Widths(i);
  end if(isempty(find(fliplr(deltaWidth)>-5,1)))
     AdvancingStart = k-sampleNumber;
  else
     AdvancingStart = k-find(fliplr(deltaWidth)>-5,1,'first')+oneSec;
  end if AdvancingStart > k-sampleNumber;
     AdvancingStart = k-sampleNumber;
  end
  %%%%INFLECTION%%%%

%AdvancingStart = k-sampleNumber;

AdvancingAngle = median(ContactAngles(AdvancingStart:AdvancingStart+sampleNumber));

disp('Advancing Angle: '),disp(AdvancingAngle);

MinLocation = find(Widths==min(Widths(1:k/2)),1,'first');
  MidWidth = (max(Widths)-min(Widths(1:k/2)))/2+min(Widths(1:k/2));
  RecedingStart = find(Widths(MinLocation:k)>MidWidth,1,'first')+MinLocation -
floor(sampleNumber/2);
  RecedingAngle = median(ContactAngles(RecedingStart:RecedingStart+sampleNumber));
  disp('Receding Angle: '),disp(RecedingAngle);

vidPlot = figure;
  [AX,H1,H2] = plotyy(1:k,ContactAngles,1:k,Widths);
  xlabel('Frame');
  set(get(AX(1),'Ylabel'),'String','Contact Angle (Degrees)') ;
  set(get(AX(2),'Ylabel'),'String','Bubble Width (Pixels)');
```

Figure 14J

```
   set(H1,'LineStyle','.');
   set(H2,'LineStyle','.');
   title(vidName(1:length(vidName)-4));
   hold on;

scatter(AdvancingStart:AdvancingStart+sampleNumber,ContactAngles(AdvancingStart:Advanci
ngStart+sampleNumber),'filled','red');

scatter(RecedingStart:RecedingStart+sampleNumber,ContactAngles(RecedingStart:RecedingSta
rt+sampleNumber),'filled','red');
   saveas(vidPlot,strcat(FolderName,'\Frame Plots\',vidName(1:length(vidName)-
4),'.png'),'png');
   hold off;

AllAngles{x+1,1} = vidName(1:length(vidName)-4);
   AllAngles{x+1,2} = AdvancingAngle;
   AllAngles{x+1,3} = RecedingAngle;
   AllAngles{x+1,4} = max(Widths)-min(Widths);

fprintf(fid,'%s,%d,%d,%d\n',AllAngles{x+1,:});
end fclose(fid);
```

CONTACT LENS WITH A HYDROPHILIC LAYER

CROSS-REFERENCE TO RELATED APPLICATIONS

This application is a division of U.S. patent application Ser. No. 15/095,759, filed on Apr. 11, 2016 entitled "Contact Lens with a Hydrophilic Layer," now U.S. Pat. No. 10,330,951, which is a continuation of U.S. patent application Ser. No. 14/660,728, filed on Mar. 17, 2015 entitled "Contact Lens with a Hydrophilic Layer," now U.S. Pat. No. 9,310,627, which is a continuation of International Appl. No. PCT/US2014/065588 filed on Nov. 14, 2014 entitled "Contact Lens with a Hydrophilic Layer," which claims the benefit of U.S. Provisional Patent Application No. 61/905,092 filed on Nov. 15, 2013 entitled "Contact Lens with a Hydrophilic Layer," the disclosure of each of which is herein incorporated by reference in its entirety.

This application is also related to U.S. Patent Applications of Havenstrite, et al., including application Ser. No. 13/975,868 as filed on Aug. 26, 2013, Publication No. US-2014-0055741-A1; App. No. 61/693,689 as filed on Aug. 27, 2012, App. No. 61/800,835, as filed on Mar. 15, 2013, and App. No. 61/800,959, as filed on Mar. 15, 2013, each application entitled "Multilayered Contact Lens," which are each herein incorporated by reference in its entirety. This application is also related to U.S. Provisional Patent Application of Havenstrite, et al., App. No. 61/834,813 as filed on Jun. 13, 2013, entitled "Contact Lens with a Hydrophilic Layer," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the technology relate to a contact lens with improved biocompatibility and wearability and methods for making the improved lens. More particularly, the technology relates to a contact lens with a highly stable hydrogel layer covering a lens core.

BACKGROUND

Contact lenses are medical devices that are placed in contact with the ocular surface and are used for vision correction, aesthetic purposes, and to treat ocular pathologies. Substances and materials can be deposited onto a contact lens's surface to improve the biocompatibility of the lens and therefore improve the interaction of the lens with the ocular region.

The current generation of contact lenses commonly includes a silicone containing core material. These lenses have many advantages over their rigid plastic predecessors. For example, silicone-containing lenses are biocompatible for the eye and have improved oxygen and fluid permeability for normal ocular surface health. However, despite these advantages, a major challenge for silicone-containing lenses is the hydrophobicity of silicone containing materials, which can lead to abrasion of ocular tissue and infection. As such, embodiments described herein provide for a contact lens having improved hydrophilicity and biocompatibility as well as practical and cost-effective methods for making these lenses.

Rigid gas permeable (RGP) lenses are another alternative to soft contact lenses. RGP lenses are designed for longer term wear than soft lenses and can provide crisper vision than current soft lenses. RGP lenses can also automatically correct most astigmatism. The RGP lenses can be less comfortable to wear than soft lenses. In some cases the RGP lenses can have an adjustment period of a few days to break in.

Hybrid RGP lenses have an RGP core with a soft material formed on the outside surface of the RGP core. The soft material can improve the comfort level of the hybrid lens while still offering some of the benefits of the RGP lenses.

An additional challenge with contact lens technology is the tendency for protein binding and absorption at the ocular site. For example, a contact lens may bind proteins on the lens to create protein deposits in the eye area. Additionally, the lens can cause structural changes including protein denaturation that can elicit an immune response such as tearing, reddening, or swelling in the ocular region. Accordingly, contemplated embodiments provide for contact lenses and methods of making lenses with improved resistance to undesirable protein interactions at the ocular site.

A further concern with contact lens use is that some users experience discomfort that is similar to the profile of patients that have a dry eye disease. Dry eye disease is considered to be a consequence of a disruption of the tear film that covers the surface of the eye, or a particular vulnerability to such disruption. This tear film is an aqueous layer disposed between an underlying mucous layer that is secreted by corneal cells, and an overlying lipid layer that is secreted by Meibomian glands on the conjunctival surface of the eyelids. The tear film includes an aqueous pool that transits across the eye surface, having a flow path that, to some degree, may be independent of the lipid layers that it is disposed between at any point in time.

Integrity of the tear film is important for such critical functions as oxygen and ion transport, and lubricating the eye surface, which is subject to a constant sliding contact by the eyelids. It is likely that dry eye disease actually exists as a spectrum of tear film vulnerability to disruption. In some cases, patients may have a low-level dry eye disease that manifests when the integrity of the film is challenged by the presence of a contact lens. To address this concern, some embodiments of the invention provide for contact lens technology that diminishes or substantially eliminates contact lens disruption of the tear film.

As can be appreciated, dry eye disease may be referred to herein as a non-limiting example for illustration purposes. The methods and devices described may be used to treat or prevent other ocular pathologies including, but not limited to, glaucoma, corneal ulcers, scleritis, keratitis, iritis, and corneal neovascularization.

SUMMARY OF THE DISCLOSURE

In general, in one embodiment, a coated contact lens includes a lens core with an equilibrium water content of less than about 2%, the lens core including an outer surface and a hydrogel layer covalently attached to at least a portion of the outer surface, the hydrogel layer adapted to contact an ophthalmic surface, wherein the hydrogel layer includes a hydrophilic polymer population of one or more species.

This and other embodiments can include one or more of the following features. The one or more species can be at least partially cross-linked. The lens core can be substantially free of water. The hydrophilic polymer population can include a first species selected from the group consisting of: polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer population can include a second species selected from the group consisting of: polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer population can include a first species including PEG. The hydrophilic polymer population can include a second species including polyacrylamide. The contact lens can be a rigid gas permeable contact lens. The lens core can include a rigid gas permeable material. The rigid gas permeable material can include fluorine. The rigid gas permeable material can include a fluoro-acrylate. The rigid gas permeable material can include silicone. The lens can include a polysiloxane. The lens can include a cross-linked polysiloxane. The lens core can consist essentially of a cross-linked polysiloxane. The lens core can have an elastic modulus of less than about 1.8 MPa. The lens core can have an elastic modulus of greater than about 500 MPa. The lens core can have an equilibrium water content of less than about 1%. The lens core can have an equilibrium water content of less than about 0.5%. The lens core can be a soft contact lens. The one or more species can be chemically cross-linked. The one or more species can be ionically cross-linked. The one or more species can be physically cross-linked. The hydrogel layer can substantially surround the outer surface of the core. The hydrogel layer and core can be substantially optically clear. The hydrogel layer can be adapted to allow optical transmission through the hydrogel layer to the ophthalmic surface. The hydrogel layer can include a thickness between about 50 nm to about 500 nm. The hydrogel layer can have a thickness less than about 5 micron. The hydrogel layer can have a maximum thickness between about 1 micron to about 5 microns. The hydrogel polymer layer can have a thickness between about 100 nm to about 250 nm. The hydrogel layer can include a thickness between about 1 nm to about 50 nm. The hydrogel layer can include a thickness less than about 50 nm. The hydrogel layer can include a thickness less than about 40 nm. The hydrogel layer can include a thickness below about 100 nm. The hydrogel layer can include a maximum thickness of about 10 microns. A first portion of the hydrogel layer can include a first thickness different from a second thickness of a second portion of the hydrogel layer. The first species can include a reactive electrophilic group or a reactive nucleophilic group and the second species can include a reactive electrophilic group or a reactive nucleophilic group complementary to the first species, the reactive electrophilic group and the reactive nucleophilic group can be adapted to react to thereby form cross-links between the first species to the second species. The reactive electrophilic group can be selected from the group including amino-reactive groups, sulfhydryl-reactive groups, carboxyl groups, hydroxyl groups, haloalkyl groups, dienophile groups, aldehyde or ketone groups, alkenes, epoxides, and phosphoramidites. The reactive nucleophilic group can be selected from the group including amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites. At least one of the reactive electrophilic group of the first species or the reactive electrophilic group of the second species can be covalently linked to the outer surface of the core. The lens can have an advancing contact angle as measured by a captive bubble test of less than about 50 degrees. The lens can have an advancing contact angle as measured by a captive bubble test of less than about 35 degrees. The core can be substantially free of silicone. The lens can have a critical coefficient of friction of less than about 0.056. The lens can have a water break up time of greater than about 20 seconds. The protein deposition can be less than about 5 micrograms of protein per lens. The lens may not substantially denature proteins. The lens can denature less than about 5% of protein contacting the lens. The lens can have a lipid deposition of less than about 100 micrograms of lipid per lens. The hydrophilic polymer layer can further include at least one active agent. The at least one active agent can be selected from the group including a UV-absorbing agent, a visibility tinting agent, an antimicrobial agent, a bioactive agent, a leachable lubricant, a leachable tear-stabilizing agent, or any mixture thereof. The antimicrobial agent can include silver nanoparticles. The lens can have an oxygen transmissibility (DK/t) of greater than 200. The lens can have an oxygen transmissibility (DK/t) of greater than 300.

In general, in one embodiment, a multi-layer contact lens includes a lens core layer covered by an outer hydrophilic polymer layer, wherein the hydrophilic polymer layer is covalently bonded to the lens core layer, wherein the hydrophilic polymer layer includes a first macromer subpopulation including polyethylene glycol (PEG) and a second macromer subpopulation including polyacrylamide, wherein the first macromer subpopulation and second macromer subpopulations are cross-linked, wherein the hydrophilic polymer layer has a thickness of less than about 100 nm.

This and other embodiments can include one or more of the following features. The core can include a hydrogel. The core can include a silicone hydrogel. The lens core layer can include a rigid gas permeable lens material. The hydrophilic polymer layer can be attached to the core layer by a covalent linkage between an electrophilic reactive moiety and a second nucleophilic reactive moiety. The hydrophilic polymer layer can have a thickness less than about 1 micron. The hydrophilic polymer layer can include a thickness between about 1 nm to about 50 nm. The hydrophilic polymer layer can include a thickness less than about 50 nm. The hydrophilic polymer layer can include a thickness less than about 40 nm. The hydrophilic polymer layer can further include at least one active agent. The at least one active agent can be selected from the group consisting of a UV-absorbing agent, a visibility tinting agent, an antimicrobial agent, a bioactive agent, a leachable lubricant, a leachable tear-stabilizing agent, or any mixture thereof. The antimicrobial agent can include silver nanoparticles.

In general, in one embodiment, a coated soft contact lens includes a lens core including a polysiloxane with an equilibrium water content of less than about 2%, the lens core including an outer surface; and a hydrogel layer attached to at least a portion of the outer surface, wherein the hydrogel layer includes a hydrophilic polymer population of one or more species, wherein the lens is adapted for on-eye movement that is adequate to maintain the health of the ophthalmic surface and wearer comfort.

This and other embodiments can include one or more of the following features. The polysiloxane can be a cross-linked polysiloxane. The hydrophilic polymer population of one or more species can be at least partially cross-linked. The soft lens core can have an ionoflux diffusion coefficient of zero. The soft lens core can have an ionoflux diffusion coefficient of less than about 1×10−7 cm2/min. The hydrogel layer can be covalently attached to the outer surface of the lens core.

In general, in one embodiment, a contact lens includes a coated soft lens with an oxygen transmissibility (Dk/t) of greater than about 200, the coated soft lens includes a lens core with an outer surface and a coating, the coated lens adapted for on-eye movement that is adequate to maintain the health of the ophthalmic surface and wearer comfort.

This and other embodiments can include one or more of the following features. The lens can have an oxygen transmissibility of greater than about 300. The soft lens can include a hydrogel layer coating. The hydrogel layer can be covalently attached to an outer surface of the lens core. The lens core can include a cross-linked polysiloxane.

In general, in one embodiment, a contact lens includes a lens core including a polysiloxane having an outer surface and a hydrogel layer attached to at least a portion of the outer surface, wherein the hydrogel layer includes a hydrophilic polymer population of one or more species, wherein the lens has a thickness of less than about 50 microns, wherein the lens has a refractive index of greater than about 1.420.

This and other embodiments can include one or more of the following features. The lens can have a thickness of less than about 25 microns. The lens core can have a water equilibrium constant of less than about 1%. The lens can be a soft lens. The lens can have a thickness of less than about 75 microns. The lens can have a thickness of less than about 50 microns. The lens can have a thickness of less than about 25 microns. The core includes a sensor. The core includes a glucose sensor. The core includes a biometric sensor. The core can be adapted to measure one or more of temperature and heart rate. The core can include one or more of a conductive metal material, a camera, a power source, electronics, wireless transmitter, and memory. The lens can have an oxygen transmissibility (DK/t) of greater than 200. The lens can have an oxygen transmissibility (DK/t) of greater than 300. The lens core can have an elastic modulus of less than about 1.8 MPa. The lens core can have an equilibrium water content of less than about 1%. The lens core can have an equilibrium water content of less than about 0.5%. The hydrogel layer can include a thickness between about 1 nm to about 50 nm. The hydrogel layer or hydrophilic polymer layer can include a thickness less than about 50 nm. The hydrogel layer or hydrophilic polymer layer can include a thickness less than about 40 nm. The hydrogel layer or hydrophilic polymer layer can include a thickness below about 100 nm. The lens can have an advancing contact angle as measured by a captive bubble test of less than about 50 degrees. The lens can have an advancing contact angle as measured by a captive bubble test of less than about 35 degrees. The lens can have a critical coefficient of friction of less than about 0.05. The lens can have a water break up time of greater than about 20 seconds. The lens can deposit less than about 5 micrograms of protein per lens. Thee lens may not substantially denature proteins. The lens can denature less than about 5% of protein contacting the lens. The lens can deposit less than about 100 micrograms of lipid per lens. The hydrophilic polymer layer can further include at least one active agent. The at least one active agent can be selected from the group consisting of a UV-absorbing agent, a visibility tinting agent, an antimicrobial agent, a bioactive agent, a leachable lubricant, a leachable tear-stabilizing agent, or any mixture thereof. The antimicrobial agent can include silver nanoparticles. The lens can be adapted to provide adequate on eye movement while maintaining the health of the ophthalmic surface and wearer comfort.

In general, in one embodiment, a method of making a hydrogel coated contact lens includes reacting an outer surface of the contact lens with a first polymer species of a hydrophilic polymer solution, wherein the first polymer species includes a moiety at a first portion that forms a covalent attachment to the outer surface of the contact lens and reacting the first polymer species of the hydrophilic polymer solution with a second polymer species of the hydrophilic polymer solution, the second polymer species including a moiety that forms a covalent bond to a second portion of the first polymer species in a second covalent reaction thereby forming a hydrogel coating including the first polymer species and the second polymer species at least partially cross-linked.

This and other embodiments can include one or more of the following features. The covalent attachment between the outer surface of the contact lens and the first portion of the first polymer species can be formed by a first nucleophilic conjugate reaction. The second covalent reaction can be a second nucleophilic conjugate reaction. The partial cross-linking can be between an electrophilic moiety of the first species and a nucleophilic moiety of the second species in a nucleophilic conjugate reaction. The hydrophilic polymer population can include a first species selected from the group including polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer population can include a second species selected from the group consisting of: polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer population can include a first species including polyethylene glycol (PEG). The hydrophilic polymer population can include a second species including polyacrylamide. The first species can include a reactive electrophilic group or a reactive nucleophilic group and the second species can include a reactive electrophilic group or a reactive nucleophilic group complementary to the first species, the reactive electrophilic group and the reactive nucleophilic group can adapt to react to thereby form cross-links between the first species to the second species. The reactive electrophilic group can be selected from the group including amino-reactive groups, sulfhydryl-reactive groups, carboxyl groups, hydroxyl groups, haloalkyl groups, dienophile groups, aldehyde or ketone groups, alkenes, epoxides, and phosphoramidites. The reactive nucleophilic group can be selected from the group including amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites. At least one of the reactive electrophilic group of the first species or the reactive electrophilic group of the second species can be covalently linked to the outer surface of the contact lens. The contact lens can include a rigid gas permeable lens. The method can further include modifying an outer surface of a contact lens to form the plurality of reactive nucleophilic sites or a plurality of electrophilic sites on the outer surface. The modifying step can include exposing the outer surface of the contact lens to a gas plasma treatment. The method can further include adding a bifunctional monomer or a polymer to a prepolymerization mixture used to form the contact lens. The bifunctional monomer or polymer may not substantially change the optical properties of the contact lens. The bifunctional monomer or polymer can provide additional nucleophilic or electrophilic reactive sites on the surface of the contact lens. The method can further include modifying an outer surface of the contact lens. Modifying the outer surface of the contact lens can include one or more of: pH adjustment, plasma activation, light activation, activation of the liquid monomer mix, wet activation, and adding a monomer that reacts with the contact lens that still leaves reactive sites. Both of the first and second nucleophilic conjugate reactions can be Click reactions. The Click reaction can be a conjugate addition reaction. Both of the first and second nucleophilic conjugate addition reactions can be 1,4-nucleophilic addition reactions. The first and second nucleophilic conjugate addition reactions can be both Michael-type reactions. The reacting steps can be performed at a pH between about 5 and about 11. The contact lens can include a core consisting of polysiloxane. The contact lens can include a core including polysiloxane. The contact lens can include a core substantially free of polysiloxane. The contact lens can include a hydrogel core. The method can further include adding at least one active agent to the hydrogel coating. The at least one active agent can be selected from the group consisting of a UV-absorbing agent, a visibility tinting agent, an antimicrobial agent, a bioactive agent, a leachable lubricant, a leachable tear-stabilizing agent, or any mixture thereof. The antimicrobial agent can include silver nanoparticles. The hydrogel coated contact lens can have a thickness of less than about 50 microns. The hydrogel coated contact lens can have an oxygen transmissibility (DK/t) of greater than 200. The hydrogel coated contact lens can have an oxygen transmissibility (DK/t) of greater than 300. The contact lens can have an elastic modulus of less than about 1.8 MPa. The contact lens can have an equilibrium water content of less than about 1%. The hydrogel layer can include a thickness between about 1 nm to about 50 nm. The hydrogel layer can include a thickness less than about 50 nm. The hydrogel layer can include a thickness less than about 40 nm. The hydrogel layer can include a thickness below about 100 nm. The hydrogel coated contact lens can have an advancing contact angle as measured by a captive bubble test of less than about 50 degrees. The hydrogel coated contact lens can have an advancing contact angle as measured by a captive bubble test of less than about 35 degrees. The hydrogel coated contact lens can have a critical coefficient of friction of less than about 0.05. The hydrogel coated contact lens can have a water break up time of greater than about 20 seconds. The method can further include selecting one or more of reaction conditions, the first polymer species, and the second polymer species to achieve the properties.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4B show a reaction between a sulfonyl and thiol group.

FIGS. 9A-9D show more details of reactants and reactions depicted in FIG. 8.

FIGS. 13A-13T shows contact angles for exemplary lens.

FIGS. 14A-14J shows MATLAB code for contact angle calculation.

DETAILED DESCRIPTION

Figure 1A:
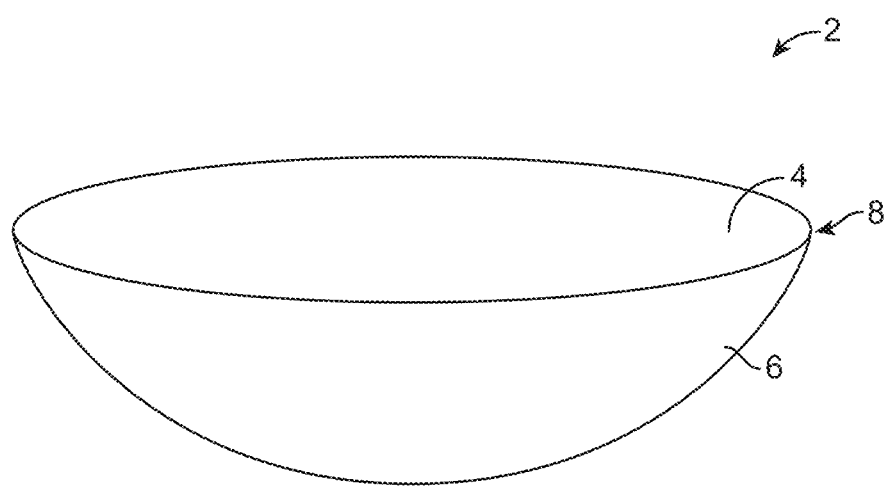
FIG. 1A shows a contact lens having a concave and convex surfaces.

As shown in FIG. 1A, a contact lens 2 may be generally understood as having a body with a concave surface 4 and a convex surface 6. The lens body may include a periphery or a perimeter 8 between the surfaces. The periphery may also include a circumferential edge between the surfaces.

The concave surface 4 may also be referred to as a posterior surface and the convex surface 6 may also be referred to as an anterior surface, terms that refer to respective position when worn by a user. In practice, the concave surface of the lens is adapted to be worn against or adjacent to an ophthalmic surface. When worn the concave surface may lie against a user's corneal surface 48 (see FIG. 2). The convex surface is outward-facing, exposed to the environment when the eye 40 is open. When the eye 40 is closed, the convex surface is positioned adjacent or against the inner conjunctival surface 44 of the eyelids 42 (see FIG. 2).

Because the convex and concave surfaces of a lens may be placed against or adjacent ophthalmic tissue such as the corneal surface, the properties of the surfaces can greatly affect a user's comfort and wearability of the lens as described above. For example, the lens may disrupt the tear film 16 of the eye 40 causing symptoms associated with dry eye. As such, embodiments described herein provide for a coated contact lens having a hydrophilic polymer layer applied on at least one of the lens's surfaces to improve the lens's wettability and wearability with minimal tear film disruption.

In one embodiment, the contemplated coated contact lens includes a core or bulk material with at least one surface having a hydrophilic polymer layer. In some cases, the hydrophilic layer is adapted for placement against an ophthalmic surface. The hydrophilic layer may cover a portion of the lens core surface. Alternatively, the hydrophilic layer may completely or substantially completely cover the core surface.

In other variations, more than one core surface has a hydrophilic layer. For example, both the concave and the convex surfaces of the lens may be coated by a hydrophilic polymer layer. Each hydrophilic layer on either concave or convex surfaces may independently completely or partially cover respective surfaces. In some cases the layer on each side of the core form a contiguous hydrophilic layer across both surfaces.

In additional variations, the hydrophilic polymer layer is formed from a cross-linked hydrogel polymer network having one or more cross-linked species. The hydrophilic polymer network may be partially cross-linked or substantially fully cross-linked. In some variations, the hydrophilic polymer is cross-linked to approximately 95% end group conversion. In some embodiments the one or more species are chemically cross-linked. In some embodiments the one or more species are ionically cross-linked. In some embodiments the one or more species are physically cross-linked. In some embodiments the one or more species can be cross-linked via a combination of chemical cross-linking, physical cross-linking, and ionic cross-linking.

Figure 1B:
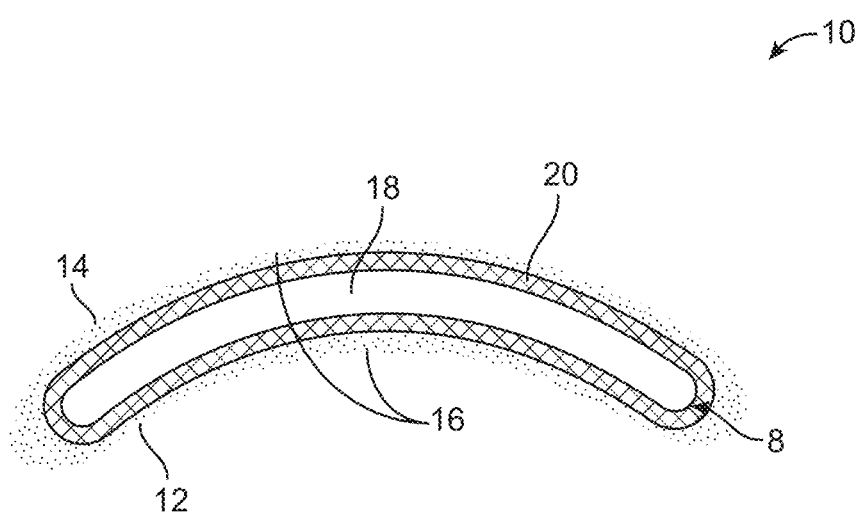
FIG. 1B is a cross-sectional view of an exemplary contact lens with a covalently attached cross-linked hydrogel layer.

Referring to FIG. 1B, a cross-section of an exemplary embodiment of a coated contact lens 10 is shown. Coated contact lens 10 includes a lens core 18 and a hydrophilic polymer layer 20 attached to the core 18. As shown, a hydrophilic polymer layer 20 surrounds the core 18. Both the concave and convex surfaces 12, 14 are coated by the same hydrophilic polymer layer 20 on both sides of the lens 18 with the hydrophilic polymer layer 20 extending to the peripheral edge 8 of the core 10. As shown, the outer hydrophilic layer 20 is substantially contiguous through or across a circumferential edge portion 18. A variety of different materials can be used as the lens core as described in detail below. In some embodiments the lens core can be a rigid gas permeable material. In some embodiments the lens core can be a hydrophobic materials, such as silicone. As used herein silicone includes polysiloxanes. In some embodiments the lens core can include a hydrogel.

Figure 2:
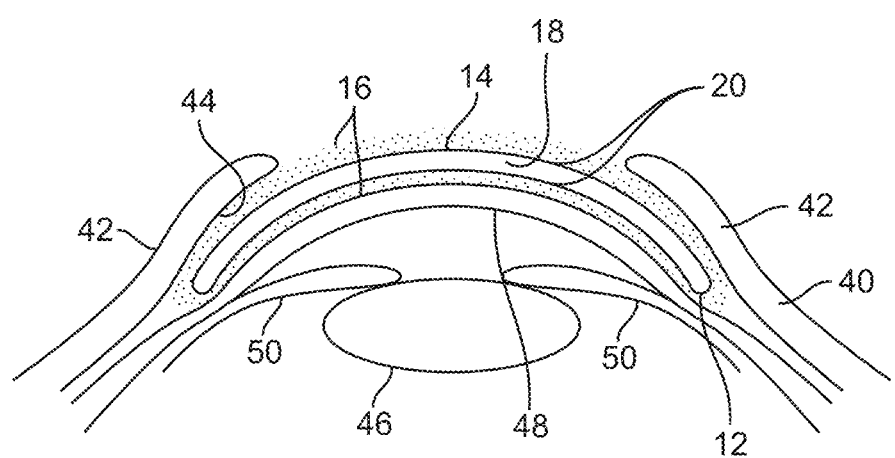
FIG. 2 is a cross-sectional view of the contact lens shown in FIG. 1B on the cornea.

Referring to FIG. 2, the coated contact lens 10 of FIG. 1B is positioned in a user's eye 40. The eye 40 is shown with eye lens 46 and iris 50. The concave surface 12 of the lens 10 is disposed and centered on the cornea. The convex surface 14 of the lens 10 is directed outwardly, facing the environment when the eye 40 is open. When the eyelid 42 close, the convex surface 14 is adjacent to the inner or conjunctival surface 44 of the eyelid 42. As the eyelids 42 open and close the conjunctival surface 44 slides across the convex surface 14 of the lens 10.

When placed on the cornea, the hydrophilic layer 20 of the contact lens 10 interacts with the natural tear film 16 of the eye 40. The contact lens 10 may be positioned within the tear film 16 and/or substantially reside within the aqueous layer of the tear film 16 that covers the eye 40. In some cases, the lens 10 is immersed in the tear film 16. The hydrophilic layer may be adapted to minimize disruption of the tear film by the contact lens.

A. HYDROPHILIC POLYMER LAYER

As used herein, the term "hydrophilic layer" or "hydrogel layer" may refer to a single continuous layer or various coated portions on the lens core.

Although shown in FIG. 1B as a single hydrophilic layer covering both sides of the lens core, it is to be appreciated that in some cases, only a portion of the lens (e.g. a single surface or a part of a surface) may be coated by a hydrophilic polymer layer. In some cases, the hydrophilic layer may only coat one of the core surfaces such as the concave surface. Moreover, the layer may not coat the entire area of the surface.

Additionally, other contemplated embodiments may include two or more noncontiguous hydrophilic polymer layers. For example, a first hydrophilic polymer layer may at least partially cover the concave surface while a second hydrophilic polymer layer may at least partially cover the convex surface. Unlike the embodiment depicted in FIG. 1B, the first and second hydrophilic polymer layer may not touch or share a boundary with one another.

In certain embodiments, the arrangement between the lens core and the surrounding hydrogel or hydrophilic layer may be understood as a layered structure with a hydrophilic polymer layer attached to an outer surface of a lens core layer. The hydrophilic polymer layer may be placed on either of the concave or convex surfaces. In some variations, the hydrophilic layer may only cover a portion of the lens core layer.

In other cases, the arrangement may include a first hydrophilic polymer layer on one side of the lens core layer, a second hydrophilic polymer layer on another side of the lens core layer. The core layer being a middle layer between the two hydrophilic polymer layers. The first and second layers may share a boundary (e.g. contiguous layers) or may form separate independent layers (e.g. noncontiguous layers).

In some cases, the layered arrangement a contact lens of the invention can be established by fluorescence analysis methods as described in Qui et al, U.S. Pat. Appl. Nos. 201200026457 and 201200026458.

Additionally, the hydrophilic layer may have relatively uniform dimensions, compositions, and mechanical properties throughout. Referring to FIG. 1B, the hydrophilic layer 20 has a substantially uniform thickness, water content, and chemical composition throughout the layer. In some embodiments, the hydrophilic layer has a substantially homogeneous composition and a substantially uniform depth and/or thickness.

As can be appreciated, uniformity is not required and may not be desirable for all situations. In some cases, a single layer may include portions having different characteristics including dimensions, composition, and/or mechanical properties. For example, a portion of the layer may have a different thickness than another portion, which may result in varying water content between the two portions.

Similarly, where two or more hydrophilic layers are used, the hydrophilic polymer layers may share or differ in any characteristics. For example, the core material may be asymmetrically layered with the hydrophilic polymer. The depth/thickness of the resulting hydrophilic polymer layers may vary between the layers on opposing sides of the lens substrate. This can result in, for example, different mechanical characteristics between the concave-cornea facing side of the coated contact lens and the outward facing convex face.

In some variations, the average thickness of the hydrophilic polymer layer may range between about 1 nm and about 500 nm. In some embodiments, the hydrogel layer comprises a thickness between about 1 nm to about 50 nm. In some embodiments the hydrophilic layer has a thickness of between about 50 nm to about 500 nm. In particular embodiments, the hydrophilic layer has a thickness of about 100 nm to about 250 nm. In some embodiments, the hydrogel layer comprises a thickness below about 100 nm. In some embodiments, the hydrogel layer comprises a thickness below about 50 nm. In some embodiments, the hydrogel layer comprises a thickness below about 40 nm.

In some embodiments, the thickness of the hydrophilic layer is between about 1 micron and about 200 microns, or between about 1 micron and about 100 microns, or between about 10 microns and about 200 microns, or between about 25 microns and about 200 microns, or between about 25 microns and about 100 microns, or between about 5 microns and about 50 microns, or between about 10 microns and about 50 microns, or between about 10 microns and about 35 microns, or between about 10 microns and about 25 microns, between about 1 micron and about 5 microns, or between about 1 micron and about 10 microns.

In other embodiments, hydrophilic layer has a thickness between about 0.01 microns and about 1 micron, or between about 0.01 microns and about 0.05 microns, or between about 0.05 microns and about 1 micron, or between about 0.02 microns and about 0.04 microns, or between about 0.025 microns and about 0.075 microns, or between about 0.02 microns and about 0.06 microns, or between about 0.03 microns and about 0.06 microns. In an exemplary embodiment, the hydrophilic layer has an average thickness of between about 0.01 microns and about 25 microns, or between about 0.01 microns and about 20 microns, or between about 0.01 microns and about 15 microns, or between about 0.01 microns and about 10 microns, or between about 0.01 microns and about 5 microns, or between about 0.01 microns and about 2.5 microns, or between about 0.01 microns and about 2 microns. In other variations, the hydrophilic layer has an average thickness from about 0.1 microns to about 20 microns, or from about 0.25 microns to about 15 microns, or from about 0.5 microns to about 12.5 microns, or from about 2 microns to about 10 microns.

In some embodiments the hydrophilic layer has a thickness of less than about 10 microns. In some embodiments the hydrophilic layer has a thickness of less than about 5 microns. In some embodiments the hydrophilic layer has a thickness of less than about 1 microns.

In further variations, the thickness or depth of the hydrogel layer may also be expressed in terms of the fold-multiple over a layer that could be represented as a molecular monolayer. In some embodiments, the hydrophilic layer has a thickness of that exceeds the nominal thickness of a molecular monolayer by at least five-fold. For example, in some cases the hydrophilic polymer layer is formed from PEG molecules that have a PEG monolayer radius of about 5 nm. The PEG containing hydrophilic polymer layer may have a thickness of about 50 nm, which results in a layer thickness or depth that is approximately 10-fold greater than the PEG monolayer radius.

Without limitation, the thickness of the anterior or posterior surface of a contact lens of the invention can be determined by Scanning Electron Microscopy, AFM or fluorescence microscopy analysis of a cross section of the contact lens in fully hydrated state as described herein. In an exemplary embodiment, the thickness of the anterior or posterior surface is at most about 30% (i.e., 30% or less), or at most about 20% (20% or less), or at most about 10% (10% or less) of the thickness of the inner layer (e.g. core) of the contact lens described in a fully hydrated state. In an exemplary embodiment, the layers forming the anterior and posterior surface of the contact lens described in this paragraph are substantially uniform in thickness. In an exemplary embodiment, these layers merge at the peripheral edge of the contact lens to completely enclose the inner layer of the silicon-containing layer.

Additionally, the hydrophilic layer may be understood to have a volume. In some cases, a first portion of the layer may have first volume V1 and a second portion of the layer may have a second volume V2. The volume may be calculated based on an estimated surface area of the layer. A total volume may also be understood to be the volume of a single hydrophilic layer (e.g. a layer covering the entire lens) or a sum of various layers with corresponding volumes.

Volume calculations may be based on an estimated surface area of approximately 1.25 square centimeters, on each side of the lens core. In some cases, the hydrophilic polymer layer has a volume in the range of about 15 nl to about 1.5 µl. In other variations, a volume range of about 15 nl to about 150 nl corresponds to an enveloping hydrophilic thickness range of about 50 nm to about 500 nm.

Additionally, in some variations, the hydrophilic layer may host an aqueous pool that includes a portion of the tear film pool volume. The total volume of the tear film is estimated to be about 4 µl to about 10 µl. For the purpose of the following calculation, consider an estimated of total tear film volume of about 7.5 µl. Accordingly, in some embodiments, the hydrophilic layer may host an aqueous pool that comprises about from about 0.2% to about 2% of the total tear film pool volume For water content of the hydrophilic layer, in some embodiments, the water content is between about 80% and about 98% water by weight. In other embodiments, the hydrophilic layer includes between about 85% and about 95% water by weight. Additionally, the water content of the hydrophilic layer may be expressed either by total water content or by a weight/volume percent. The polymer content of the hydrophilic layer may be described also by a weight/volume percent.

The hydrophilic layer may also include a hydrophilic polymer population having one or more subpopulations or species. In some cases, one or more species or subpopulations are cross-linked to form the hydrophilic polymer layer. The hydrophilic polymer layer precursors may be provided in a solution containing the cross-linkable material. Once cross-linked, the one or more species form the hydrophilic polymer coating.

In one variation, the hydrophilic layer includes a first polymer species and a second polymer species that are at least partially cross-linked together to form the hydrophilic layer. Additionally, the polymer species or subpopulation may include linear and/or branched components. A branched species may include a polymer having a branch count ranging from 2-arm to 12-arm branching. In other embodiments, the branched species may include starred branching with about 100 branches or more.

Figure 3A:
FIGS. 3A-3B show a first polymer species and a second polymer species with respective reactive groups A and N.
Figure 3B:
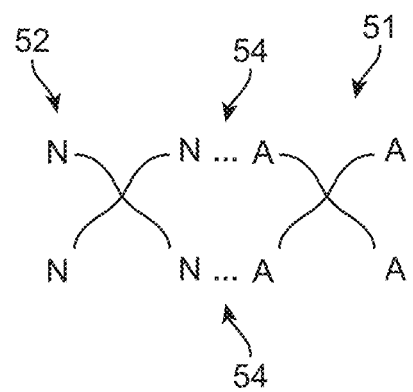

Referring to the FIG. 3A, a first branched polymer species 51 and a second branched polymer species 52 are schematically shown. The first branched polymer species 51 has four branch arms with reactive functional group A. The second branched polymer species 52 is shown having four branch arms with a reactive functional group N. In some embodiments, a reactive moiety A of the first polymer species 51 is adapted to react with a reactive moiety B of the second polymer species 52. The reaction between moieties A and B may form a covalent cross-link between the first and second polymer species. FIG. 3B depicts the first and second species 51, 52 cross-linked by an A-N moiety formed by a reaction between the reactive group A of the first polymer species and a reactive group B of a second polymer species. In some embodiments, the cross-linking action between one or more polymer and/or macromer species forms the hydrophilic polymer layer. For example, cross-linking one or more polymer species in a polymer solution may form a hydrogel with desirable characteristics for coating the lens core.

As can be appreciated, the cross-linking mechanism and/or reaction for a first and second polymer species may include any number of suitable methods known in the art including photochemical or thermal cross-linking. In some cases, cross-linking may occur through nucleophilic conjugate reaction, Michael-type reaction (e.g. 1,4 addition), and/or Click reaction between respective reactive groups on more than one polymer species in the hydrophilic layer.

Any suitable polymers may be used for the hydrophilic polymer population in the hydrophilic layer. In some cases, the polymer population includes species derived from polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), acrylic polymers such as polymethacrylate, polyelectrolytes, hyaluronic acid, chitosan, chondroitin sulfate, alginate, hydroxypropylmethylcellulose, and dextran.

In some embodiments the hydrophilic polymer population includes one or more species. Each of the one or more polymer species can be selected from polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), acrylic polymers such as polymethacrylate, polyelectrolytes, hyaluronic acid, chitosan, chondroitin sulfate, alginate, hydroxypropylmethylcellulose, and dextran.

In some embodiments the hydrophilic polymer population includes a first species comprising polyethylene glycol (PEG). The first species comprising PEG can be combined with a second polymer species selected from polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), acrylic polymers such as polymethacrylate, polyelectrolytes, hyaluronic acid, chitosan, chondroitin sulfate, alginate, hydroxypropylmethylcellulose, and dextran. In some embodiments the second species can comprise a second PEG species. In some embodiments the second species can comprise polyacrylamide.

In some embodiments the hydrophilic polymer population includes a species comprising polyacrylamide. The species comprising polyacrylamide can be combined with a second polymer species selected from polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), acrylic polymers such as polymethacrylate, polyelectrolytes, hyaluronic acid, chitosan, chondroitin sulfate, alginate, hydroxypropylmethylcellulose, and dextran. In some embodiments the second species can comprise a PEG species.

Additionally, any suitable reactive moieties may be used for the polymer species and subpopulations including reactive functional groups (e.g. reactive nucleophilic groups and electron pair acceptor) that react to form covalent linkages between polymer species or subpopulations to form the hydrophilic polymer layer described.

1. Reactive Functional Groups

Reactive functional groups and classes of reactions useful in covalent linking and cross-linking are generally known in the art. In some cases, suitable classes of reactions with reactive functional groups include those that proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfo-NHS esters, imidoesters, isocyanates, isothiocyanates, acylhalides, arylazides, p-nitrophenyl esters, aldehydes, sulfonyl chlorides and carboxyl groups.

NHS esters and sulfo-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components. Although unstable, Schiff bases are formed upon reaction of the amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., Biochemistry 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and imidazole groups. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:
(a) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to esters, ethers, aldehydes, etc.;
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) alkenes, which can undergo, for example, cycloadditions, acylation, Michael addition, etc;
(g) epoxides, which can react with, for example, amines and hydroxyl groups;
(h) phosphoramidites and other standard functional groups useful in nucleic acid synthesis and
(i) any other functional group useful to form a covalent bond between the functionalized ligand and a molecular entity or a surface.

d) Reactive Functional Groups with Non-Specific Reactivities

In addition to the use of site-specific reactive moieties, the present invention contemplates the use of non-specific reactive functional groups. Non-specific groups include photoactivatable groups, for example. Photoactivatable groups are ideally inert in the dark and are converted to reactive species in the presence of light. In one embodiment, photoactivatable groups are selected from macromers of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides may be preferable since they allow to employ less harmful photolysis conditions for the affinity component than unsubstituted arylazides.

In an exemplary embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., J. Org. Chem. 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde.

It is well within the abilities of a person skilled in the art to select a reactive functional group, according to the reaction partner. As an example, an activated ester, such as an NHS ester can be a useful partner with a primary amine. Sulfhydryl reactive groups, such as maleimides can be a useful partner with SH, thiol, groups.

Additional exemplary combinations of reactive functional groups found on a compound of the invention and on a targeting moiety (or polymer or linker) are set forth in Table

TABLE 1

| Chemical Functionality 1 | Chemical Functionality 2 | Linkage |
| --- | --- | --- |
| Hydroxy | Carboxy | Ester |
|  | Hydroxy | Carbonate |
|  | Amine | Carbamate |
|  | $SO_3$ | Sulfate |
|  | $PO_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl Thioether |
|  | Carboxy | Thioester |
|  | Carboxy | Amino amide |
|  | Mercapto | Thioester |
|  | Carboxy | Acyloxyalkyl ester |
|  | Carboxy | Acyloxyalkyl amide |
|  | Amino | Acyloxyalkoxy carbonyl |
|  | Carboxy | Anhydride |
|  | Carboxy | N-acylamide |
|  | Hydroxy | Ester |
|  | Hydroxy | Hydroxymethyl ketone ester |
|  | Hydroxy | Alkoxycarbonyl oxyalkyl |
| Amino | Carboxy | Acyloxyalkylamine |
|  | Carboxy | Acyloxyalkylamide |
|  | Amino | Urea |
|  | Carboxy | Amide |
|  | Carboxy | Acyloxyalkoxycarbonyl |
|  | Amide | N-Mannich base |
|  | Carboxy | Acyloxyalkyl carbamate |
| Phosphate oxygen ester | Hydroxy | Phosphate |
|  | Amine | Phosphoramidate |
|  | Mercapto | Thiophosphate ester |
| Ketone | Carboxy | Enol ester |
| Sulfonamide | Carboxy | Acyloxyalkyl sulfonamide |
|  | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, Prodrugs: Topical and Ocular Drug Delivery, K. B. Sloan, ed., Marcel Dekker, Inc., New York, 1992; for enol esters, see, March supra at 1160; for N-sulfonylimidates, see, Bundgaard et al., J. Med. Chem., 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. Annals NY Acad. Sci., 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., Protective Groups in Organic Synthesis, John Wiley & Sons, New York, 1991.

Generally, prior to forming the linkage between the compound of the invention and the targeting (or other) agent, and optionally, the linker group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Referring to FIG. 4A, in some embodiments, the reactive functional groups include thiol and sulfonyl moieties. The reactive nucleophilic group may be a thiol group adapted to react to a sulfonyl group that functions as an electron pair accepting moiety. Where a first polymer species contains a reactive thiol group and a second polymer species contains a reactive sulfonyl group, the cross-linkage between the first and second species may be formed through a thioether moiety (FIG. 4B). Although FIGS. 4A-4B illustrate the reaction with thiol and sulfonyl moieties, any of the reactive moieties described herein can be used to form the lenses described herein.

In other variations, one or more polymer species in the hydrophilic layer are covalently linked through a sulfonyl moiety such as, but not limited to, an alkylene sulfonyl moiety, a dialkylene sulfonyl moiety, an ethylene sulfonyl moiety, or a diethylene sulfonyl moiety. In further variations, one or more polymer species in the hydrophilic layer are covalently linked through a sulfonyl moiety and a thioether moiety, or an alkylene sulfonyl moiety and a thioether moiety, or a dialkylene sulfonyl moiety and a thioether moiety, or an ethylene sulfonyl moiety and a thioether moiety, or a diethylene sulfonyl moiety and a thioether moiety.

In further variations, the one or more polymer species in the hydrophilic layer are covalently linked through an ester moiety, or alkylene ester moiety, or an ethylene ester moiety, or a thioether moiety, or an ester moiety and a thioether moiety, or an alkylene ester moiety and a thioether moiety, or an ethylene ester moiety and a thioether moiety.

In some embodiments, the ratio of the reactive subpopulations in the hydrophilic polymer population is approximately 1 to 1. In other embodiments, the concentration of one of the subpopulations or species exceeds another species by about 10% to about 30%. For example, the concentration of a polymer species with an electron pair accepting moiety may exceed another polymer species with a reactive nucleophilic group.

Additionally, where the concentration of a first and second polymer species are approximately 1 to 1, the relative number of reactive moieties for each species may be approximately the same or different. For example, a polymer species may have more sites having an electron pair accepting moiety compared to the number of reactive sites on the other polymer species carrying the nucleophilic group. This may be accomplished, for example, by having a first branched polymer species having more arms with reactive electron pair accepting sites compared to a second polymer species carrying the nucleophilic moiety.

2. PEG-containing Hydrophilic Layer

In some embodiments, the polymers in the hydrophilic layer comprise polyethylene glycol (PEG). The PEG may include species that have a molecular weight of between about 1 kDa and about 40 kDa. In particular embodiments, the PEG species have a molecular weight of between about 5 kDa and about 30 kDa. In some embodiments, the hydrophilic polymer population consists of a species of polyethylene glycol (PEG). In other variations, the weight average molecular weight Mw of the PEG polymer having at least one amino or carboxyl or thiol or vinyl sulfone or acrylate moiety (as a hydrophilicity-enhancing agent) can be from about 500 to about 1,000,000, or from about 1,000 to about 500,000. In other embodiments, the hydrophilic polymer population comprises different species of PEG.

In some cases, the polymer includes subunits of PEG. In some variations, the subunits of the polymers of the PEG-containing layer of the contact lens are at least about 95%, or at least about 96%, or at least about 97%, or at least about 98%, or at least about 99% or at least about 99.5% polyethylene glycol.

In some cases, the water content of the PEG-containing hydrophilic layer is between about 80% and about 98% water by weight. In other embodiments, the hydrophilic layer includes between about 85% and about 95% water by weight.

The PEG-containing hydrophilic layer may include a PEG hydrogel having a swelling ratio. To determine swelling ratio, the PEG-hydrogel can be weighed immediately following polymerization and then immersed in distilled water for a period of time. The swollen PEG hydrogel is weighed again to determine the amount of water absorbed into the polymer network to determine the swelling ratio. The mass fold increase an also be determined based on this comparison before and after water swelling. In some embodiments, the PEG-containing layer has a mass fold increase of less than about 10%, or of less than about 8%, or of less than about 6%, or of less than about 5%, or of less than about 4%, or of less than about 3%, or of less than about 2%, or of less than about 1%. In some cases, the mass fold increase is measured by weighing the hydrogel when wet and then dehydrating it and weighing it again. The mass fold increase is then the swollen weight minus the dry weight divided by the swollen weight. For the hydrophilic layer as opposed to a bulk hydrogel, this could be accomplished by coating a non-hydrated substrate and then performing mass change calculations.

In another aspect, the invention provides for a hydrophilic layer with two cross-linkable PEG species. The first PEG species may include a reactive functional group adapted to react to another reactive functional on the second PEG species. Any of the described functional groups (e.g. previous section (A)(1)) may be suitable for forming a cross-linkage between the first and second PEG species.

In some cases, the first PEG species includes an electron pair accepting moiety and the second PEG species may include a reactive nucleophilic moiety. Once cross-linked through a reaction between the electron pair accepting and nucleophilic moieties, the PEG polymer network forms a hydrogel with a water content or concentration. The PEG hydrogel may serve as the hydrophilic layer coating a lens core to provide improved wettability, wearability, and/or reduced tear film disruption.

3. Hydrophilic Layer Formulations

In another aspect, the hydrophilic layer includes a first PEG species and a second species comprising polyacrylamide. The first PEG species may include a reactive functional group adapted to react to another reactive functional group on the second species comprising polyacrylamide. Any of the described functional groups (e.g. previous section (A)(1)) may be suitable for forming a cross-linkage between the first PEG species and second species comprising polyacrylamide.

In some cases, the first PEG species includes an electron pair accepting moiety and the second species comprising polyacrylamide may include a reactive nucleophilic moiety or vice versa. Once cross-linked through a reaction between the electron pair accepting and nucleophilic moieties, the PEG/polyacrylamide polymer network forms a hydrogel with a water content or concentration. The PEG/polyacrylamide hydrogel may serve as the hydrophilic layer coating a lens core to provide improved wettability, wearability, and/or reduced tear film disruption.

In some embodiments the first and second species are at least partially cross linked by a covalent reaction that is a second nucleophilic conjugate reaction.

In some embodiments the first and second species are at least partially cross-linked between an electrophilic moiety of the first species and a nucleophilic moiety of the second species in a nucleophilic conjugate reaction.

In some embodiments the first species comprises a reactive electrophilic group or a reactive nucleophilic group and the second species comprises a reactive electrophilic group or a reactive nucleophilic group complementary to the first species. The reactive electrophilic group and the reactive nucleophilic group are adapted to react to thereby form cross-links between the first species to the second species.

4. Active Agents

The hydrophilic polymer layer may include active agents such as any one or more of a medicinal agent, UV-absorbing agent, a visibility tinting agent, an antimicrobial agent, a bioactive agent, a leachable lubricant, a leachable tear-stabilizing agent, or any mixture thereof. In some embodiments silver nanoparticles can be used as an antimicrobial agent. The substances and materials may be deposited on the contact lenses to augment the interaction of a contact lens with the ocular region. These substances may consist of polymers, drugs, or any other suitable substance and may be used to treat a variety of ocular pathologies including but not limited to dry eye disease, glaucoma, corneal ulcers, scleritis, keratitis, iritis, and corneal neovascularization.

5. Interpenetration Polymer Network

The outer hydrogel network may also consist of interpenetrating polymer networks (or semi-interpenetrating polymer networks) formed in either simultaneous or sequential polymerization steps. For example, upon forming the initial outer hydrogel layer, the layer can be swollen in a monomer solution such as acrylic acid along with a crosslinker and initiator. Upon exposure to UV light, a second interpenetrating network will form. The double network confers additional mechanical strength and durability while maintaining high water content and high wettability.

B. LENS CORE

Any suitable contact lens may be used as a lens core for coating by the hydrophilic polymer layer described. For example, the lens core may be hydrophobic or hydrophilic. A hydrophilic core may have adequate water content but lack protein binding resistance that is imparted by the contemplated hydrophilic layer. A hydrophilic core would include a hydrogel containing core such as a pure hydrogel lens. For example, the core may contain Polyhexyethyl methacrylate lenses (pHEMA).

1. Rigid Gas Permeable Lens Core

In some embodiments the lens core is a rigid gas permeable (RGP) material. In some embodiments the rigid gas permeable material is non-hydrophilic. In some embodiments the rigid gas permeable material is hydrophobic. Examples of rigid gas permeable materials include: cellulose acetate butyrate, polyacrylate-silicone, non-hydrophilic silicone elastomers, polysiloxane, fluoro-silicon polymers, etc. As used herein silicone includes polysiloxanes. Examples of commercial RGP lenses that can be treated with the processes disclosed herein include the: Bausch & Lomb Boston Lens, Paragon CRT lens, Menicon Rose K, Menicon Lagado Flosi, Menicon Lagado Tyro, Menicon Lagado Onsi, Contamac Optimum Classic, Contamac Optimum Comfort, Contamac Optimum Extra, and Contamac Optimum Extreme. The hydrophilic coatings described herein can be formed on one or both of the convex and concave surfaces of the RGP core as described herein.

The rigid lens can be described based on the lens modulus. For example rigid lenses typically have a modulus of about 2000 MPa (2 GPa). In contrast a soft lens has a modulus on the order of about 2 MPa or less. In some embodiments a rigid lens core can be described as having an elastic modulus of greater than 500 MPa.

In some embodiments the rigid gas permeable material comprises fluorine. In some embodiments the rigid gas permeable material comprises a fluoro-acrylate. In some embodiments the lens core can be made of materials other than silicone and can be substantially free of silicone and polysiloxanes.

The water equilibrium content can be described as the amount of water absorbed by the lens or lens core at equilibrium. For example, the water equilibrium content can be determined by weighing the dehydrated lens core or lens, submerging the lens in water for several minutes, removing the lens from the water, and weighing the lens after being submerged in the water. The water equilibrium content can then be calculated by subtracting the dry weight of the lens from the weight of the lens after the water bath and dividing that value by the dry weight. The water equilibrium content can be expressed as a percentage.

In some embodiments the rigid gas permeable lens core has a water equilibrium content of less than about 5%. In some embodiments the rigid gas permeable lens core has a water equilibrium content of less than about 4%. In some embodiments the rigid gas permeable lens core has a water equilibrium content of less than about 3%. In some embodiments the rigid gas permeable lens core has a water equilibrium content of less than about 2%. In some embodiments the rigid gas permeable lens core has a water equilibrium content of less than about 1%. In some embodiments the rigid gas permeable lens core has a water equilibrium content of less than about 0.5%. In some embodiments the rigid gas permeable lens core has a water equilibrium content of less than about 0.1%.

In some embodiments the lens core includes a rigid gas permeable material with a soft coating, such as a coating comprising silicone or other soft material. RGP lenses having a soft outer coating are known as hybrid lenses. The soft coating can be on one or both of the convex and concave surfaces of the lens. The hydrophilic coatings described herein can be formed on one or both of the convex and concave surfaces of the hybrid RGP/soft coating core as described herein. Examples of commercial hybrid RGP lenses include those made by Synergeyes, such as the Synergeyes Duette Lens and the Synergeyes Ultra Health.

The RGP and hybrid RGP lenses are typically used by the patient for several months or more. In some cases the RGP and hybrid RGP lenses can be used for a year or more. In contrast to the soft lenses, which are disposable and used for shorter amounts of time, the RGP and hybrid RGP lenses can be exposed to harsher cleaning processes than the disposable soft lenses. In order to meet the design requirements for RGP lenses and hybrid RGP lenses it is desirable for any coatings to have a sufficiently long shelf life as well as the capability to withstand the more rigorous cleaning associated with those types of lenses. Alternatively, the coating may be regenerated multiple times throughout the wearing cycle by adding a reactive polymer solution to the lens care solution.

Hydrophilic layers, such as PEG were not considered to have good long term stability. In co-owned application Ser. No. 13/975,868 filed on Aug. 26, 2013, PEG layers formed on soft core lenses were analyzed with accelerated aging studies. The aging studies indicated that the PEG layers had better than expected shelf life and stability. The longevity of the coating with longer wear and more rigorous cleaning was unexpected. Additional testing has shown that the coating processes work well with RGP and hybrid RGP lenses. In addition the coatings have demonstrated a suitable shelf life for RGP and hybrid RGP lenses even with exposure to the more rigorous cleaning processes associated with those lenses. Additional details for the testing of the coatings through autoclave sterilization and accelerated aging tests are detailed in the examples.

2. Silicone Lens Cores

A suitable hydrophobic core includes a lens with high silicone content (e.g. high polysiloxane content). In some embodiments a lens core comprising silicone can be used with any of the hydrogel coatings described herein. The silicone lens core can comprise one or more polysiloxane compounds. In some embodiments the polysiloxanes are cross-linked.

In some embodiments the lens core can be primarily made of cross-linked polysiloxanes with trace impurities or trace additives. The lens core may consist substantially entirely of pure silicone (e.g. polysiloxane compounds), i.e. the core comprises about 100% silicone by weight. In other embodiments the lens core can be made out of only polysiloxanes (e.g. 100% silicone by weight). In some embodiments the lens core consists of polysiloxane. In other cases, the lens core, base, or substrate comprises about 10% to about 50% of silicone by weight. In some cases, the substrate or core comprises about 25% silicone by weight.

The silicone lens cores are resistant to water and do not adsorb water. The lack of absorption of water can be described as the water equilibrium constant. In contrast to hydrogels, which by definite absorb water, silicone does not appreciably absorb water.

In some embodiments the silicone lens core has a water equilibrium content of less than about 5%. In some embodiments the silicone lens core has a water equilibrium content of less than about 4%. In some embodiments the silicone lens core has a water equilibrium content of less than about 3%. In some embodiments the silicone lens core has a water equilibrium content of less than about 2%. In some embodiments the silicone lens core has a water equilibrium content of less than about 1%. In some embodiments the silicone lens core has a water equilibrium content of less than about 0.5%. In some embodiments the silicone lens core has a water equilibrium content of less than about 0.1%. In some embodiments the lens core is substantially free of water.

In some embodiments the lens core is a soft contact lens. For example, a soft contact lens can include an elastic modulus of less than about 2.0 MPa. In some embodiments the lens core has an elastic modulus of less than about 1.8 MPa.

Conventional silicone contact lenses are known in the art to stick to the surface of the eye and are unsuitable for use in adults without additional processing and treatments. An uncoated conventional silicone lens can stick to the eye and damage the surface of the eye if the lens is moved or removed. The hydrogel coatings described herein can be used to coat both sides of the silicone lenses to improve the lens properties and biocompatibility with the eye. The hydrogel coatings described herein can allow the coated silicone lens to adapt the lens for on-eye movement without damage to the eye or ophthalmic surface. The coated lenses described herein are adapted to provide adequate on eye movement while maintaining the health of the ophthalmic surface and wearer comfort.

Another advantage of a silicone lens core is the high refractive index of silicone. Conventional hydrogel lenses have a much higher water content. The water content decreases the overall refractive index of the lens. A thin silicone core with a high refractive index can be used with a thin hydrogel coating to produce a contact lens with smaller thickness than conventional lenses and a higher refractive index. In some embodiments the contact lens can have a refractive index of greater than about 1.420. The contact lens can have a thickness of less than 50 microns. In some embodiments the contact lens has a thickness of less than 25 microns.

The on-eye movement can also be expressed as ionoflux as described in U.S. Pat. Nos. 5,760,100 and 5,849,811, which also describe methods for determining the ionoflux. With a silicone core the ionoflux is very small since the silicone core would stick to the surface of the eye. In some embodiments the lens core has an ionoflux diffusion coefficient of zero. In some embodiments the lens core has an ionoflux diffusion coefficient of less than about $1\times10^{-7}$ cm2/min.

The silicone cores can be formed from and include a variety of different monomers. Examples of preferred silicone-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl](meth)acrylamide, N-[tris(dimethylethylsiloxy)silylpropyl](meth)acrylamide, N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy)methylsilyl)propyloxy) propyl)acrylamide; N,N-bis[2-hydroxy-3-(3-(bis(trimethylsilyloxy)methylsilyl)propyloxy)propyl]-2-methyl acrylamide; N,N-bis[2-hydroxy-3-(3-(bis(trimethylsilyloxy)methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl)propyloxy)propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy) propyl] acrylamide; N,N-bis[2-hydroxy-3-(3-(t-butyldimethylsilyl)propyloxy)propyl]-2-methyl acrylamide; N,N-bis[2-hydroxy-3-(3-(t-butyldimethylsilyl)propyloxy) propyl]acrylamide; 3-methacryloxy propylpentamethyldisiloxane, tris(trimethylsilyloxy)silylpropyl methacrylate (TRIS), (3-methacryloxy-2-hydroxypropyloxy)propylbis (trimethylsiloxy)methylsilane), (3-methacryloxy-2-hydroxypropyloxy)propyltris(trimethylsiloxy)silane, 3-methacryloxy-2-(2-hydroxyethoxy)-propyloxy)propylbis (trimethylsiloxy)methylsilane, N-2-methacryloxyethyl-O-(methyl-bis-trimethylsiloxy-3-propyl)silylcarbamate, 3-(trimethylsilyl)propylvinyl carbonate, 3-(vinyloxycarbonylthio)propyl-tris(trimethyl-siloxy)silane, 3-[tris(trimethylsiloxy)silyl]propylvinyl carbamate, 3-[tris(trimethylsiloxy)silyl]propyl allyl carbamate, 3-[tris(trimethylsiloxy) silyl]propyl vinyl carbonate, t-butyldimethyl-siloxyethyl vinyl carbonate; trimethylsilylethyl vinyl carbonate, and trimethylsilylmethyl vinyl carbonate). Most preferred siloxane-containing (meth)acrylamide monomers of formula (1) are N-[tris(trimethylsiloxy)silylpropyl]acrylamide, TRIS, N-[2-hydroxy-3-(3-(t-butyldimethylsilyl)propyloxy) propyl]acrylamide, or combinations thereof.

A class of preferred silicone-containing vinylic monomers or macromers is polysiloxane-containing vinylic monomers or macromers. Examples of such polysiloxane-containing vinylic monomers or macromers are monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); dimethacrylated or diacrylated polydimethylsiloxanes of various molecular weight; vinyl carbonate-terminated polydimethylsiloxanes; vinyl carbamate-terminated polydimethylsiloxane; vinyl terminated polydimethylsiloxanes of various molecular weight; methacrylamide-terminated polydimethylsiloxanes; acrylamide-terminated polydimethylsiloxanes; acrylate-terminated polydimethylsiloxanes; methacrylate-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxanylalkyl (meth)acrylic monomers; siloxane-containing macromer selected from the group consisting of Macromer A, Macromer B, Macromer C, and Macromer D described in U.S. Pat. No. 5,760,100 (herein incorporated by reference in its entirety); the reaction products of glycidyl methacrylate with amino-functional polydimethylsiloxanes; hydroxyl-functionalized siloxane-containing vinylic monomers or macromers; polysiloxane-containing macromers disclosed in U.S. Pat. Nos. 4,136,250, 4,153,641, 4,182,822, 4,189, 546, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); polysiloxane-containing macromers disclosed in U.S. Pat. Nos. 4,259,467, 4,260,725, and 4,261,875 (herein incorporated by reference in their entireties). Di and triblock macromers consisting of polydimethylsiloxane and polyalkyleneoxides could also be of utility. For example, one might use methacrylate end capped polyethyleneoxide-block-polydimethylsiloxane-block-polyethyleneoxide to enhance oxygen permeability. Suitable monofunctional hydroxyl-functionalized siloxane-containing vinylic monomers/macromers and suitable multifunctional hydroxyl-functionalized siloxane-containing vinylic monomers/macromers are commercially available from Gelest, Inc, Morrisville, Pa.

3. Silicone-Hydrogel (SiHy) Lens Cores

In another embodiment, the lens core may comprise a silicone-hydrogel (SiHy). The silicone hydrogel lens core can have a higher water content than the silicone lens core embodiments as hydrogels absorb water. For example, the silicone hydrogel lens core can have an equilibrium water content greater than 2% and less than 60%. In such cases, the SiHy lens core can be coated by the described hydrophilic polymer layers to improve wettability and wearability of the lens core. In other variations, the core comprises about 10% to about 50% of silicone by weight. In some embodiments the hydrophilic layer can be have a thickness of less than 100 nm.

In an exemplary embodiment, the silicone-containing layer or core of the coated contact lens is lotrafilcon, balafilcon, galyfilcon, senofilcon, narafilcon, omafilcon, comfilcon, enfilcon, or asmofilcon. In some cases, the silicone-containing core is NuSil Med 6755.

Alternatively, a non-silicone based core may be used as the substrate for coating. For example, an oxygen permeable lens made from a non-silicone material may also be coated with the described hydrophilic layer.

In an exemplary embodiment, the thickness of the core or core layer is from about 25 microns to about 200 microns, or from about 50 microns to about 150 microns, or from about 75 microns to about 100 microns, or from about 20 microns to about 80 microns, or from about 25 microns to about 75 microns, or from about 40 microns to about 60 microns.

C. ATTACHMENT OF HYDROPHILIC LAYER TO CORE

Another aspect of the invention provides for a coated contact lens with hydrophilic polymer layer that is covalently linked and attached to the core. The covalent linkage between the hydrophilic layer and the core may be understood to be a linking moiety that is covalently disposed between the lens core and the hydrophilic layer. In some cases, the linking moiety covalently attaches the hydrophilic layer to an outer surface of the lens core.

In some embodiments, the linking moiety may include any of the reactive functional groups described in at least section (A)(1). In further variations, the linking moiety may be a resultant moiety formed from a reaction between one or more of the reactive functional groups described in at least section (A)(1). For example, the linking moiety may include an electron pair accepting group such as a Michael-type Michael-Type electron pair accepter (e.g. sulfone group) on a polymer species in the hydrophilic layer that reacts to covalently attach the hydrophilic polymer layer to the core.

Figure 5A:
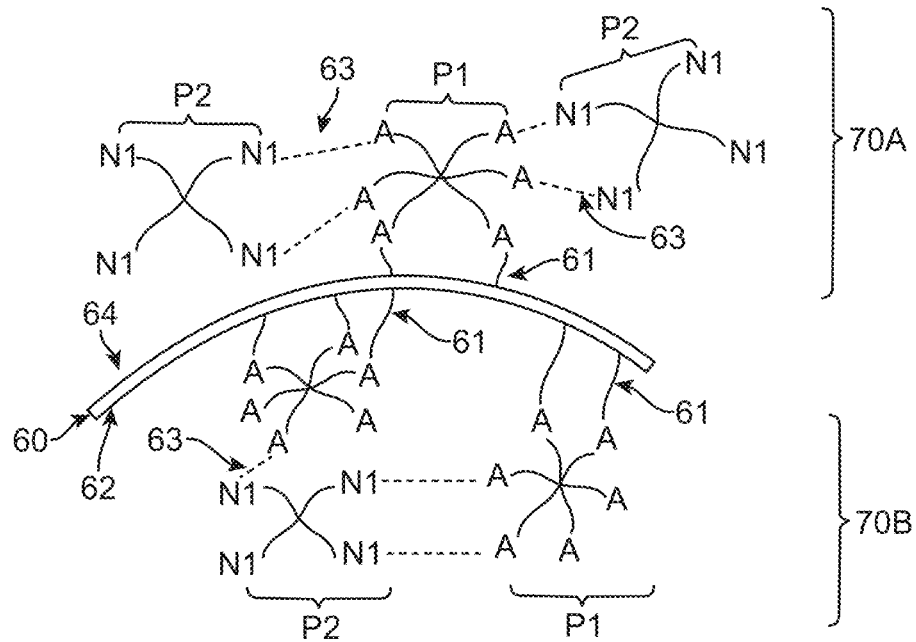
FIGS. 5A-5C show schematically a hydrophilic polymer having two species covalently attached to a lens core.
Figure 5B:
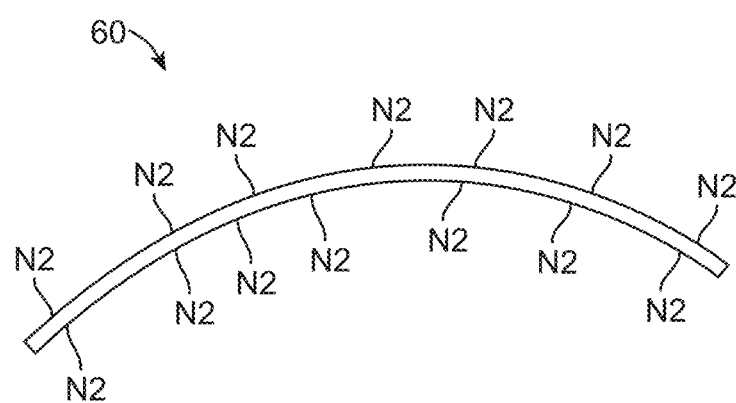
Figure 5C:
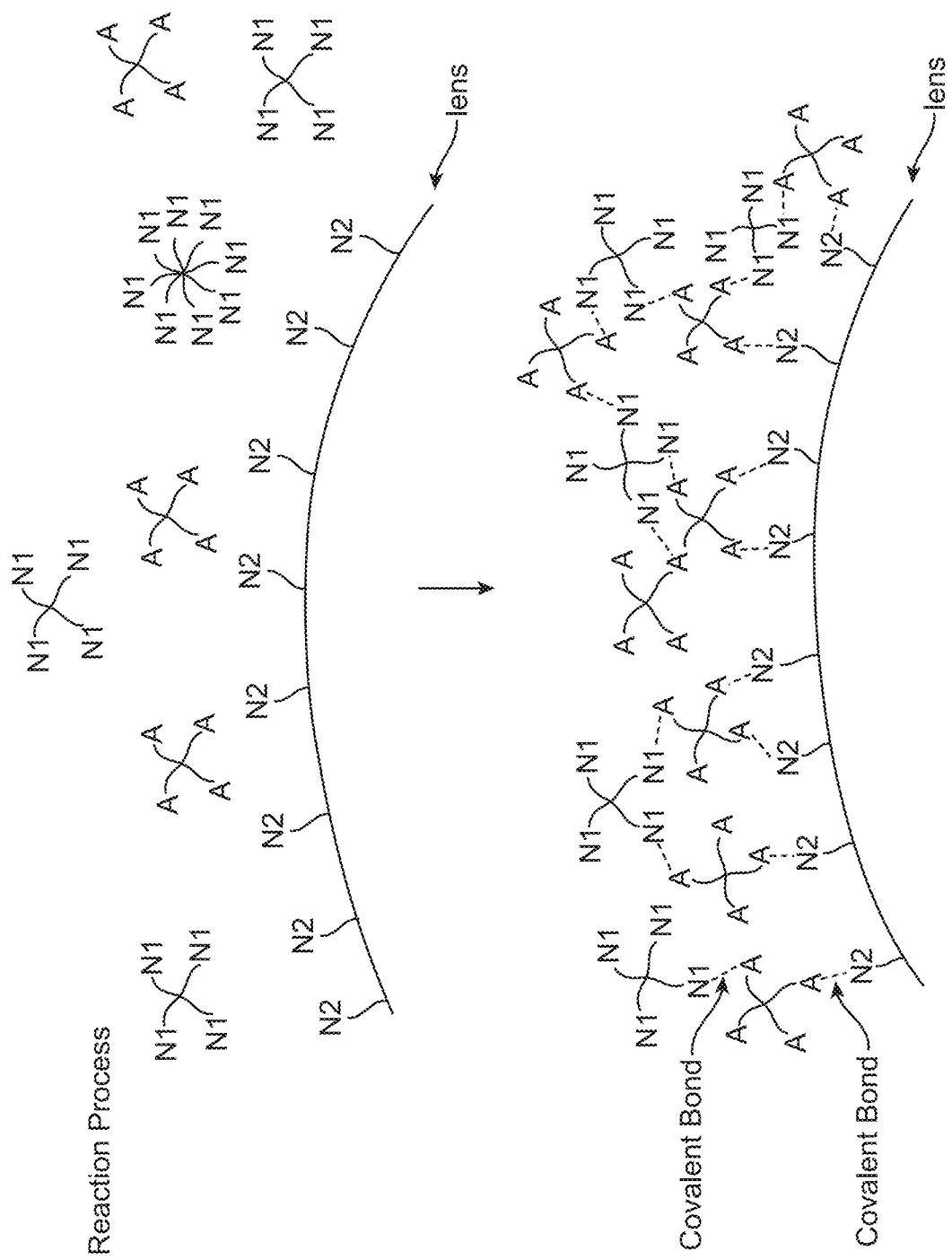

Advantageously, the hydrophilic polymer layer may be attached to the core through similar reactions utilized to cross-link the hydrophilic polymer layer. Referring to FIGS. 5A-5C, the hydrophilic polymer layer includes a first polymer species P1 having a reactive group A and second polymer species P2 with a reactive group N1. As described earlier, the hydrophilic polymer layer may be formed by cross-linking the first polymer species and the second polymer species through a reaction between reactive group A and N1. As shown in FIG. 5A cross-linkages 63 covalently link the first and second species to form the first hydrophilic polymer layer 70A on the convex surface 64 and the second hydrophilic polymer layer 70B on the concave surface 62 of the lens core 60.

Referring still to FIG. 5A, the first polymer species also forms a covalent linkage 61 with the outer surface of the core. As shown, the covalent linkage is formed through the reactive group A of the first polymer species P1 and the core surface. In some embodiments, the reactive group A on the first polymer species P1 reacts to (1) crosslink the polymer species in the hydrophilic polymer layer and (2) attach the formed hydrophilic polymer layer to the core. In such cases, this permits a first portion of the A moieties to react with the N1 moieties and a second portion of A moieties to react with the core surface. In some cases, the concentration of the first polymer species P1 and/or the number of available reactive A moieties of the first polymer species exceeds the corresponding concentration of the second polymer species and/or available reactive N1 moieties.

Referring to FIG. 5B, the lens core may include a reactive moiety N2. Reactive moiety N2 may be adapted to react with reactive groups of polymer species in the hydrophilic polymer layer. In some cases, the reactive moiety N2 only reacts to one of the polymer species. Referring to FIG. 5C, reactive moiety N2 reacts with reactive group A on the first species P1 to form a covalent attachment between the hydrophilic polymer layer and the core.

As can be appreciated, the reaction for attaching the hydrophilic polymer layer to the core may include any number of suitable methods known in the art including those described in at least section (A)(1). In some cases, covalent linking occurs through nucleophilic conjugate reaction, Michael-type reaction (e.g. 1,4 addition), and/or Click reaction between respective reactive groups on more than one polymer species in the hydrophilic layer. In some embodiments the first and second nucleophilic conjugate reactions are Click reactions. In some cases the Click reaction is a conjugate addition reaction. In some cases the conjugate addition reactions are 1,4-nucleophilic addition reactions. In some cases the conjugate addition reactions are both Michael-type reactions.

In some cases, the reactive A group is an electron pair acceptor and the reactive groups N1 and N2 are reactive nucleophilic groups. N1 and N2 may be the same or different reactive groups. Continuing with the example shown in FIGS. 5A-5C, the hydrophilic polymer layer is formed by a first reaction between the reactive A group and reactive nucleophile N1. Additionally, the hydrophilic polymer layer is covalently attached to the core through a second reaction between the reactive A group and nucleophile N2. The two reactions may occur simultaneously or near simultaneously in the same reaction vessel.

Where the reactive functional groups include thiol and sulfonyl moieties, the reactive A group may be a sulfonyl group on a first PEG macromer. The sulfone moiety functions as an electron pair accepting moiety on the first PEG macromer. The reactive nucleophiles N1 and/or N2 may be a thiol group (see FIG. 4A). For the first reaction, the first and second PEG macromers form a cross-link through the reactive thiol and sulfonyl groups, which can results in a thioether moiety (see FIG. 4B). Where the N2 nucleophile on the core is also thiol, a thioether may also be formed by a reaction between the sulfonyl moiety on the first PEG macromer and the N2 on the surface of the lens core.

As can be appreciated, the nucleophilic group (or other type of reactive group) on the core does not need to be the same as the reactive groups in the hydrophilic polymer layers. However, utilizing the same reactive groups may provide some advantages such as controllability and predictability of the respective reactions.

In other variations, the hydrophilic polymer layer are covalently linked to the lens core through a sulfonyl moiety such as, but not limited to, an alkylene sulfonyl moiety, a dialkylene sulfonyl moiety, an ethylene sulfonyl moiety, or a diethylene sulfonyl moiety. In further variations, the hydrophilic polymer layer is covalently attached to the core through a sulfonyl moiety and a thioether moiety, or an alkylene sulfonyl moiety and a thioether moiety, or a dialkylene sulfonyl moiety and a thioether moiety, or an ethylene sulfonyl moiety and a thioether moiety, or a diethylene sulfonyl moiety and a thioether moiety.

In further variations, the hydrophilic polymer layer is covalently attached to the core through an ester moiety, or alkylene ester moiety, or an ethylene ester moiety, or a thioether moiety, or an ester moiety and a thioether moiety, or an alkylene ester moiety and a thioether moiety, or an ethylene ester moiety and a thioether moiety.

In further embodiments, the linkage between the core lens and the hydrophilic layer is covalent, to the particular exclusion of any other form of chemical bond or association. For example, a hydrogel layer as described may be bound to the surface of a hydrophobic lens core by a chemical bond that consists of a covalent bond.

In some embodiments the hydrophilic polymer layer can be attached using one or more different polymer solutions. For example, a mixture of different polymer solution combinations can be used. Each of the different polymer solutions can be mixed prior to applying the solution to the contact lens. Each of the polymer solutions can include one or more polymer species. The one or more polymer species can have similar or complementary reactive groups to the surface modification of the lens or lens core. The one or more polymer species in each of the different polymer solutions can include different reactive groups and moieties. In some cases the different polymer solutions can each have unique polymer species with any of the reactive groups described herein. In some cases the different polymer solutions can have the same species but with different reactive groups. In some cases the different polymer solutions can share one polymer species and use additional different polymer species. In some embodiments two polymer solutions are used. In some embodiments three or more polymer solutions are used.

D. MULTI-LAYER CONTACT LENS

In some embodiments, the coated contact lens contemplated herein is a layered lens with a hydrophilic polymer layer on a silicone-containing layer. Some variations provide for a silicone-containing layer and a first polyethylene glycol-containing layer, wherein the first polyethylene glycol-containing layer and the silicon-containing layer are covalently attached to one another, and the contact lens has a layered structural configuration. In some embodiments the first polyethylene glycol-containing layer comprises PEG and polyacrylamide. In some embodiments the polyethylene glycol-containing layer comprises two or more species of PEG. In an exemplary embodiment, the contact lens does not comprise a second silicone-containing layer. In other embodiments, the contact lens does not comprise a second polyethylene glycol-containing layer. In another embodiment, the contact lens does not comprise either a second silicone-containing layer or a second polyethylene glycol-containing layer. In some embodiments the contact lens includes a second layer comprising polyacrylamide. In an exemplary embodiment, the contact lens comprises an anterior surface and a posterior surface wherein the anterior surface is the first polyethylene glycol-containing layer and the posterior surface is the silicone-containing layer. In an exemplary embodiment, the contact lens comprises an anterior surface and a posterior surface wherein the anterior surface is the silicone-containing layer and the posterior surface is the first polyethylene glycol-containing layer.

In an exemplary embodiment, the layer which forms the anterior surface and the layer which forms the posterior surface of the contact lens are of substantially the same thickness. In other cases, the layers may independently have any suitable thickness, including the thickness described above for either the hydrogel layer or the core.

In another aspect, the invention provides a contact lens comprising a silicone-containing layer, a first polyethylene glycol-containing layer and a second polyethylene glycol-containing layer, wherein the first polyethylene glycol-containing layer and the silicone-containing layer are covalently attached to one another, and the second polyethylene glycol-containing layer and the silicone-containing layer are covalently attached to one another, and the contact lens has a layered structural configuration. In an exemplary embodiment, the contact lens does not comprise a second silicone-containing layer. In an exemplary embodiment, the contact lens described does not comprise a third polyethylene glycol-containing layer. In an exemplary embodiment, the contact lens does not comprise either a second silicon-containing layer or a third polyethylene glycol-containing layer. In an exemplary embodiment, the contact lens comprises an anterior surface and a posterior surface wherein the anterior surface is the first polyethylene glycol-containing layer and the posterior surface is the second polyethylene glycol-containing layer. In an exemplary embodiment, the contact lens described in this paragraph comprises an anterior surface and a posterior surface wherein the anterior surface is the first polyethylene glycol-containing layer and the posterior surface is the second polyethylene glycol-containing layer and the first and second polyethylene glycol-containing layer are substantially identical to each other. In other cases, the first polyethylene glycol-containing layer has a composition, dimension, or other characteristic independent of the second polyethylene glycol-containing layer.

In an exemplary embodiment, for any of the contact lenses of the invention, the first polyethylene glycol layer and the silicone-containing layer are covalently attached through a sulfonyl moiety. In an exemplary embodiment, for any of the contact lenses of the invention, the first polyethylene glycol layer and the silicone-containing layer are covalently attached through an alkylene sulfonyl moiety. In an exemplary embodiment, for any of the contact lenses of the invention, the first polyethylene glycol layer and the silicone-containing layer are covalently attached through a dialkylene sulfonyl moiety. In an exemplary embodiment, for any of the contact lenses of the invention, the first polyethylene glycol layer and the silicone-containing layer are covalently attached through an ethylene sulfonyl moiety. In an exemplary embodiment, for any of the contact lenses of the invention, the first polyethylene glycol layer and the silicone-containing layer are covalently attached through a diethylene sulfonyl moiety. In an exemplary embodiment, for any of the contact lenses of the invention, the first polyethylene glycol layer and the silicone-containing layer are covalently attached through a thioether moiety.

In some embodiments the hydrophilic layer and the silicone-containing layer are covalently attached through a moiety with an amino group.

In an exemplary embodiment, for any of the contact lenses of the invention, the first polyethylene glycol layer and the silicone-containing layer are covalently attached through a sulfonyl moiety and a thioether moiety. In an exemplary embodiment, for any of the contact lenses of the invention, the first polyethylene glycol layer and the silicone-containing layer are covalently attached through an alkylene sulfonyl moiety and a thioether moiety. In an exemplary embodiment, for any of the contact lenses of the invention, the first polyethylene glycol layer and the silicone-containing layer are covalently attached through a dialkylene sulfonyl moiety and a thioether moiety. In an exemplary embodiment, for any of the contact lenses of the invention, the first polyethylene glycol layer and the silicon-containing layer are covalently attached through an ethylene sulfonyl moiety and a thioether moiety. In an exemplary embodiment, for any of the contact lenses of the invention, the first polyethylene glycol layer and the silicone-containing layer are covalently attached through a diethylene sulfonyl moiety and a thioether moiety.

In an exemplary embodiment, for any of the contact lenses of the invention, the second polyethylene glycol layer and the silicone-containing layer are covalently attached through a sulfonyl moiety. In an exemplary embodiment, for any of the contact lenses of the invention, the second polyethylene glycol layer and the silicone-containing layer are covalently attached through an alkylene sulfonyl moiety. In an exemplary embodiment, for any of the contact lenses of the invention, the second polyethylene glycol layer and the silicone-containing layer are covalently attached through a dialkylene sulfonyl moiety. In an exemplary embodiment, for any of the contact lenses of the invention, the second polyethylene glycol layer and the silicone-containing layer are covalently attached through an ethylene sulfonyl moiety. In an exemplary embodiment, for any of the contact lenses of the invention, the second polyethylene glycol layer and the silicone-containing layer are covalently attached through a diethylene sulfonyl moiety. In an exemplary embodiment, for any of the contact lenses of the invention, the second polyethylene glycol layer and the silicone-containing layer are covalently attached through a thioether moiety.

In an exemplary embodiment, for any of the contact lenses of the invention, the second polyethylene glycol layer and the silicone-containing layer are covalently attached through a sulfonyl moiety and a thioether moiety. In an exemplary embodiment, for any of the contact lenses of the invention, the second polyethylene glycol layer and the silicone-containing layer are covalently attached through an alkylene sulfonyl moiety and a thioether moiety. In an exemplary embodiment, for any of the contact lenses of the invention, the second polyethylene glycol layer and the silicone-containing layer are covalently attached through a dialkylene sulfonyl moiety and a thioether moiety. In an exemplary embodiment, for any of the contact lenses of the invention, the second polyethylene glycol layer and the silicone-containing layer are covalently attached through an ethylene sulfonyl moiety and a thioether moiety. In an exemplary embodiment, for any of the contact lenses of the invention, the second polyethylene glycol layer and the silicone-containing layer are covalently attached through a diethylene sulfonyl moiety and a thioether moiety.

In an exemplary embodiment, for any of the contact lenses of the invention, the first polyethylene glycol layer and the silicone-containing layer are covalently attached through an ester moiety. In an exemplary embodiment, for any of the contact lenses of the invention, the first polyethylene glycol layer and the silicone-containing layer are covalently attached through an alkylene ester moiety. In an exemplary embodiment, for any of the contact lenses of the invention, the first polyethylene glycol layer and the silicone-containing layer are covalently attached through an ethylene ester moiety. In an exemplary embodiment, for any of the contact lenses of the invention, the first polyethylene glycol layer and the silicone-containing layer are covalently attached through a thioether moiety.

In an exemplary embodiment, for any of the contact lenses of the invention, the first polyethylene glycol layer and the silicone-containing layer are covalently attached through an ester moiety and a thioether moiety. In an exemplary embodiment, for any of the contact lenses of the invention, the first polyethylene glycol layer and the silicone-containing layer are covalently attached through an alkylene ester moiety and a thioether moiety. In an exemplary embodiment, for any of the contact lenses of the invention, the first polyethylene glycol layer and the silicone-containing layer are covalently attached through an ethylene ester moiety and a thioether moiety.

In an exemplary embodiment, for any of the contact lenses of the invention, the second polyethylene glycol layer and the silicone-containing layer are covalently attached through an ester moiety and a thioether moiety. In an exemplary embodiment, for any of the contact lenses of the invention, the second polyethylene glycol layer and the silicone-containing layer are covalently attached through an alkylene ester moiety and a thioether moiety. In an exemplary embodiment, for any of the contact lenses of the invention, the second polyethylene glycol layer and the silicone-containing layer are covalently attached through an ethylene ester moiety and a thioether moiety.

E. CONTACT ANGLE

Advantageously, some of the contemplated coated contact lens provide for a hydrophilic polymer layer that has a population of hydrophilic polymers that are cross-linked with each other and, moreover, are as a whole, covalently attached to a lens core or layer. As such, the hydrophilic polymer layer can improve the wettability of the core contact lens.

As described in further detail below, the hydrophilicity or wettability of the hydrogel layer may be measured by a contact angle goniometer that implements a method known as a captive bubble contact angle test. Relatively high hydrophilicity is associated with a relatively low advancing contact angle.

In typical embodiments of the contact lenses according to the disclosed technology, when the lens is subjected to a bubble contact angle test, the lens shows an advancing contact in the range about 20° to about 50°. In some embodiments the lens has an advancing contact angle as measured by the captive bubble test of less than about 50 degrees. In more particular embodiments, the lens shows an advancing contact in the range about 25° to about 35°. In some embodiments the lens has an advancing contact angle as measured by the captive bubble test of less than about 35 degrees.

Figure 6A:
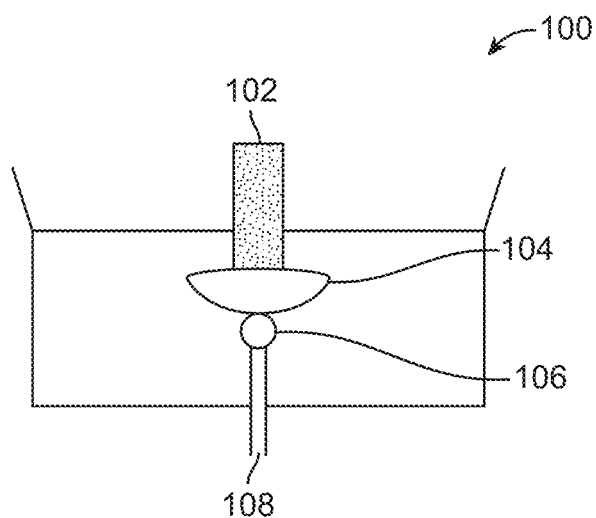
FIGS. 6A-6C show a captive bubble test.
Figure 6B:
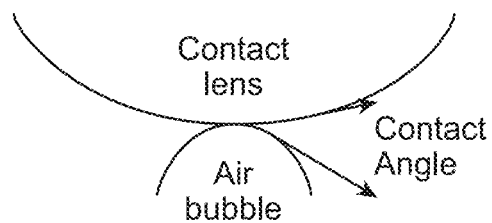
Figure 6C:
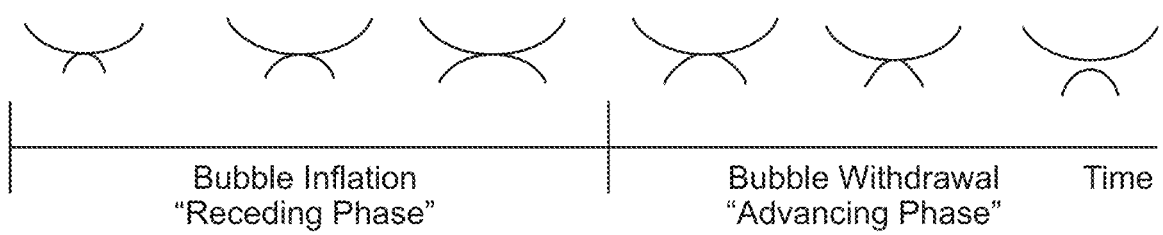

FIGS. 6A-6C show aspects of a captive bubble test that is commonly used in the contact lens industry as a surrogate measure of wettability or hydrophilicity of contact lenses, as provided by embodiments of the technology. FIG. 6A shows the setup 100 for a captive bubble test. The setup 100 includes a lens holding fixture 102 in communication with a test lens 104. An air bubble 106 is positioned at a surface of the test lens from a syringe pump 108.

FIG. 6B shows a schematic view of the contact angle as it occurs in an aqueous solution between the surface of a contact lens and an air bubble, as the air bubble is being inflated against or being withdrawn away from the contact lens.

FIG. 6C provides a schematic series of angles created as a bubble is being inflated against the contact lens surface, and then withdrawn. The left side of the drawing depicts the "receding phase" of the test; the right side of the drawing depicts the "advancing phase of the test. On the left, after the bubble first makes contact at what will be the central contact point between the bubble and the contact lens, the area of mutual contact expands, and the surrounding aqueous space recedes from the central contact point. Accordingly, this is termed the "receding phase". On the right, as the bubble is being withdrawn, the aqueous solution advances toward the central point of contact between the bubble and the contact lens. Accordingly, this is termed the "advancing phase" of the test. These profiles can be videographed during the test to capture the dynamics. In the recorded videos, software-based edge detection and angular separation techniques can be used to measure the receding and advancing angles at the interface of the bubble and lens.

In both the advancing and receding portions of the test, a small angle reflects the relatively high affinity of the contact lens surface for water, rather than air. Thus, there is an association between a small contact angle and hydrophilicity or wettability of the contact lens surface. In contrast, a large contact angle reflects a relative lack of affinity of the contact lens surface with water. By means of this test, the hydrophilicity of contact lens embodiments of the technology may be quantified.

In an exemplary embodiment, the contact lens having a hydrophilic polymer layer as described has an advancing contact angle of less than 20 degrees, or less than 25 degrees, or less than 30 degrees, or less than 35 degrees, or less than 40 degrees, or less than 50 degrees, or less than 60 degrees, or less than 70 degrees, or less than 80 degrees. In another embodiment, the advancing contact angle is between about 20 degrees and about 80 degrees, or between about 30 degrees and about 70 degrees, or between about 35 degrees and about 65 degrees, or between about 40 degrees and about 80 degrees, or between about 40 degrees and about 65 degrees, or between about 45 degrees and about 55 degrees, or between about 50 degrees and about 60 degrees, or between about 40 degrees and about 50 degrees. In some embodiments the advancing contact angle of the hydrophilic polymer layer is about 50 degrees plus or minus about 10 degrees.

FIG. 13 shows advancing contact angle data for commercial contact lenses coated with a coating comprising PEG as disclosed herein and as discussed in greater detail below.

F. OTHER COATED LENS PROPERTIES

The coated lenses described herein can be adapted to provide adequate on eye movement while maintaining the health of the ophthalmic surface and wearer comfort.

In some embodiments the hydrogel layer and core are substantially optically clear. In some embodiments the hydrogel layer is adapted to allow optical transmission through the hydrogel layer to the ophthalmic surface. In some embodiments the hydrogel layer substantially surrounds the outer surface of the lens core.

The thickness of the coated lens can be a measurement of the minor axis of the coated contact lens. In some embodiments the thickness of the core and coating is less than about 75 microns. In some embodiments the thickness of the core and coating is less than about 50 microns. In some embodiments the thickness of the core and coating is less than about 25 microns.

In some embodiments a first portion of the hydrogel layer comprises a first thickness different from a second thickness of a second portion of the hydrogel layer. The first portion of the hydrogel layer can include one or more polymer species described herein. The second portion can include one or more polymer species that are the same or different from the one or more polymer species in the first portion.

1. Critical Coefficient of Friction

The hydrogel coatings disclosed herein can reduce the critical coefficient of friction (CCOF) of the coated lens. In some embodiments the coated lens has a critical coefficient of friction of less than about 0.06. For example a silicone core can be coated with a hydrophilic polymer layer to decrease the critical coefficient of friction to less than about 0.06 or less than about 0.056. In some embodiments the coated lens has a critical coefficient of friction of less than about 0.05. In some embodiments the coated lens has a critical coefficient of friction of less than about 0.046. In some embodiments the coated lens has a critical coefficient of friction of less than about 0.045. In some embodiments the coated lens has a critical coefficient of friction of less than about 0.03. The CCOF can be measured using conventional techniques, such as described in Example 91.

2. Water Break Up Time

The hydrogel coated lenses described herein can result in a contact lens with an improved water break up time. The water break up time can be determined by removing a contact lens from a bath of saline and timing how long it takes for water film to break and recede across the surface of the lens, as described in Example 93. In some embodiments the water break up time for the coated lens is greater than about 25 seconds.

3. Protein Resistance

The hydrogel coated lenses described herein can result in a contact lens with an improved protein resistance. The improved protein resistance can make the lens more comfortable for the wearer.

One measure of the protein resistance is the amount of protein that is deposited on the lens during normal use. This can be measured as described in Example 92. In some embodiments the protein deposition is less than about 5 micrograms of protein per lens.

Another measure of protein resistance is the amount of protein that is denatured through contact with the lens. In some embodiments the hydrogel coated lenses described herein do not substantially denature proteins. In some embodiments the coated lenses described herein denature less than about 5% of protein contacting the lens.

4. Lipid Resistance

The hydrogel coated lenses described herein can result in a contact lens with an improved lipid resistance. The improved lipid resistance can make the lens more comfortable for the wearer.

One measure of the lipid resistance is the amount of lipid that is deposited on the lens during normal use. In some embodiments less than about 100 micrograms of lipid per lens is deposited on the lens during normal use. Lipid resistance is measured using an analogous method as described for protein resistance in Example 92.

4. Oxygen Transmissibility

The coated contact lenses described herein can have improved oxygen permeability. The improved oxygen permeability can be indicative of increased comfort for the wearer. One way to quantify oxygen permeability is with oxygen transmissibility (Dk/t). Conventional commercially available contact lenses have oxygen transmissibility values with a maximum in the mid-100s. Hydrogel lenses typically have oxygen transmissibility values around 25-50. The coated lenses disclosed herein can have improved oxygen transmissibility values. In some embodiments the coated lens has an oxygen transmissibility (Dk/t) of greater than 200. In some embodiments the coated lens has an oxygen transmissibility (Dk/t) of greater than 300. Oxygen permeability was measured as described in ISO 18369-4:2006 section 4.4.3 polarographic methods. The low water content lens has a higher transmissibility because oxygen solubility is 10 times higher in silicone than it is in water. The core lens with hydrogel coating configuration enables substantial increase in oxygen permeability.

5. Refractive Index

In some embodiments the contact lens can have a refractive index of greater than about 1.420. In other embodiments the contact lens can have a refractive index of greater than about 1.400. In other embodiments the contact lens can have a refractive index of 1.380. In other embodiments the contact lens can have a refractive index of 1.360.

6. Optional Devices Added to the Contact Lens

In some embodiments the coated contact lens can include one or more of: electronics, wiring, conductive material, sensors, a camera, power source, wireless transmitter, and memory. These materials can be within the lens core, within the hydrogel coating, or within both. In some embodiments the electronics or conductive materials are located within a water resistant core, such as a silicone core In some embodiments the core comprises a sensor. In some embodiments the core comprises a glucose sensor. In some embodiments the core comprises a biometric sensor. In some embodiments the core is adapted to measure one or more of temperature and heart rate of the wearer. In some embodiments the core comprises one or more of a conductive metal material, a camera, a power source, electronics, wireless transmitter, and memory.

G. METHODS OF MAKING A COATED CONTACT LENS OR MULTI-LAYERED CONTACT LENS

Another aspect of the invention provides for methods of making described coated and/or layered contact lenses.

In some embodiments, the method includes the steps of reacting a surface of a contact lens with a hydrophilic polymer solution. The hydrophilic polymer solution may contain one or more subpopulations or species that are adapted to react to form a coating on at least a portion of the contact lens. In some cases, the hydrophilic polymer solution reacts to form a cross-linked coating on the contact lens. The coating may be partially or substantially completely cross-linked. In some cases one or more of the species of the hydrophilic polymer solution can be covalently linked to the outer surface of the contact lens core.

The method for making the coated contact lenses described herein also include selecting reaction conditions to produce a coating and/or coated contact lens having any of the desired properties described herein. For example, one or more of the reaction conditions, first polymer species, and second polymer species can be selected to achieve any of the coating and coated lens properties described herein.

As shown in FIG. 3A, the hydrophilic polymer solution may include a first polymer species with a reactive group A and a second polymer species with a reactive group N. The hydrophilic polymer layer may be formed on the contact lens by reacting the reactive groups on the first and second polymer species to form the cross-linked hydrophilic polymer layer. As shown in FIG. 3B, the reactive groups A and N may form a covalent linkage 54 between the first and second polymer species to thereby cross-link the two species and result in a hydrophilic polymer layer. In some cases, the reaction between the first and second reactive groups on respective polymer species forms a hydrogel.

As described, any suitable reaction may be employed to form the hydrophilic polymer layer. These include (without limitation) nucleophilic conjugate reactions, Michael-type reactions (e.g. 1,4 nucleophilic addition reactions), and/or click reactions. In some cases, the reactive groups A and N are an electron pair accepting moiety and a nucleophilic moiety respectively, or vice versa.

Additionally, in some variations, the polymer species or subpopulation with in the hydrophilic polymer layer may include PEG species. In some cases, a first PEG species reacts with a second PEG species to form the hydrophilic polymer layer. For example, the first PEG species may include an electron pair acceptor adapted to react to a nucleophilic reactive moiety of a second PEG species to covalently link the PEG species. In some cases, a second species including polyacrylamide reacts with the first PEG species. For example, the first PEG species may include an electron pair acceptor adapted to react to a nucleophilic reactive moiety of a second polyacrylamide species to covalently link the PEG and polyacrylamide species.

Some embodiments provide for a covalent attachment between the hydrophilic polymer layer and the lens core or layer. For example, one or more of the polymer subpopulation or species within the hydrophilic polymer layer or solution may be adapted to react to the lens core to form a covalent attachment between the hydrophilic layer and the lens core. In some cases, the method of hydrophilic polymer layer attachment includes the step of reacting at least one of the polymer species with reactive sites on the surface of the core to form covalent bonds between the polymer species and the core surface.

Referring again to FIGS. 5A-5C, a first polymer species P1 may include a reactive group A that is adapted to react to a reactive group N2 of the core 60 surface. The reaction between the A and N2 groups results in a covalent linkage 61 between the first polymer species P1 and the core 60. As shown, the reactive group A may also be adapted to react with another reactive moiety N1 of a second polymer species P2 to form the hydrophilic polymer layer. As such, a first reaction between P1 and P2 forms the hydrophilic polymer layer and a second reaction couples the hydrophilic polymer layer to the core.

In some cases, the same reactive group A on the first polymer species P1 is capable of reacting to either the reactive moiety N1 or N2. In one variation, a first portion of the reactive A groups react to the N1 moiety and a second portion of the reactive groups react to the N2 moiety. In some embodiments, the first and second portions of the reactive A groups are on the same molecule of a polymer species. In further variations, the first and second portions of the reactive A groups are on different branch arms of the same polymer species. The dual reactions between P1 and P2, and P1 and core may occur in the same reactive vessel and during the same reaction time (or overlapping in some portion of the reaction time).

As described, any suitable reaction may be employed to form the hydrophilic polymer layer and attach the hydrophilic polymer layer to the lens core. These include (without limitation) nucleophilic conjugate reactions, Michael-type reactions (e.g. 1,4 nucleophilic addition reactions), and/or click reactions. For example, the plurality of reactions may all be nucleophilic conjugate reactions. Alternatively, the plurality of reactions may be different types of reactions.

In some embodiments, the first and second reactions are nucleophilic conjugate reactions, more particularly, both are 1,4-nucleophilic addition Michael-type reactions. By way of example, in some embodiments, the nucleophilic reactive moiety of the first macromer population comprises a thiol group and the electron pair accepting moiety of the second macromer population comprises a sulfone group.

In other embodiments of the method the first and second nucleophilic conjugate reactions may be described more broadly as a "Click" type reaction. Click reactions, as originally described by Karl Sharpless and others, refer to modular assembly of macromolecules that are typified as occurring in an aqueous environment, delivering high yield as a result of being driven to completion by large thermodynamic force, and creating substantially no byproducts, or byproducts that are non-toxic to biological systems. The click reactions are advantageous for application toward the manufacture of contact lenses because the lenses may be reacted in an aqueous solution, without toxic byproducts, rapidly, and to high yield.

Other examples of click type reactions that could be used to attach branched polymers in our immersive dip coating process including (a) general thiol-ene click reactions in general, (b) [3+2] cycloadditions, including the Huisgen 1,2-dipolar cycloaddition, (c) Diels-Alder reaction, (d) [4+1] cycloadditions between isonitriles (isocyanides) and tetrazines, (e) nucloephilic substitution especially to small strained rings like epoxy and aziridine compounds, (f) carbonyl-chemistry-like formation of ureas, and (g) addition reactions to carbon-carbon double bonds, such as involve dihydroxylation or the alkynes in the thiolyne reaction.

In a particular embodiment, the method of making the described coated lens includes the steps of reacting an outer surface of the contact lens with a first PEG species of a hydrophilic polymer solution, wherein the first PEG species comprises an electron pair accepting moiety and a first portion of the electron pair accepting moiety forms a covalent attachment to the outer surface of the contact lens through a first nucleophlic conjugate reaction; and reacting the first PEG species of the hydrophilic polymer solution with a second PEG species of the hydrophilic polymer solution, the second PEG species comprising a nucleophilic reactive moiety adapted to covalently link to a second portion of the electron pair accepting moiety of the first PEG species in a second nucleophilic conjugate reaction to thereby at least partially cross-link the first and second PEG species, wherein a PEG hydrogel coating is formed and covalently attached to the outer surface of the contact lens by the first and second nucleophilic conjugate reactions.

In some embodiments at least one of the reactive electrophilic group of the first species or the reactive electrophilic group of the second species is covalently linked to the outer surface of the lens core or contact lens.

In some embodiments the hydrophilic polymer layer is attached to the core layer by a covalent linkage between an electrophilic reactive moiety and a second nucleophilic reactive moiety.

In some embodiments the covalent attachment between the outer surface of the contact lens and the first portion of the first polymer species is formed by a first nucleophilic conjugate reaction.

In additional embodiments, the method includes activating a surface of the lens core. Activating the surface may form a plurality of chemically reactive sites on the surface. The reactive sites may be, for example, nucleophilic sites for reaction with a hydrophilic polymer.

Figure 7:
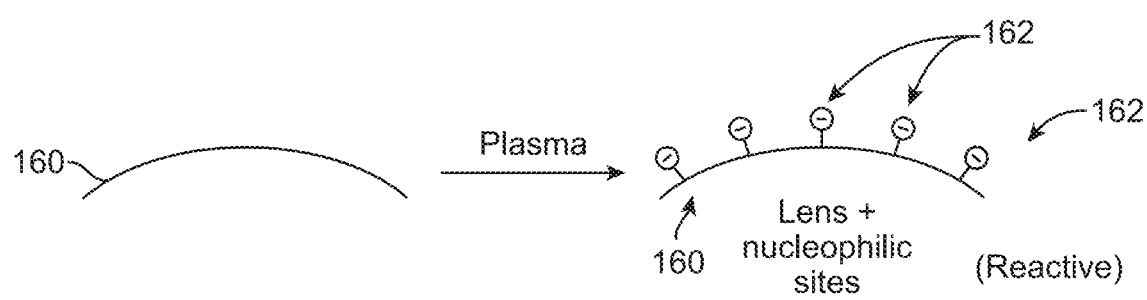
FIG. 7 shows an activated lens surface.

Referring to FIG. 7, a lens 160 without reactive sites is shown with a plurality of reactive sites 162 following an activation or modification process. In some cases, a plasma process is used to activate the surface of a core lens. The activation process may include the step of exposing the outer surface of the lens core to gas plasma. In some embodiments, the lens is transferred to a holding device, typically metal, and placed in a vacuum plasma chamber. The lens is plasma treated in an atmospheric plasma to form reactive sites on the surface. In some cases, an atmospheric plasma is applied to lens at 200 mTorr for about 3 minutes to thereby result in nucleophilic functional sites on the lens. In some embodiments, the lens are dehydrated prior to the plasma treatment.

In further variations, the contact lens surface may be activated through plasma treatment, preferably in oxygen or nitrogen gas. For example, the contemplated process may include activating a core material in a nitrogen plasma.

In some embodiments modifying an outer surface of the contact lens forms a plurality of reactive nucleophilic sites or a plurality of electrophilic sites on the outer surface.

In some embodiments modifying any other surface of the contact lens can be done by adding a bifunctional monomer or a polymer to a prepolymerization mixture used to form the contact lens. The bifunctional monomer or polymer does not substantially change the optical properties of the contact lens. The bifunctional monomer or polymer provides additional nucleophilic or electrophilic reactive sites on the surface of the contact lens.

In some embodiments modifying the outer surface of the contact lens includes adding a monomer that reacts with the contact lens surface but still leaves reactive sites after the reaction.

In other embodiments, activation of the contact lens surface can also occur through exposure to increasing pH's, for example solution pH of above 11.

In further embodiments, activation can also occur by modifying the monomer mix to include groups that are reactive to the branched hydrophilic coating polymers. Activation of the monomer mix can be a direct activation, or activation with a protected group that is cleaved, for example by light or changing pH. In other cases, plasma polymerization of functional silanes including mercapto and amino silanes may be used for activation. Additionally, plasma polymerization of allyl alcohol and allyl amine can also be used for activation.

In some embodiments, the core activation or modification step results in a reactive group N2 (shown in FIG. 5B) that is capable of reacting with at least one of the polymer species of the hydrophilic polymer layer. In some cases, at least one of the polymer species in the hydrophilic polymer layer reacts with a portion of the plurality of reactive sites on the core outer surface to form a covalent attachment between the hydrophilic polymer layer and the core surface. In some cases, the lens core is activated prior to the formation of the hydrophilic polymer layer on the core surface.

In some embodiments, the process of making the coated lens includes the step of reacting the activated core surface with a population of functionalized hydrophilic polymers. For example, the hydrophilic polymers may include a population of functionalized branched hydrophilic macromers with a first subpopulation functionalized with a nucleophilic reactive moiety and a second subpopulation functionalized with an electron pair accepting moiety. In further embodiments, the method may include reacting the functional moieties of two macromer subpopulations with each other in a first nucleophilic conjugate reaction to form covalent linkages between the two macromer subpopulations, thereby forming a cross-linked polymer network.

The method may also include reacting the electron pair accepting moieties of second macromer subpopulation and the nucleophilic moieties of the activated lens core surface in a second nucleophilic conjugate reaction to covalently attach the electron pair accepting moieties to the lens core surface. The first and second nucleophilic conjugate reactions, when complete, yield a contact lens that has a lens core with a cross-linked hydrophilic hydrogel layer covalently attached thereto.

As described, the first and second nucleophilic conjugate reactions may be of the same type with the reactions differing by having different reactants. The two reactions may involve the same electron pair acceptor, such as the hydrophilic polymer species comprising an electron pair accepter that can participate in a plurality of reactions. The plurality of reactions may differ by having distinct nucleophilically-reactive parent molecules, in one case, a hydrophilic polymer species with a nucleophilic moiety, and in the second case, a silicone-based polymer of the lens core with a nucleophilic moiety.

Figure 8:
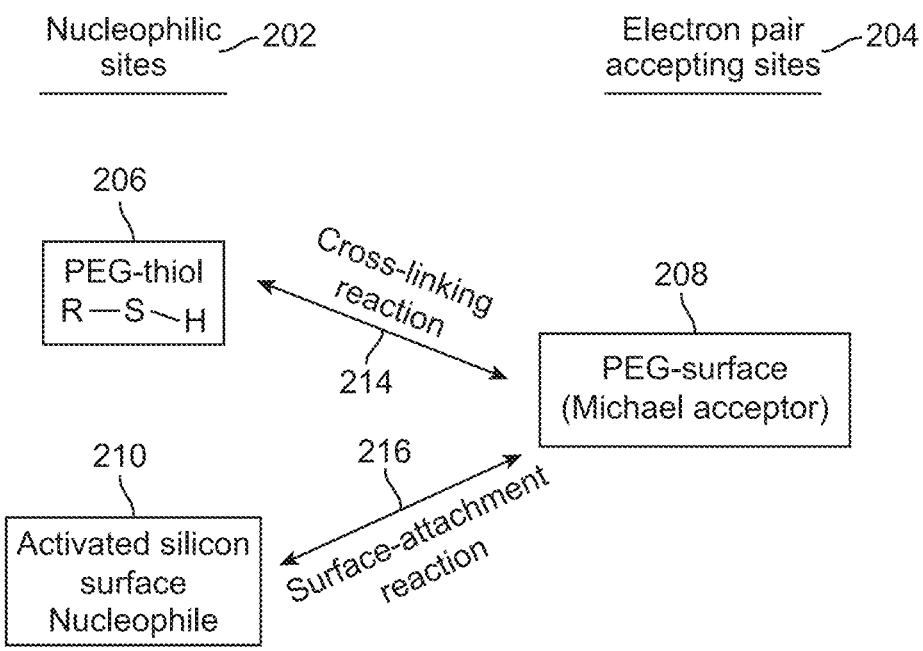
FIG. 8 is a schematic diagram of a first and second reaction with principal reactants.

Referring to FIG. 8, a schematic diagram 200 of two exemplary conjugate addition reactions 214, 216 and the principal reactants are shown. The principal reactants can be understood as nucleophilic moieties 202 and electron pair accepting moieties 204. In a first reaction, a reactant having nucleophilic functional moiety, such as PEG-thiol 206, reacts with a reactant having an electron pair accepting functional moiety 204, such as PEG-sulfone 204; the product of the reaction 214 is a linked pair of PEG molecules, linked by way of a central thioether bond. As the reaction proceeds among the functionalized PEG molecules, the PEG takes the form of a linked network, and inasmuch as a PEG network is hydrophilic, in an aqueous environment, the network takes the form of an integrated hydrogel.

In a second reaction 216, a reactant 204 having an electron pair accepting functional moiety, such as PEG-sulfone 204, reacts with a nucleophilic site on the surface of the silicone-based lens core 210; the product of this second reaction 216 is a covalent bond between the PEG-sulfone and the lens core. As above, inasmuch as the individual molecular that covalently link to the activated silicone-based core also are included as a constituent of a hydrogel structure, the hydrogel structure, as a whole, becomes covalently linked lens core.

Figure 9D:
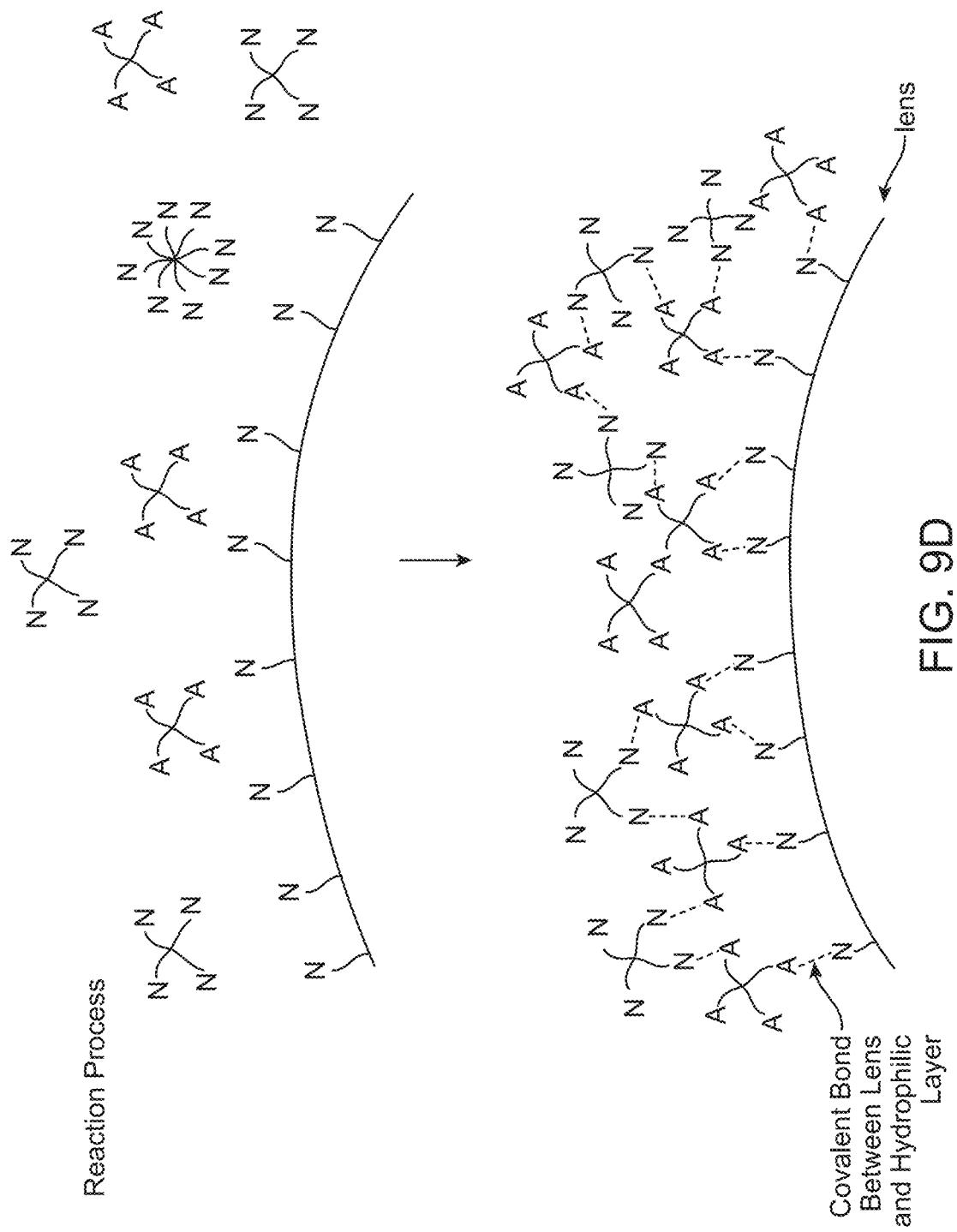

FIGS. 9A-9D show more detailed and particular aspects of reactants and reactions, as depicted schematically in FIG. 8. FIG. 9A shows a silicone-based lens core being activated by a plasma treatment to yield a lens surface covered with a bed of activated nucleophilic sites. FIG. 9B shows the structure of examples of reactants, including a PEG molecule, a Michael-Type electron acceptor such as a vinyl sulfone moiety, a nucleophile functional group such as a thiol, and the detail of the Michael type reaction itself.

FIGS. 9C-9D show a reaction process whereby two subpopulations of branched hydrophilic polymer species, a first subpopulation with a nucleophile functionality (N) and a second subpopulation with an electron pair accepting functionality (A) are in a reaction solution that bathes a nucleophilically activated (N) lens core. In the lower portion of FIG. 9D, per the first reaction as depicted in FIG. 8, reaction individual members of the two subpopulations have begun to link together by way of their functional groups, to form a hydrogel network. And, per the second reaction as depicted in FIG. 8, electron pair accepting moieties (A) of hydrophilic polymers engage in covalent linking with the nucleophilic sites on the lens surface, thereby covalently attaching the hydrogel network to the lens surface.

Figure 10A:
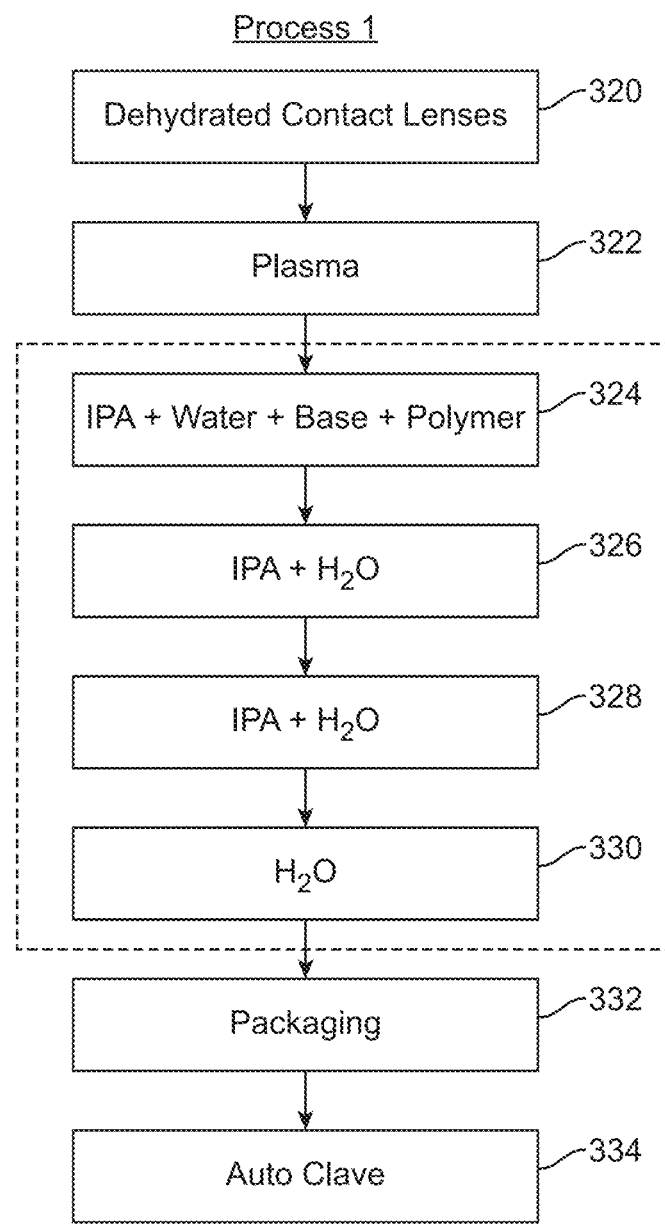
FIGS. 10A-10B are flow diagrams of exemplary methods described.
Figure 10B:
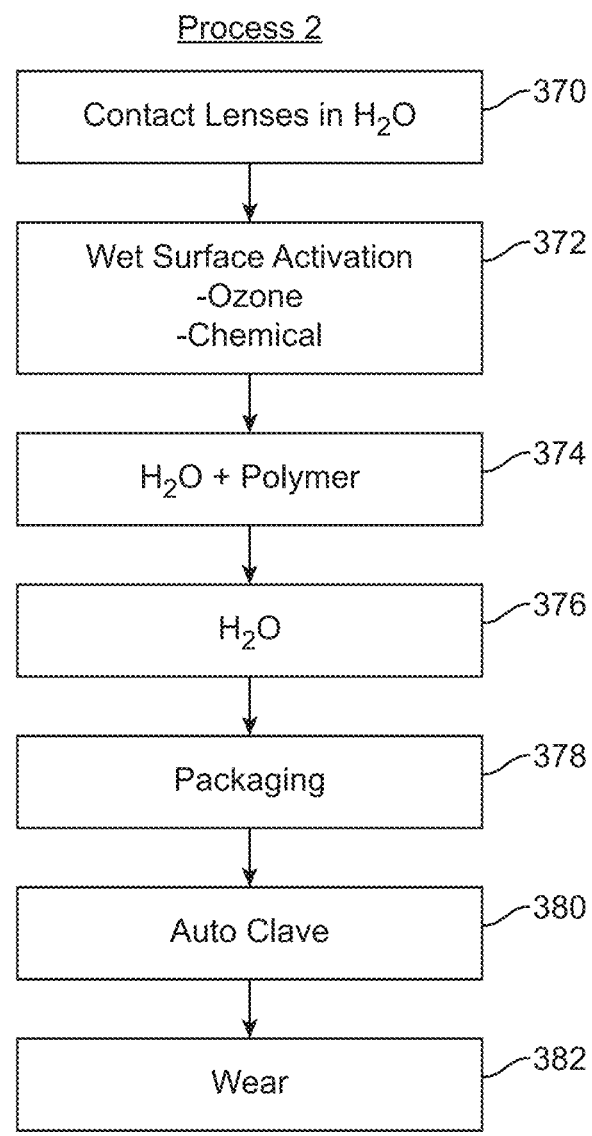

FIGS. 10A-10B provide flow diagrams of two variations of processes for making a contact lens with a covalently attached hydrogel membrane. FIG. 10A shows a process that includes a plasma activation method. Such plasma treatment may include exposure to any of an oxygen plasma or a nitrogen plasma. FIG. 10B shows a process that includes a chemical or "wet" activation method.

As described in FIG. 10A, a contact lens 320 plasma treated 324 to form a plurality of reactive sites on the contact lens. This may be accomplished by placing the lens into a vacuum plasma chamber. In some embodiments, the lens is transferred to a holding device, typically metal, and placed in a vacuum plasma chamber. The lenses are plasma treated in an atmospheric plasma at 200 mTorr for about 3 minutes, thereby creating nucleophilic functional sites on the lens. As described, the lens may be in a dehydrated state prior to the plasma treatment.

Referring still to FIG. 10A, after the lens core is activated, the activated lens core is placed into a solution that includes coating polymer and/or coating polymer species or precursors 324. The coating polymer may be any of the described hydrophilic polymers described including a hydrophilic polymer population including subpopulations of functionalized branched PEG species. In some cases, the solution also includes isopropyl alcohol and water. The solution may have a pH>7. The solution may be agitated to create a well-stirred bath and the lenses incubate in the solution for some period of time. In some cases, the incubation time is about 50 minutes.

Optionally, the coating process may include extraction steps to remove an unwanted component from the coated lens. For example, where a silicone-based lens core is used for a base or substrate, unreacted silicone molecules in the lens cores are extracted or diffused out of the lenses. Advantageously, the extraction process removes raw lens core material (e.g. raw silicone for a silicone-containing core) that may leach out of the lens into the ocular region. As such, further steps of the process may include transferring the lens to a solution of isopropyl alcohol and water for a period of time such as about 50 minutes 326 to continue extracting unreacted silicone molecules from the lens cores.

Additionally, as a second rinse 328, the lens may be transferred to a fresh solution of isopropyl alcohol and water for a period of time such as about 50 minutes to further extract unreacted silicone molecules from the lens cores. In some variations, the lens may also be transferred into a water bath 330 to equilibrate in water for a period of time (e.g. about 50 minutes).

Additionally, as shown in FIG. 10A, the lens may be transferred to a packaging container with a packaging solution 332. The lens may also be autoclaved 334. In some cases, the lens is autoclaved at about 250° F. for about 30 minutes.

FIG. 10B describes a wet-activation process for activating a lens core and coating the activated core. The process may begin with a lens in a hydrated state 370. The next step may include activating the hydrated surface lens core 372. This may be accomplished by a plasma or chemical treatment. For example, ozone may be used to activate the core surface. Once activated, the activated lens may be placed into a solution containing the coating material 374. The solution may include a hydrophilic polymer solution as described and water. In some cases, the solution is at a pH>7. The solution may be agitated to create a well-stirred bath and the lens incubates therein. In some cases, the lens incubates for about 50 minutes.

Next, the lens may be transferred to a water bath to equilibrate in water 376. The equilibration step may also serve to wash excess polymer from the lens. The lens may be equilibrated in water for about 50 minutes. The lens may be transferred to a packaging container with packaging solution 378. Additionally, as another step, the lens may be autoclaved. In some cases, the lens is autoclaved at about 250° F. for about 30 minutes. After the autoclave step, the resulting coated lens is ready for use 382.

Advantageously, the methods described herein provide for a cost-effective coating process that can be integrated with contact lens manufacturing processes currently employed in the industry.

Some embodiments of the method may be understood as an immersive method, wherein activated lens cores are immersed in a reaction solution within a stirred vessel, the solution including hydrophilic macromer reactants, and the reaction vessel operated to achieve appropriate reaction conditions. The reaction vessel and aspects of the conditions, in biochemical engineering terms, may be understood as occurring in a continuously stirred reaction tank (CSTR). In typical embodiments, the reacting steps occur within a reaction solution that has an aqueous solvent. Such the aqueous solvent may include any one or more of water, methanol, ethanol, or any suitable aqueous solvent that solubilizes PEG.

Figure 11A:
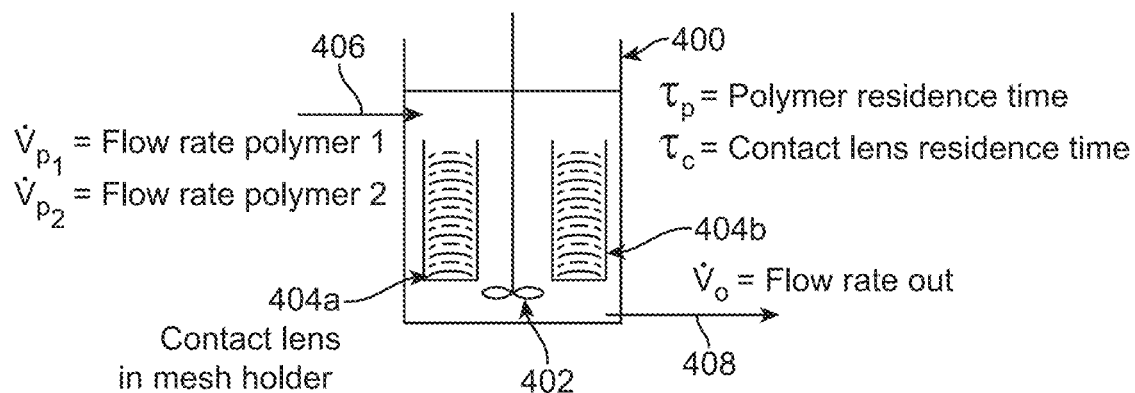
FIGS. 11A-11B show a schematic viewing of a continuously stirred tank reactor.

FIG. 11A provides a schematic view of a continuously stirred tank reactor (CSTR) 400 suitable for performing the reaction described. The CSTR 400 includes an agitator 402 for stirring the reaction contents within the tank. A feeding line or conduit 404 allows input or inflow 406 of reaction solutions including a hydrophilic polymer solution containing at least one polymer species. As shown, first and second polymer species flow into the CSTR 400. In some cases, the first and second polymer species have different flow rates VP1 and VP2 respectively. In other cases, the flow rates may be the same.

FIG. 11A shows a plurality of contact lenses 404a and 404b in the CSTR 400. In some cases, the contact lenses may be held in a mesh holder with openings or sufficient porosity to allow contact between the held lenses and the solution in the CSTR.

FIG. 11A also shows an output or outflow opening or conduit 408 for removing fluid from the CSTR 400. In some cases, the removed fluid is spent reaction fluid. The flow rate of the removed fluid may be designed as V0.

Figure 11B:
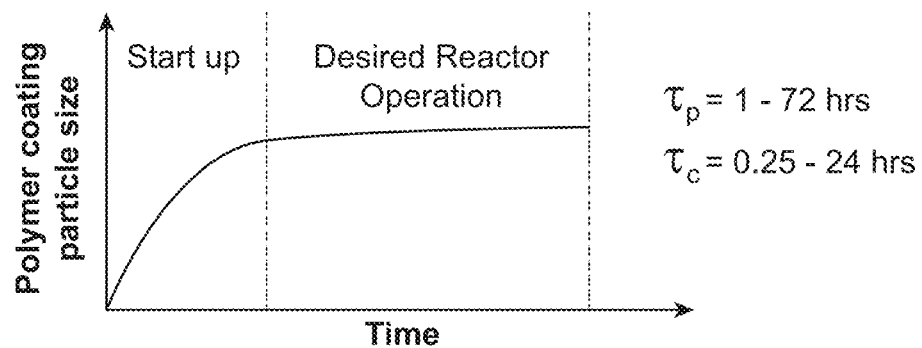

In some cases, Tp indicates the polymer residence time and TC indicates the contact residence time in the CSTR 400. FIG. 11B shows the relationship between polymer coating particle size as a function of time in a CSTR 400 where TP is 1-72 hours and TC is 0.25-24 hours.

In some variations, within the reaction solution, the total hydrophilic macromer concentration in the solution typically ranges between about 0.01 (w/v) % and about 0.50 (w/v) %. In some embodiments, the first and second macromer subpopulations are present in the solution at substantially equivalent concentrations. However, in other embodiments, the concentration of the reactive moiety of the second macromer subpopulation (an electron pair accepter) exceeds the concentration of the reactive moiety of first macromer subpopulation (a nucleophile).

Having an excess of electron pair reactive moieties with respect to the nucleophilic reactive moieties can be advantageous for the reactions included herein for the purpose of forming embodiments of hydrogel-coated contact lenses in that the electron pair accepting moieties of the hydrophilic polymer subpopulation so-functionalized can participate in two reactions. The polymer subpopulation functionalized with the electron pair acceptors participates (1) in covalent cross linking with the subpopulation functionalized with nucleophiles and (2) covalent attachment to nucleophilic sites on the silicone-based core lens surface. In contrast, the polymer subpopulation functionalized with a nucleophilic moiety engages only in the single reaction wherein it engages the polymer subpopulation functionalized with the electron pair accepting moiety.

The reactant concentration may also be appropriately expressed in terms of the relative concentrations of the reactive moieties of the participant macromers, rather than the concentrations of the macromers themselves. This follows from the possible variations in the degree to which the macromers are decorated with the function moieties that actually participate in the reactions. Accordingly, in some reaction embodiments, the concentration of the reactive moiety of the second macromer subpopulation exceeds the concentration of the reactive moiety of the first macromer subpopulation by at least about 1%. In more particular embodiments, the concentration of the reactive moiety of the second macromer subpopulation exceeds the concentration of the reactive moiety of the first macromer subpopulation by an amount that ranges between about 1% and about 30%. And in still more particular embodiments, the concentration of the reactive moiety of the second macromer subpopulation exceeds the concentration of the reactive moiety of the first macromer subpopulation by an amount that ranges between about 5% and about 20%.

Returning now to aspects of the reaction conditions, in some embodiments, the reacting steps are performed for a duration of between about 5 minutes and about 24 hours. In particular embodiments, the reacting steps are performed for a duration of between about 0.5 hour and about 2 hrs. In some embodiments, the reacting steps are performed at a temperature at a range between about 15° C. and about 100° C. In more particular embodiments, the reacting steps are performed at a temperature at a range between about 20° C. and about 40° C. In some embodiments, the reacting steps are performed at a pH between about 7 and about 11. In some embodiments, the reacting steps are performed at a pH between about 5 and about 11.

In some embodiments, the activated lens material is incubated in a dilute reaction solution containing 4-arm branched, 10 kDa PEG end functionalized with thiol groups, and 8-arm branched, 10 kDa PEG end functionalized with vinyl sulfone groups. The dilute solution contains between 0.01 and 0.5% total polymer, with a 10% excess of vinyl sulfone groups. The reaction can be performed in aqueous conditions, methanol, ethanol, or other solvents in which PEG is soluble. The reaction can be performed at a range of temperatures between about 15 degrees C. and about 100 degrees C. The reaction can be performed from between about 5 minutes and about 24 hours. The reaction can be performed at basic pH's, preferably in the range of 7-11.

As polymer reaction proceeds in the dilute solution, hydrogels (e.g. cross-linked hydrophilic polymer particles) are formed as branched polymers react with each other. Reaction progress can be monitored using dynamic light scattering techniques to measure hydrogel particle size and/or macromer aggregation level as the hydrogel network is forming. Temperature, pH, convection speed, and concentration will influence reaction rate and hydrogel particle size and formation rate. Hydrogel particles that are smaller than visible light will not cause optical distortions in the contact lens. Layer thickness can be regulated by monitoring hydrogel formation during the course of reaction.

In some variations, polyethylene glycol is the hydrophilic polymer. However, other multifunctional natural and synthetic hydrophilic polymers can also be used, for example poly(vinyl alcohol), poly(vinylpyrrolidinone), Poly(N-isopropylacrylamide) (PNIPAM) and Polyacrylamide (PAM), Poly(2-oxazoline) and Polyethylenimine (PEI), Poly(acrylic acid), Polymethacrylate and Other Acrylic Polymers, Polyelectrolytes, hyaluronic acid, chitosan, chondroitin sulfate, alginate, hydroxypropylmethylcellulose, and dextran.

In other embodiments, the methods include the step of forming a cross-linked hydrophilic polymer layer on a lens surface that is covalently attached to the contact lens. Covalent linkages between the branched hydrophilic polymers may occur due to Michael type nucleophilic conjugate addition reaction between vinyl sulfone and thiol and covalent linkages between the hydrophilic polymer and the lens surface occur due to conjugate addition reaction between vinyl sulfone and nucleophiles generated during the activation step. In some cases, reactivity of nucleophiles will increase with rising pH as molecules are increasingly deprotonated.

In further variations, any general Michael type reaction between enolates and conjugated carbonyls can also be used. For example, acrylate, methacrylate, or maleimide can be substituted for vinyl sulfone. Other examples include the Gilman reagent as an effective nucleophile for addition to conjugated carbonyls. The stork enamine reaction can be performed using enamines and conjugated carbonyls.

Additional covalent reaction mechanisms include hydroxylamine reaction with electrophiles such as aldehyde or ketone to produce oxime linkages.

Additional covalent reaction mechanisms include reaction of N-Hydroxysuccinimidyl esters with amines.

Additional covalent reaction mechanisms include isocyanates reaction with nucleophiles including alcohols and amines to form urethane linkages.

An additional embodiment provides for a method of forming a contact lens that includes casting of lenses in disposable soft molds. In some embodiments, a lens is coated in agar. This may be done by encapsulating the lens in a liquid agar solution. The agar is cooled and allowed to harden. After hardening, the encapsulated lens is removed from the agar, yielding an agar mold that includes a top piece, making the concave side of the lens, and a bottom piece matching the convex side of the lens. The mold is taken apart, a first drop of liquid hydrogel solution is added to the bottom half of the mold, followed by an activated lens core, followed by another drop of liquid hydrogel solution, followed the top half of the lens. The mold is then incubated until the hydrogel solidifies, then the contact lens is removed from the mold, yielding a lens with attached hydrophilic layers.

In some embodiments, a soft molding process employing agar is used. For example, Delrin plates may be machined with cavities (e.g. 12 cavities). To produce molds, agar may be melted and a small volume of liquid agar added to a mold cavity, followed by a lens, and then additional liquid agar to cover the lens. The mold may be refrigerated to solidify the agar. In some cases, the mold is refrigerated for about 20 minutes in the refrigerator to solidify the agar.

In further embodiments, a punch of the same diameter as the lens is used to punch around the lens. A small vacuum pick-up tool can then be used to remove the top of the mold, then a second vacuum pick-up tool can be used to remove the lens from the mold, and the top of the mold replaced. This process can yield trays of soft disposable molds with a cavity matching the lenses to be coated (the lenses used to make the molds may be the same type as the ones to be coated, but not the actually lenses that were ultimately coated).

To produce coated lenses, lens cores can be activated using one of the methods described above. The top of the agar lens mold may then be removed and hydrogel precursor solution (e.g. 10 µL) added to the bottom of the mold, followed by the lens core, followed by more of hydrogel precursor solution (e.g. 10 µL), followed by the lid of the mold. Forceps may be used to push the top of the mold down and remove any bubbles.

The tray of lenses can then be incubated. In some cases, the tray of lenses is incubated for 1 hour at 37° C. in order to polymerize the hydrogel. Following polymerization, the lenses may be removed from the molds and stored in PBS containing azide to prevent contamination.

To observe layer thickness, a small amount of fluorescein-maleimide may be added to the hydrogel layer on a coated lens. The fluorescein-maleimide reacts covalently with the hydrogel and enables the layer to be visualized using fluorescence microscopy.

In some cases, the coated lenses can be cut into 500 micron thick sections by striking 2 microtome blades held in parallel to cut the lens and leave a thin section between the blades. The lens cross section can be visualized using a fluorescent microscope (this is for a lens only functionalized with hydrogel on one side, the uncoated side serves as an internal control). In some cases, the average layer thickness was estimated to be about 25 microns based on this technique.

Additionally, the soft agar molds may be used to coated silicone hydrogel core lenses as well as coated pure silicone cores. Lenses can also be evaluated with the contact angle measurement technique described or any other suitable techniques.

In another embodiment, a PEG containing layer can be attached to a silicone containing lens layer using cast molding techniques. First, the silicone containing layer is modified to ensure surface groups are present that will react covalently with the PEG macromers. Second, molds are prepared that contain a top part and a bottom part in the same or similar shape as the silicone containing layer. The silicone containing layer is placed into the mold along with the liquid macromer PEG solution and the mold halves are placed together. The PEG can cure thermally for approximately 1 hour and the mold is taken apart.

The PEG containing layer can also be attached to the silicone containing layer using a dip coating method. First, the silicone containing layer is modified to ensure surface groups are present that will react covalently with the PEG macromers. For example, surface groups can be generated in a plasma treatment step, or by incubating in a basic solution, or by including reactive groups in the monomer mix. Next, a dip coating solution is prepared that consists of a dilute solution of reactive, branched, hydrophilic polymers. The activated lens is placed in the dip coating solution and incubated for 1-24 hours. Following incubation, the lens is rinsed thoroughly and then autoclaved in an excess volume of buffer solution prior to measuring captive bubble contact angles.

In alternative method, the hydrophilic polymer layer can be covalently attached to the silicone containing layer using another dip coating method. First, the silicone containing layer can be modified to create surface chemical moieties that are covalently reactive to the hydrophilic macromers. For example, surface groups can be generated in a plasma treatment step, or by incubating in a basic solution, or by including reactive groups in the monomer mix. Next, a dip coating solution can be prepared that consists of a dilute solution of reactive, branched, hydrophilic polymers. For example, the dilute solution can consist of a branched poly(ethylene glycol) end functionalized with vinyl sulfone and thiol in a solution containing 0.2M triethanolamine. The activated lens is placed in the dip coating solution and incubated for 1-24 hours at a temperature between about 20° C. and about 60° C. Following incubation, the lens is rinsed thoroughly and then autoclaved in an excess volume of phosphate buffered saline.

In an exemplary embodiment, the invention provides a method of making a contact lens described herein. The method comprises contacting an activated lens and a dip coating solution, thereby making a contact lens. In an exemplary embodiment, the method further comprises activating a lens, thereby creating an activated lens. A lens can be activated through a method known to one of skill in the art or a method described herein, such as plasma treatment or incubation in a basic solution, or by including reactive groups in the monomer mix. In an exemplary embodiment, the contacting takes place for between 1-24 hours, or from 1-12 hours, or from 12-24 hours, or from 6-18 hours. In an exemplary embodiment, the method further comprises rising the lens after the contacting step. In an exemplary embodiment, the method further comprises autoclaving the lens after the contacting step. In an exemplary embodiment, the method further comprises autoclaving the lens after the rinsing step.

In another embodiment, an alternative method of forming a contact lens includes a spray coating approach wherein a reactive ultrasonic spray coating is used to coat substrates with a thin, adhered layer of cross-linked hydrogel. A two-component hydrogel, comprising branched PEG end-capped with vinyl sulfone, and branched PEG end-capped with thiol, was used to produce the cross-linked thin films. The two components are simultaneously dripped onto an ultrasonic spray nozzle where they are combined and atomized into small droplets, which then are accelerated to the substrate in an air sheath. The rate of reaction is adjusted to ensure that reaction is fast enough that a solid structure forms on the surface, but slow enough that the components do not instantly polymerize upon mixing at the nozzle.

In some embodiments a multi-layer contact lens is provided. The contact lens includes a lens core layer covered by an outer hydrophilic polymer layer. The hydrophilic polymer layer is covalently bonded to the lens core layer. The hydrophilic polymer layer includes a first macromer subpopulation comprising polyethylene glycol (PEG) and a second macromer subpopulation comprising polyacrylamide. The first macromer subpopulation and second macromer subpopulations are cross-linked. The hydrophilic polymer layer has a thickness of less than about 100 nm. In some embodiments the lens core is a hydrogel. In some embodiments the lens core is a silicone hydrogel. In some embodiments the lens core is a rigid gas permeable lens material.

In some embodiments a contact lens is provided. The contact lens includes a coated soft lens with an oxygen transmissibility (Dk/t) of greater than about 200. The coated soft lens includes a lens core with an outer surface and a coating. The coated lens is adapted for on-eye movement that is adequate to maintain the health of the ophthalmic surface and wearer comfort.

An alternative spray method, considered appropriate for scaled manufacturing, is ultrasonic spray coating, a technique that enables precise, thin film coatings. It has been employed previously for stents and in the microelectronics industry, and is currently used in several high volume manufacturing lines. A state of the art Sonotek instrument was used to form coated contact lens prototypes. This technology enables 3D printing, thus potentially providing a platform for constructing complicated lens structures with integrated sensors or electronics.

The Sonotek instrument has an ultrasonically driven spray nozzle with two feed lines that deposit solution onto the tip. A two-component hydrogel system involves dissolving the PEG vinyl sulfone component in methanol containing triethanolamine (TEOA; acting as an organic base) and the PEG thiol component in pure methanol. The two solutions are delivered to the nozzle tip at a rate of 5 microliters per minute and the concentration of each PEG component is adjusted such that equal volumes of each component mix to achieve a 10% molar excess of vinyl sulfone groups. When the solutions are deposited on the ultrasonic tip, they mix and are atomized into droplets that are approximately 20 microns in diameter. A pressured air sheath then accelerates the droplets onto the surface to be coated. By including FITC-malelimide in the PEG vinyl sulfone component, mixing and crosslinking that result in film deposition can be films. A concentration of TEOA and identified that at a molar ratio of TEOA:SH of 6:1 could deposit a uniform cross-linked hydrogel on a variety of substrates, including pure silicone and silicone hydrogel core lenses. An alternative aqueous spray coating method was also tested and was shown to be feasible, however for the contact lens substrates, the methanol process advantageously produces a highly uniform film of ~5 microns. The contact angle measurements on coated lenses demonstrated the integrity of the deposited film.

Figure 12A:
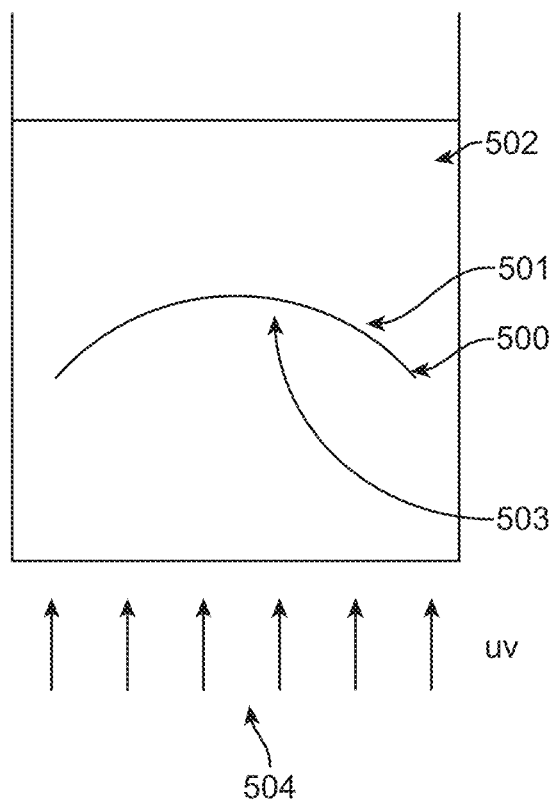
FIGS. 12A-12B show a method of producing lenses with bilateral hydrogel layers differing in depth or composition.
Figure 12B:
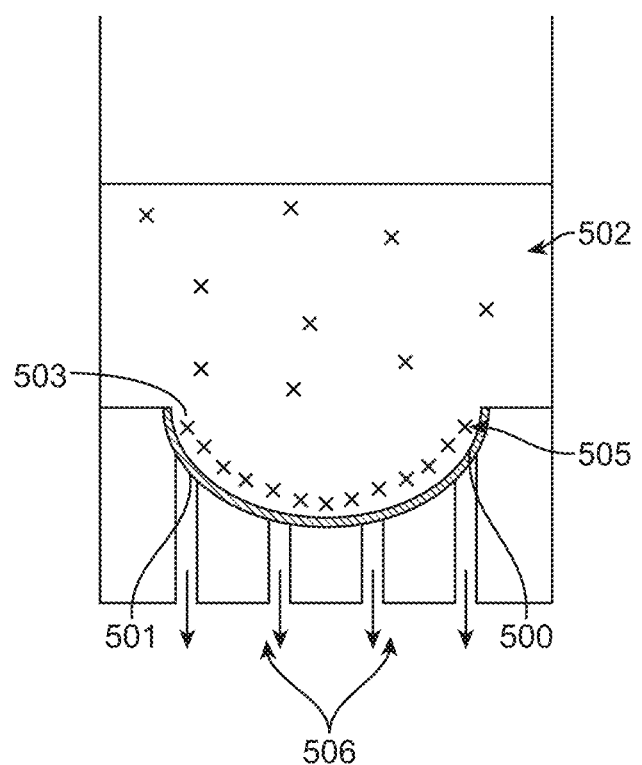

FIGS. 12A and 12B depict alternative embodiments of methods of the technology that are directed toward making lenses with a covalently attached bilateral hydrogel layer, in which the hydrogel layer sides differ in composition or depth. In some instances, it may be advantageous to produce a contact lens that is asymmetric (convex side vs. concave side) with regard to the thickness or composition of the hydrogel coating that is associated with the two surfaces, respectively. For example, it may be advantageous to form a hydrogel layer on the concave (or posterior) lens surface that is thicker than the layer on the convex (or anterior) lens surface, in order to hold a greater volume of aqueous tears against the cornea and prevent symptoms of dryness.

FIG. 12A shows a method to produce a lens with a thicker hydrophilic layer on the concave surface 503 in which a lens core 500 containing a UV blocking agent is dipped into a non-mixed solution 502 of coating polymer, and then exposed to UV light 504. UV light accelerates the reaction between polymers as well as the reaction between polymer and surface. The light strikes the lens on a vector that is perpendicular to the lens surface, directly onto the concave side 503 and through the convex side 501. Due to the UV blocking agent present in the lens, the concave side 503 is exposed to a higher dose of UV light, while the convex side 501 receives a relatively lower dose. This asymmetric UV dosing creates layers of varying thickness. To achieve complete independent variation in layer thickness control, light dosage of varying intensity can also be used to shine from each side.

FIG. 12B shows an alternative method for producing a thicker hydrogel layer on the concave surface 503 of the lens 500. As shown, the convex surface 501 of the lens 500 is held in a vacuum chuck 506 while exposing the concave surface 503 to the coating polymer 502. The vacuum suction pulls the aqueous solvent through the lens 500 while concentrating coating polymer at the lens interface at the concave surface 503. After achieving a desired layer thickness, the lens 500 is removed from the chuck 506. In some variations, the lens 500 is then placed into a well-mixed bath of coating polymer, to continue building the hydrogel layer on both sides of the lens.

H. EXAMPLES

The invention is further illustrated by the Examples that follow. The Examples are not intended to define or limit the scope of the invention.

Example 1: Functionalization of Silicone Hydrogel Lenses

Silicone hydrogel lenses were stored in purified water prior to functionalization. A solution of 10% by volume divinyl sulfone in 0.5M sodium bicarbonate (pH 11) were prepared. Lenses were added to the solution at a ratio of 6 lenses per 10 mL of solution and mixed vigorously on a shake plate for 60 minutes. The lenses were removed, washed in a strainer to remove any excess reaction solution, and added to a container of purified water at a ratio of 1 lens per 20 mL of water. They were mixed vigorously on a shake plate for 60 minutes. The washing procedure was repeated twice more for a total of 3 washes. Next, the lenses were stored in triethanolamine (TEOA) for at least 20 minutes and up to 6 hours prior to attaching the hydrogel layer.

Example 2: Functionalization of Silicone Lenses

Silicone lenses were stored dry prior to functionalization. Lenses were added to a solution of 10% hydrochloric acid and 2% hydrogen peroxide at a ratio of 6 lenses per 10 mL. The lenses were mixed vigorously for 5 minutes and then removed, washed in a plastic strainer to remove any excess reaction solution, and then added to a container of purified water a ratio of 1 lens per 20 mL of water. They were mixed vigorously for 5 minutes. Next the lenses were added to a solution of 95% ethanol, 3% water, 1% glacial acetic acid, and 1% 3-mercaptopropyltrimethoxysilane and mixed vigorously for 60 minutes. The lenses were rinsed in a strainer with pure ethanol and added to a container of pure ethanol at a ratio of 1 lens per 20 mL of ethanol. The lenses were mixed vigorously for 60 minutes. This washing procedure was repeated once more. Finally the lenses were removed from the rinse solution and allowed to dry. They were stored at 4° C. Prior to attaching hydrogel to the lenses, they were immersed in a solution of 150 mM dithiothreitol for 30 minutes and then rinsed in DI water. Following this step, hydrogel must be attached within 15 minutes.

Example 3: Plasma Functionalization of Silicone Containing Layers

Silicone containing layers (silicone or silicone hydrogel) were placed in a vacuum chamber for 2 hours to ensure all moisture was removed. After drying, lenses were inserted into a plasma chamber. Pressure was reduced to 375 milliTorr with continuous flow of nitrogen gas at 10 standard cubic centimeters per minute. The chamber was allowed to stabilize for 30 seconds before initiating plasma at 100 W for 3 minutes. The chamber was then vented to atmosphere and lenses removed. Lenses were then used within 1 hour.

Example 4: Preparation of Molds for Adding Bulk Layers to Contact Lenses

Molds were prepared using silicone hydrogel lenses and agar. 5 grams of Agar were dissolved in 333 mL of water and the solution was heated on a temperature controlled stirred plate until it reaches 88° C. A delrin plate containing small cavities (1" in diameter and 0.5" deep) was used to contain each individual mold. Liquid agar is pipetted to fill a mold cavity half full. A contact lens was then placed, convex side down, on top of the molten agar and additional agar was added on top to completely encase each lens in agar. Each plate contained 12 mold cavities and upon forming all 12, the plate was placed at 4° C. for 10 minutes until it is completely solidified. Once solid, a small brass punch of the same diameter as the contact lens (14 mm) was used to punch a hole in the agar around each lens. A hand held vacuum suction cup was used to pull the top of the agar mold off, tweezers were used to remove the silicone hydrogel lens, and then the top of the mold was replaced. This is repeated for each mold. Molds were then ready to be used for hydrogel attachment.

Example 5: Preparation of Poly(Ethylene Glycol) Hydrogel Macromer Solutions

The PEG hydrogel consists of two components. The first is 8-arm, 10 kDa poly(ethylene glycol) (PEG) end functionalized with vinyl sulfone (PEG-VS). The second is 4-arm, 10 kDa PEG end functionalized with thiol groups (PEG-SH). The PEG-VS was dissolved to 10% w/v in triethanolamine buffer (TEOA) at pH 8.0 and then filter sterilized in a 0.45 micron PVDF filter. The PEG-SH was dissolved to 10% w/v in distilled water and then filter sterilized in a 0.45 micron PVDF filter.

Example 6: Fabrication of a PEG Hydrogel

To form a PEG hydrogel, the macromer solutions of Example 5 were mixed together. To achieve varying polymer concentrations, a diluting volume of TEOA was added to the PEG-VS solution prior to mixing. The components were combined together with a 10% molar excess of thiol groups. The table below lists quantities used to fabricate various weight percentage PEG hydrogels. For example, to form a 5% PEG hydrogel: 96 μL of TEOA, was added to 30 μL of PEG-VS in an eppendorf tube. Finally, 66 mL of PEG-SH was added to the tube and it is mixed using a vortex for 3 seconds to ensure complete mixing. The PEG hydrogel was then incubated at 37° C. for 1 hour to ensure complete polymerization.

| Hydrogel | Volume (μL) | | | |
| --- | --- | --- | --- | --- |
| | TEOA | PEG-VS | PEG-SH | Total |
| 4% | 115.2 | 24.0 | 52.8 | 192.0 |
| 5% | 96.0 | 30.0 | 66.0 | 192.0 |
| 6% | 76.8 | 36.0 | 79.2 | 192.0 |
| 7% | 57.6 | 42.0 | 92.4 | 192.0 |
| 8% | 38.4 | 48.0 | 105.6 | 192.0 |
| 9% | 19.2 | 54.0 | 118.8 | 192.0 |
| 10% | 0.0 | 60.0 | 132.0 | 192.0 |

Example 7: Determining a Non-Swelling PEG Hydrogel Formulation

Figure 17:
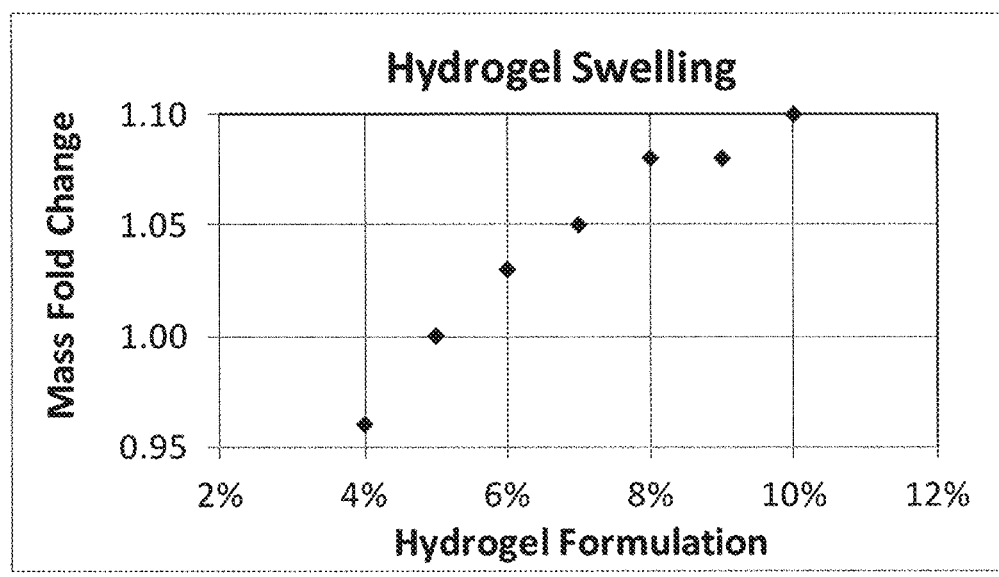
FIG. 17 illustrates a graph of mass fold change versus hydrogel formulation.

PEG hydrogel macromer solutions of Example 6 were pipetted between two hydrophobic glass slides separated by a 1 mm spacer and allowed to incubate at 37° C. for 1 hour. To determine swelling ratio, the PEG hydrogel was weighed immediately following polymerization and then immersed in distilled water for 24 hours. The swollen PEG hydrogel was weighed again to determine the amount of water absorbed into the polymer network to determine the mass fold increase. As shown in FIG. 17, the mass change for all PEG hydrogel formulations was small and the PEG hydrogel formulation of 5% did not undergo any swelling following polymerization.

Example 8: Fabricating a Contact Lens with a Bulk Layer of PEG Hydrogel on the Concave Side To produce a contact lens with a bulk layer of PEG hydrogel, the molds of Example 3 were prepared using sacrificial lenses identical to those receiving a bulk layer of PEG hydrogel. A solution of 50% by volume TEOA, 34.4% PEG-SH, and 15.6% PEG-VS were prepared by mixing in an eppendorf tube and vortexing. The top of the agar mold was removed using a small hand held vacuum suction device and the functionalized lens (of either Example 1 or Example 2 or Example 3) were placed into the mold. 20 μL of the mixed PEG solution was placed onto the concave side of the lens, and the top of the agar mold was replaced on top. Air bubbles were removed by gently tapping on the top of the mold until all air was removed from the mold. The mold was placed in an incubator at 37° C. for 1 hour. The lenses were then removed, visually inspected, and placed in purified water for storage.

Example 9: Fabricating a Contact Lens with a Bulk Layer of PEG Hydrogel on the Convex Side To produce a contact lens with a bulk layer of PEG hydrogel, the molds of Example 3 were prepared using sacrificial lenses identical to those receiving a bulk layer of PEG hydrogel. A solution of 50% by volume TEOA, 34.4% PEG-SH, and 15.6% PEG-VS were prepared by mixing in an eppendorf tube and vortexing. The top of the agar mold were removed using a small hand held vacuum suction device and 20 μL of the mixed PEG solution was placed into the bottom of the mold. The functionalized lenses (of either Example 1 or Example 2 or Example 3) were placed into the mold and the top of the agar mold was replaced on top. Air bubbles were removed by gently tapping on the top of the mold until all air was removed from the mold. The mold was placed in an incubator at 37° C. for 1 hour. The lenses are then removed, visually inspected, and placed in purified water for storage.

Example 10: Fabricating a Contact Lens with a Bulk Layer of Hydrogel on Both Concave and Convex Sides (Encased)

To produce a contact lens encased in a bulk layer of PEG hydrogel, the molds of Example 4 were prepared using sacrificial lenses identical to those receiving a bulk layer of PEG hydrogel. A solution of 50% by volume TEOA, 34.4% PEG-SH, and 15.6% PEG-VS was prepared by mixing in an eppendorf tube and vortexing. The top of the agar mold was removed using a small hand held vacuum suction device and 20 μL of the mixed PEG solution is placed into the bottom of the mold. The functionalized lens (of either Example 1 or Example 2 or Example 3) were placed into the mold and 20 μL of the mixed PEG solution was placed onto the concave side of the lens and then the top of the agar mold was placed on top. Air bubbles were removed by gently tapping on the top of the mold until all air was removed from the mold. The mold was placed in an incubator at 37° C. for 1 hour. The lenses were then Removed, Visually Inspected, and Placed in Purified Water for Storage.

Example 11: Oaysys Lenses Encapsulated in Peg Hydrogel

Contact lenses (Acuvue Oaysys, lotrafilcon A) were functionalized according to Example 1. Agar molds were prepared according to Example 4. Lenses were encapsulated according to Example 10.

Example 12: Oaysys Lenses with a Bulk Layer of PEG Hydrogel

Contact lenses (Acuvue Oaysys, lotrifilcon A) were functionalized according to Example 1. Agar molds were prepared according to Example 4. A bulk layer was added according to Example 8.

Example 13: PureVision Lenses Encapsulated in PEG Hydrogel

Contact lenses (PureVision, balafilcon A) were functionalized according to Example 1. Agar molds were prepared according to Example 4. Lenses were encapsulated according to Example 10.

Example 14: PureVision Lenses with a Bulk Layer of PEG Hydrogel

Contact lenses (PureVision, balafilcon A) were functionalized according to Example 1. Agar molds were prepared according to Example 4. A bulk layer was added according to Example 8.

Example 15: Silicone Lenses Encapsulated in a Bulk Layer of PEG Hydrogel

Silicone lenses (NuSil, Med 6755) were functionalized according to Example 2. Agar molds were prepared according to Example 4. Lenses were encapsulated according to Example 10.

Example 16: Silicone Lenses with a Bulk Layer of PEG Hydrogel on the Concave Side Silicone lenses (NuSil, Med 6755) were functionalized according to Example 2. Agar molds were prepared according to Example 4. A bulk layer was added according to Example 8.

Example 17: Silicone Lenses with a Bulk Layer of PEG Hydrogel on the Convex Side Silicone lenses (NuSil, Med 6755) were functionalized according to Example 2. Agar molds were prepared according to Example 4. A bulk layer was added according to Example 9.

Example 18: Contact Angle Measurement

To measure lens contact angles, the captive bubble technique was used. First, the lens was spun in a vortex in distilled water to remove surface contaminants. The lens was then submerged in distilled water and suspended atop a plate that has a hole through which the convex surface of the lens protrudes downward. An $^{11}/_{16}$" diameter stainless steel ball was placed atop the lens to keep it in place when the bubble was applied. Next, the curved tip of a 16 gauge blunt needle was placed just below the surface of the center of the lens. A bubble was then advanced until it makes contact with the lens, at which point the bubble was retracted until it breaks free from either the lens or the needle. A high-definition video camera records the entire procedure, after which an image was saved from the frame immediately preceding the moment the bubble detaches from either the lens or the needle. From this image, the angles between the lens and the bubble on both sides of the bubble were calculated in MATLAB and saved as the contact angles for that lens.

Example 19: Contact Angle Measurement of Oasys Lenses with Bulk Layers of PEG Hydrogel The contact angle of lenses of Example 11 were measured according to Example 18.

| Lens with bulk layers of PEG hydrogel | Contact Angle* |
| --- | --- |
| Lens 1 | 12.3 |
| Lens 2 | 14.6 |
| Lens 3 | 10.7 |
| Average | 12.5 |

*Contact angle is the average of 3 tests

Example 20: Preparation of Photo-Polymerizable Poly(Ethylene Glycol) Hydrogel Macromer Solutions The hydrogel consists of two components. The first is 8-arm, 10 kDa poly(ethylene glycol) (PEG) end functionalized with acrylate (PEG-Ac). The second is 4-arm, 10 kDa PEG end functionalized with thiol groups (PEG-SH). The PEG-Ac is dissolved to 10% w/v in triethanolamine buffer (TEOA) at pH 8.0 and then filter sterilized in a 0.45 micron PVDF filter. The PEG-SH is dissolved to 10% w/v in distilled water and then filter sterilized in a 0.45 micron PVDF filter.

Example 21: Fabrication of a Photo-Polymerizable PEG Hydrogel

To form a hydrogel, the macromer solutions of Example 20 are mixed together. To achieve varying polymer concentrations, a diluting volume of TEOA is added to the PEG-Ac solution prior to mixing. The components are combined together with a 10% molar excess of thiol groups. The table below lists quantities used to fabricate various weight percentage hydrogels. For example, to form a 5% PEG hydrogel: 96 μL of TEOA, is added to 30 μL of PEG-Ac in an eppendorf tube. Finally, 66 mL of PEG-SH is added to the tube and it is mixed using a vortex for 3 seconds to ensure complete mixing. The solution is then exposed to UV light (365 nm, 5 mW/cm2, 10 min) to polymerize the mixture.

| | Volume (μL) | | | |
| --- | --- | --- | --- | --- |
| Hydrogel | TEOA | PEG-Ac | PEG-SH | Total |
| 4% | 115.2 | 24.0 | 52.8 | 192.0 |
| 5% | 96.0 | 30.0 | 66.0 | 192.0 |
| 6% | 76.8 | 36.0 | 79.2 | 192.0 |
| 7% | 57.6 | 42.0 | 92.4 | 192.0 |
| 8% | 38.4 | 48.0 | 105.6 | 192.0 |
| 9% | 19.2 | 54.0 | 118.8 | 192.0 |
| 10% | 0.0 | 60.0 | 132.0 | 192.0 |

Example 22: Layer by Layer Reactive Spin Coating

The macromer solutions of Example 20 are prepared. Lenses of Example 1 or 2 or Example 3 are fixed to a spin coater chuck. The lenses are rotated at speeds ranging from 500-5000 rpms. While revolving, the lens is continuously exposed to UV light (365 nm, 5 mW/cm2), while drops of macromer solution are alternately added to the lenses as follows: 10 μL of PEG-Ac followed by 10 μL of PEG-SH, etc. This is repeated for multiple cycles, ranging from 10-1000.

Example 23: PEG Dipping Solution for Enzyme Mediated Redox Chain Initiation

The PEG dipping solution consists of a mixture of glucose oxidase (GOX), Fe+2, and polyethylene glycol diacrylate (PEGDA) (MW from 2,000 Da-10,000 Da). For example, a dipping solution may contain 3.1×10−6 M GOX, 2.5×10−4 M iron (II) sulfate, 10% PEGDA 5,000 Da.

Example 24: Contact Lens Encapsulated in PEG Hydrogel Via Interfacial Enzyme Mediated Redox Chain Initiation The glucose loaded lenses of Example 18 are dipped into the solution of Example 19 until the hydrogel layer grows to the desired thickness. The time to achieve a layer thickness of 10-100 microns ranges from 2 seconds-10 minutes.

Example 25: Captive Bubble Contact Angle Measurement

A macro lens of 10× magnification was affixed to the camera detailed in Example 17, Contact Angle Measurement. The macro lens enables close-up movies of the bubble/contact lens interface. A syringe pump (New Era Syringe Pump 750) was added to the testing fixture to enable continuous and repeatable bubble control. The pump was programmed using Syringe Pump Pro programming software. A new test fixture chamber was constructed of black acrylonitrile butadiene styrene (abs) to facilitate the use of a thin, clear, glass viewing plate and a semi-opaque background screen. The tested lens were held between two plates and submerged in PBS. An air bubble was extended 2 mm from a straight 16 gage blunt needle until it made contact with the lens. A high-definition web camera recorded the lens+bubble interface while 30 of air was infused and then withdrawn at a rate of 7.2 µl/min from the micro-syringe (Precision Sampling corp, series A-2, 25 ul). The contact angle of lenses described herein were measured using Example 25 and are detailed in FIGS. 13A-13T. The contact angles were measured using specially developed MatLab Code which is detailed in FIGS. 14A-14J.

Example 26: PEG Concentration Dependence

To determine the effect of PEG concentration on polymerization rate for the hydrogel, the macromer solutions of Example 4 were combined at decreasing concentrations and checked at set time intervals until solidification. PEG-VS and PEG-SH were combined in the below quantities with the specified quantity of 0.2M TEOA in 1.5 ml eppendorf tubes to form the noted concentrations. Each solution was vortexed and then pipetted onto a glass slide. The PEG solution was pipetted at 5, 10, or 30 second intervals (increasing time interval for lower concentrations) until filaments formed, indicating that the gel had polymerized. The time-until-polymerization was recorded.

|  |  | PEG Concentration | | | | | | |
|---|---|---|---|---|---|---|---|---|
|  |  | 1% | 2% | 3% | 4% | 6% | 8% | 10% |
| Volume (µL) | PEG-VS | 10.6 | 10.6 | 16.0 | 21.3 | 31.9 | 42.6 | 53.2 |
|  | PEG-SH | 19.4 | 19.4 | 29.0 | 38.7 | 58.1 | 77.4 | 96.8 |
|  | TEOA | 270 | 120 | 105 | 90 | 60 | 30 | 0 |
|  | Total Volume | 300 | 150 | 150 | 150 | 150 | 150 | 150 |
|  | Polymerization Time (Sec) | 8820 | 680 | 406 | 250 | 150 | 103 | 83 |

Example 27: PEG pH Dependence

To determine the polymerization rate of the hydrogel as a function of pH, the macromer solutions of Example 4 were combined with 0.2M TEOA at increasing pH levels. 20% PEG-VS and 10% PEG-SH were combined in the below quantities with TEOA at the specified pH in 1.5 ml eppendorf tubes. The TEOA buffer was prepared at the noted concentrations by adjusting pH with NaOH or HCl as required. A 4% hydrogel solution was made. Each solution was vortexed and then pipetted onto a glass slide. The PEG solution was pipetted at 5, 10, or 30 second intervals (increasing time interval for lower pH) until filaments formed, indicating that the gel had polymerized. The time-until-polymerization was recorded.

Example 28: Lenses Dip Coated to Obtain a Bulk Layer of PEG

Lenses were functionalized using nitrogen gas in a plasma chamber (Plasma Etch PE-50) at settings: 375 mTorr, 3 min, 100% RF power. Pressure was reduced to 375 milliTorr with continuous flow of nitrogen gas at 10-20 standard cubic centimeters per minute. The chamber was allowed to stabilize for 30 seconds before initiating plasma at 100 W for 3 minutes. The chamber was then vented to atmosphere and lenses removed. Lenses were then used within 1 hour. The PEG macromer solutions of Example 4 were combined with excess TEOA to obtain solutions with a total solids concentration of 0.1% and 0.5% and with a 10% molar excess of VS (See quantities in table below). A 0% PEG solution was also prepared as a control. The volume of 0.2M TEOA detailed below was added to individual plastic vials (McMaster Carr 4242T83); followed by the noted volume of PEG-VS. The surface functionalized PureVision lenses were added to this solution and vortexed. The PEG-SH was added and the solution was again vortexed. The lenses were placed on a mixing table for 24 hrs. The lenses were transferred to new plastic vials containing Phosphate Buffered Saline (PBS) and placed on the mixing table for 24 hrs. The lenses were transferred to glass jars and autoclaved (Tuttnauer 3870 E) in a wet cycle at 250° F. for 30 min.

|  |  | PEG Concentration | | |
|---|---|---|---|---|
|  |  | 0.00% | 0.1% | 0.5% |
| Volume (µL) | PEG-VS | 0.0 | 5.3 | 26.6 |
|  | PEG-SH | 0.0 | 9.7 | 48.4 |
|  | TEOA | 1500 | 1485 | 1425 |
|  | Total | 1500 | 1500 | 1500 |

Example 29: Silicone Lenses Surface Activated to Enhance Hydrogel Adhesion

Silicone lenses (NuSil, Med 6755) were functionalized with the plasma treatment process of Example 28. In a 50 mL conical tube, the lenses were placed in a 10% w/v divinyl sulfone solution with a sodium bicarbonate buffer at pH 11 and vortexed. After 1 hr on a mixing table, the lenses were washed with 20 ml of deionized water (DI Water) and placed back on the mixing table in 40 ml of DI water. After 1 hr, this cycle was repeated once more and the lenses were placed in the fridge for 8 hrs in 40 ml of DI water.

Example 30: Silicone Lenses Dip Coated to Obtain a Bulk Layer of PEG

Silicone lenses (NuSil, Med 6755) were functionalized, dip coated and autoclaved, in the 0%, 0.1%, and 0.5% PEG solutions per Example 28.

Example 31: PureVision Lenses Surface Activated and Dip Coated to Obtain a Bulk PEG Layer Contact lenses (PureVision, balafilcon A) were functionalized with the plasma treatment process of Example 28. The lenses were placed into 400 uL of 10% PEGVS, vortexed, and then positioned on the mixing table for 5 minutes. Subsequently, the lenses were placed in 3 mL of 0.2M TEOA, vortexed, and set on the mixing table for 5 minutes. The lenses were added to a solution of 0.1% PEG in TEOA according to example 28. The lenses were vortexed, stationed on the mixing table for 24 hrs, and autoclaved according to Example 28.

Example 32: PureVision Lenses Dip Coated with FITC-Maleimide Addition for PEG Layer Visualization Contact lenses (PureVision, balafilcon A) were functionalized with the plasma treatment process of Example 28. The lenses were placed into 0.1% and 0.5% PEG solutions according to example 28. 5.1 µl of FITC-Maleimide @ 10 mg/mL was added to each of the solutions to visualize the PEG layer. The solutions were vortexed and placed on a mixing table for 24 hrs.

Example 33: PureVision Lenses Dip Coated to Obtain a Bulk Layer of PEG with Shortened Wash Cycle Contact lenses (PureVision, balafilcon A) were functionalized and coated according to Example 28. After 24 hrs in the PEG solution, the lenses were placed in vials containing PBS and placed on the mixing table for 1.5 hrs. The lenses were placed in a second set of vials containing PBS and placed on the mixing table for 1.5 hrs. The lenses were autoclaved according to Example 28.

Example 34: PureVision Lenses Dip Coated in Ultra-Low Concentration PEG with No Wash Cycle Contact lenses (PureVision, balafilcon A) were functionalized with the plasma treatment process of Example 28. The macromer solutions of Example 4 were combined with TEOA at 0.01% and 0.05% PEG. A 0% PEG solution was also prepared as a control. The PureVision lenses were added to this solution and vortexed. The PEG-SH was added and the solution was again vortexed. The lenses were autoclaved in individual plastic vials for 30 min at 250° F. without being washed and without being removed from the PEG solution.

|  |  | PEG Concentration | | |
| --- | --- | --- | --- | --- |
|  |  | 0.00% | 0.01% | 0.05% |
| Volume (µL) | PEG-VS | 0.0 | 0.53 | 2.66 |
|  | PEG-SH | 0.0 | .97 | 4.84 |
|  | TEOA | 1500 | 1498.5 | 1492.5 |
|  | Total | 1500 | 1500 | 1500 |

Example 35: PureVision Lenses Dip Coated in Low Concentration PEG with Immediate Autoclave in Glass Contact lenses (PureVision, balafilcon A) were functionalized and coated according to Example 28. The lenses were placed in glass vials (McMaster-Carr 4417T48) containing 3 ml of PBS and autoclaved according to Example 28.

Example 36: PureVision Lenses Dip Coated and Extracted in Isopropanol Alcohol Contact lenses (PureVision, balafilcon A) were functionalized and coated at the 0% and 0.5% concentrations according to Example 28. The lenses were placed on a mixing table for 18 hrs. The PEG solution was replaced with pure isopropanol alcohol (IPA) and returned to the mixing table for 1 hr. The IPA was switched and the lenses were washed for an additional hour. The IPA was replaced with deionized water and the lenses were washed for 1 hr. The water was replaced twice and the lenses were washed for 30 min each time. The lenses were placed in PBS and autoclaved per Example 28.

Example 37: PureVision Lenses Dip Coated in Organic Solvents to Obtain Bulk Layer of PEG 1 ml of pure TEOA was added to 40 ml of isopropyl alcohol (IPA) to make a 0.2M solution. Pure Methanol was added to IPA at 0.2M TEOA to create a 50% solution. 1 ml of concentrated TEOA was dissolved into 40 ml of pure Methanol (MeOH) to form a MeOH at 0.2 Molar TEOA solution. Contact lenses (PureVision, balafilcon A) were functionalized with the plasma treatment process of Example 28. The macromer solutions of Example 4 were combined with the 50% MeOH and 50% IPA at 0.2M TEOA at 0.5% PEG. A 0% PEG solution was also prepared as a control. The macromer solutions of Example 4 were also combined with the MeOH at 0.2 M TEOA at 0.5% PEG. The volume of MeOH and IPA detailed below were added to individual plastic vials; the surface functionalized PureVision lenses were added to the solution and vortexed. The PEG-VS and PEG-SH were added and the solution but the solution was not vortexed due to the sensitivity of the lenses in solvents. The lenses were placed on a mixing table for 18 hrs. A washing series was utilized to remove the organic solvents; the solutions were changed to pure IPA and the lens were placed on the mixing table for 1 hr. The IPA was replaced with deionized (DI) water and the lenses were placed on the mixing table for 1 hr. The DI water was replaced with PBS and the lenses were autoclaved per Example 28.

Example 38: PureVision Lenses with DVS Activation During IPA Solvent Extraction 1 ml of 100% TEOA was added to 40 ml of isopropyl alcohol (IPA) to make a 0.2M solution. Contact lenses (PureVision, balafilcon A) were functionalized according to Example 28 and placed in 5 ml of IPA at 0.2M TEOA. Non-plasma treated and no-peg lenses were also prepared as controls. 7.5% DVS was added to each vial. The lenses were swirled in the solution and then placed on the mixing table for 1 hour. The DVS was discarded and 40 ml of IPA was added to each solution prior to placing the lenses on the mixing table for 1 hour. The IPA was changed and the lenses were placed on the mixing table for 1 hr. The IPA was replaced with 40 ml of deionized (DI) water and mixed for 1 hr. The DI water was changed and the lenses were mixed for 1 hr. The lenses were dip coated and autoclaved according to Example 28.

Example 39: PureVision Lenses with DVS Activation During MeOH Solvent Extraction 1 ml of 100% TEOA was added to 40 ml of methanol alcohol (MeOH) to make a 0.2M solution. Contact lenses (PureVision, balafilcon A) were functionalized according to Example 28 and placed in 5 ml of MeOH at 0.2M TEOA. Non-plasma treated and no-peg lenses were also prepared as controls. 7.5% DVS was added to each vial. The lenses were swirled in the solution and then placed on the mixing table for 1 hour. The DVS was discarded and 40 ml of IPA was added to each solution prior to placing the lenses on the mixing table for 1 hour. The IPA was changed and the lenses were placed on the mixing table for 1 hr. The IPA was replaced with 40 ml of deionized (DI) water and mixed for 1 hr. The DI water was changed and the lenses were mixed for 1 hr. The lenses were dip coated and autoclaved according to Example 28.

Example 40: PureVision Lenses Dip Coated in Methanol Solvent to Obtain a Bulk Layer of PEG Contact lenses (PureVision, balafilcon A) were functionalized according to Example 28. A MeOH at 0.2 Molar TEOA solution was made according to Example 39. The macromer solutions of Example 4 were combined with the MeOH at 0.2 M TEOA at 0.1%, 0.25% and 0.5% PEG. A 0% PEG solution was also prepared as a control. The volume of MeOH detailed below was added to individual glass vials; followed by the noted volume of PEG-VS. The surface functionalized PureVision lenses were added to this solution and vortexed. The PEG-SH was added and the solution was again vortexed. The lenses were placed on a mixing table for 24 hrs.

A MeOH washing cycle was developed and implemented: The MeOH at 0.2 M TEOA and PEG solution was replaced with pure MeOH and the lenses were placed on the mixing table for 1 hr. The MeOH was replaced with IPA and the lenses were placed on the mixing table for 1 hr. The IPA was replaced with a solution consisting of 50% IPA and 50% DI water and the lenses were placed on the mixing table for 1 hr. The 50% solution was replaced with 100% DI water and the lenses were placed on the mixing table for 1 hr. The DI water was replaced with Phosphate Buffered Saline (PBS) and autoclaved according to Example 28.

| | | PEG Concentration | | | |
|---|---|---|---|---|---|
| | | 0.00% | 0.1% | 0.25% | 0.5% |
| Volume (µL) | PEG-VS | 0.0 | 5.3 | 13.25 | 26.6 |
| | PEG-SH | 0.0 | 9.7 | 24.25 | 48.4 |
| | MeOH at 0.2M TEOA | 1500 | 1485 | 1462.5 | 1425 |
| | Total | 1500 | 1500 | 1500 | 1500 |

Example 41: Plasma Treatment Process

The setting for the plasma treatment process were tested and updated. The plasma treatment process used nitrogen gas, grade 5, in a plasma chamber (Plasma Etch PE-50) with settings: 150 mTorr set point, 200 mtorr vacuum, 3 min, @ 100% RF power. Pressure was reduced to 200 milliTorr with continuous flow of nitrogen gas at 2.5-5 standard cubic centimeters per minute. The chamber was allowed to stabilize for 30 seconds before initiating plasma at 100 W for 3 minutes. The chamber was then vented to atmosphere and lenses removed. Lenses were then used within 1 hour.

Example 42: Lenses Extracted in Isopropanol Alcohol, Desiccated, and Dip Coated Lenses were placed in 1.5 ml of IPA and set on a mixing table for 18 hrs. The IPA was switched and the lenses were washed for an additional hour. The IPA was replaced with deionized water and the lenses were washed for 1 hr. The water was replaced twice and the lenses were washed for 30 min each time. The lenses were placed in a vacuum chamber and the chamber was evacuated using a pump (Mastercool, 6 cfm) for 24 hrs. The lenses were functionalized and coated at the 0% and 0.5% concentrations according to Example 28 with the plasma treatment process of Example 41. The PEG solution was replaced with deionized water and the lenses were washed for 1 hr. The lenses were placed in PBS and autoclaved per Example 28.

Example 43: PureVision Lenses Dip Coated to Obtain a Bulk Layer of PEG

Example 28 was repeated using the plasma treatment process of Example 41.

Example 44: PureVision Lenses Dip Coated in Low Concentration PEG with Immediate Autoclave in Glass Example 36 was repeated using the plasma treatment process of Example 41.

Example 45: PureVision Lenses Dip Coated in Organic Solvents to Obtain Bulk Layer of PEG Example 38 was repeated using the plasma treatment process of Example 41.

Example 46: PureVision Lenses Dip Coated in Methanol Solvent to Obtain a Bulk Layer of PEG Example 40 was repeated using the plasma treatment process of Example 41.

Example 47: PureVision Lenses Extracted in Isopropanol Alcohol, Desiccated, Dip Coated, with Immediate Autoclave Contact lenses (PureVision, balafilcon A) were extracted, desiccated, and dip coated according to Example 42. Immediately after the dip coating process the lenses were autoclaved while in the PEG solution according to Example 28.

Example 48: Silicone Lenses Extracted in Isopropanol Alcohol, Desiccated, and Dip Coated Silicone contact lenses (NuSil, Med 6755) were extracted, desiccated, dip coated and autoclaved according to Example 42.

Example 49: PureVision Lenses Extracted in Isopropanol Alcohol, Desiccated, and Dip Coated Contact lenses (PureVision, balafilcon A) lenses were extracted, desiccated, dip coated and autoclaved according to Example 42.

Example 50: PureVision Lenses Dip Coated in Methanol Solvent with Heated Rotation to Obtain a Bulk Layer of PEG Contact lenses (PureVision, balafilcon A) were functionalized using oxygen gas in a plasma chamber (Plasma Etch PE-50) at settings: 200 mTorr, 3 min, 100% RF power. The lenses were dip coated according to Example 40 and placed in a heated oven with rotation at 37 C for 24 hours. The lenses were washed and autoclaved according to Example 40, but with the following shortened wash times: MeOH 2× quick swirls, IPA 2× 20 min, IPA:H20 (50:50) 20 min, H$_2$O 10 min, and PBS for autoclave.

Example 51: Silicone Lenses Dip Coated in Methanol Solvent with Heated Rotation to Obtain a Bulk Layer of PEG Silicone contact lenses (NuSil, Med 6755) were functionalized using oxygen gas in a plasma chamber (Plasma Etch PE-50) at settings: 200 mTorr, 3 min, 100% RF power. The lenses were dip coated according to Example 40 and placed in a heated oven with rotation at 37° C. for 24 hours. The lenses were washed and autoclaved according to Example 40, but with the following shortened wash times: MeOH 2× quick swirls, IPA 2× 20 min, IPA:H20 (50:50) 20 min, H$_2$O 10 min, and PBS for autoclave.

Example 52: PureVision Lenses Pre-Activated, Dip Coated in Methanol Solvent with Heated Rotation Lenses (PureVision, balafilcon A) were functionalized using oxygen gas in a plasma chamber (Plasma Etch PE-50) at settings: 200 mTorr, 3 min, 100% RF power. The lenses were pre-activated with PEG-VS or VS, dip coated according to Example 40 and placed in a heated oven with rotation at 37 C for 24 hours. The lenses were washed and autoclaved according to Example 40, but with the following shortened wash times: MeOH 2× quick swirls, IPA 2× 20 min, IPA:H20 (50:50) 20 min, H$_2$O 10 min, and PBS for autoclave.

Example 53: Silicone Lenses Dip Coated to Obtain a Bulk Layer of PEG

Example 30 was repeated using the plasma treatment process of Example 41.

Example 54: PureVision Lenses Dip Coated to Obtain a Bulk Layer of PEG Using Oxygen Gas Example 28 was repeated using oxygen gas, grade 5, during the plasma treatment process.

Example 55: PureVision Lenses Plasma Treated and Dip Coated in Hyaluronic Acid to Obtain a Bulk Layer Contact lenses (PureVision, balafilcon A) were functionalized according to Example 28 with the addition hyaluronic acid (HA) at of 10 mg of hyaluronic acid (HA). Lenses were added to this solution and placed on the mixing table for 1 hr. The HA solution was replaced with DI water and the lenses were placed on a mixing table for 1 hr. The water was replaced and the lenses were placed on a mixing table for 1 hr, 2 additional times. The lenses were placed in individual plastic vials containing 3 ml-5 ml of PBS.

Example 56: PureVision Lenses Plasma Treated and Surface Activated with DVS in NaOH Contact lenses (PureVision, balafilcon A) were functionalized according to Example 28. 0.5 ml of DVS was added to 4.5 ml of 0.5M Sodium BiCarbonate (NaOH). Lenses were added to this solution and placed on the mixing table for 20 min. Lenses were also placed in 5 ml of NaOH as controls. The solution was replaced with DI water and the lenses were placed on the mixing table for 20 min. This step was repeated 2 additional times.

Example 57: PureVision Lenses Plasma Treated and Dip Coated in Hyaluronic Acid to Obtain a Bulk Layer with a FITC-Maleimide Addition for Layer Visualization Contact lenses (PureVision, balafilcon A) were functionalized according to Example 28 and dip coated according to Example 55. 51 μl of FITC-Maleimide was added to each of the solutions to visualize the PEG layer. The lenses were washed and stored according to Example 55.

Example 58: PureVision Lenses Plasma Treated and Dip Coated in Hyaluronic Acid in NaOH to Obtain a Bulk Layer Contact lenses (PureVision, balafilcon A) were functionalized according to Example 28. 5 ml of HA was added to 45 ml of 10M NaOH. 5 ml of HA was added to 45 ml of DI water for a control. Lenses were added to these solutions and placed on the mixing table for 1 hr. The solutions were replaced with DI water and the lenses were placed on the mixing table for 1 hr. The lenses were placed in individual plastic vials containing 3 ml-5 ml of PBS.

Example 59: Silicone Lenses Plasma Treated then Encapsulated in PEG Hydrogel Silicone lenses (NuSil, Med 6755) were functionalized according to Example 28. Agar molds were prepared according to Example 4. Lenses were encapsulated according to Example 10.

Example 60: PureVision Lenses Plasma Treated and Dip Coated in Low or High Molecular Weight PEG Contact lenses (PureVision, balafilcon A) were functionalized using monofunctional polyethylene glycol, end functionalized in vinyl sulfone (mPEG-VS). mPEGs of 5 kDa and 20 kDa were used.

5% w/v total mPEG-VS solutions were prepared in triethanolamine buffer (TEOA) at pH 8.0 and then filter sterilized in a 0.45 micron PVDF filter. A 0% PEG solution was also prepared as a control.

3 ml of PEG solution was added to individual plastic vials (McMaster Carr 4242T83). The surface functionalized PureVision lenses were added to this solution and vortexed. The lenses were placed on a mixing table for 24 hrs. The lenses were transferred to new plastic vials containing Phosphate Buffered Saline (PBS) and placed on the mixing table for 24 hrs.

Example 61: Silicone Lenses Plasma Treated then Encapsulated in PEG Hydrogel with a FITC-Maleimide Addition for PEG Layer Visualization Silicone lenses (NuSil, Med 6755) were functionalized according to Example 28. Agar molds were prepared according to Example 4. 5.1 μl of FITC-Maleimide was added to each of the solutions to visualize the PEG layer. Lenses were encapsulated according to Example 10.

Example 62: Oaysys Lenses Desiccated and Plasma Treated then Encapsulated in PEG Hydrogel Contact lenses (Acuvue Oaysys, senofilcon A) were desiccated according to Example 42 and functionalized according to Example 28. Agar molds were prepared according to Example 4. Lenses were encapsulated according to Example 10.

Example 62: Lenses Encapsulated in PEG Hydrogel

Lenses (Lotrafilcon B) were functionalized according to Example 1. Agar molds were prepared according to Example 4. Lenses were encapsulated according to Example 10.

Example 63: Lenses Desiccated and Plasma Treated then Encapsulated in PEG Hydrogel Lenses (Lotrafilcon B) were desiccated according to Example 42 and functionalized according to Example 28. Agar molds were prepared according to Example 4. Lenses were encapsulated according to Example 10.

Example 64: Silicone Lenses Plasma Treated and Dip Coated in Low or High Molecular Weight PEG Silicone lenses (NuSil, Med 6755) were functionalized according to Example 28, with the addition of a non-plasma treated control, and dip coated according to Example 60.

Example 65: PureVision Lenses Plasma Treated then Encapsulated in PEG Hydrogel Contact lenses (PureVision, balafilcon A) were functionalized according to Example 28. Agar molds were prepared according to Example 4. Lenses were encapsulated according to Example 10.

Example 66: PureVision Lenses Dip Coated to Obtain a Bulk Layer of PEG

Contact lenses (PureVision, balafilcon A) were functionalized and coated according to Example 28. The lenses were washed according to example 33 and autoclaved according to Example 28.

Example 67: Glucose Loading of Hydrogel Contact Lenses

Hydrogel contact lenses containing acrylate groups on the surface were incubated in d-Glucose solution (10 mL/lens) for at least 4 hours. The glucose concentration may range from 0.1 mM to 25 mM.

Example 68: PureVision Lenses Dip Coated and Accelerated Life Tested to Identify the Stability of the Bulk Layer of PEG Example 46 was repeated; contact lenses (PureVision, balafilcon A) dip coated in methanol solvent to obtain a bulk layer of peg. Post autoclave process according to Example 28, the lenses were tested according to Example 25. The lenses were placed in PBS and autoclaved once more according to Example 28 or placed in sterile saline (Walgreens—Sterile Saline Solution). The lenses were placed in hybridization ovens (Stovall Life Science Inc) at 20, 40, or 60 degrees Centigrade. The lenses were tested on dates that correspond to six or twelve months of accelerated life testing as detailed by FDA 510K clearance requirements for medical devices generally, and daily wear contacts specifically. Post testing, the sterile saline was replaced with new sterile saline and the lenses were replaced in the respective hybridization oven. Lot numbers with corresponding solutions and temperatures are detailed below.

| n = 6 Temp [C] | Storage Solution Saline | Sterile Saline |
|---|---|---|
| 0% PEG | | |
| 20 | M167 | M170 |
| 45 | M168 | M171 |
| 60 | M169 | M172 |
| 0.5% PEG | | |
| 20 | M173 | M176 |
| 45 | M174 | M177 |
| 60 | M175 | M178 |

Example 69: MJS Lenses Dip Coated to Obtain a Bulk Layer of PEG

MJS Lenses (MJS Lens Technology Ltd, Standard Product, 55% water content) were functionalized according to Example 41, coated and autoclaved according to Example 28, and tested according to Example 25. The lenses were then placed in hybridization ovens (Stovall Life Science Inc) at 60 degrees Celsius for 7 days. The sterile saline (Walgreens—Sterile Saline Solution) was replaced and the lenses were retested according to Example 25.

Example 70: Determining Water Content of Poly(Ethylene Glycol) Coated Contact Lenses Utilizing Mass Balance This example illustrates how to determine the water content of a contact lens of the invention. In an effort to determine the potential water content of the polyethyleneglycol layer(s) of the contact lenses of the invention, samples consisting of the layer components are prepared for evaluation. The resulting gels are then hydrated and tested to determine water content.

PEG hydrogel macromer solutions as described in Example 5 were pipetted between two hydrophobic glass slides separated by a 1 mm spacer and allowed to incubate at 37° C. for 1 hour.

Hydrated samples were blotted dry and the mass at hydrated state was recorded via mass balance. Following the recording of the mass at hydrated state, the samples were all dried under a vacuum of <1 inch Hg overnight.

Dried samples were removed from the vacuum oven after overnight drying and then measured to record dry mass. Water content was calculated using the following relationship: Water content=[(wet mass−dry mass)/wet mass]×100%

Example 71: Preparation of Poly(Ethylene Glycol) Hydrogel Macromer Solutions In one example, the PEG hydrogel consists of two components. The first is 8-arm, 10 kDa poly(ethylene glycol)

(PEG) end functionalized with vinyl sulfone (PEG-VS). The second is 4-arm, 10 kDa PEG end functionalized with thiol groups (PEG-SH). The PEG-VS was dissolved to 10% w/v in triethanolamine buffer (TEOA) at pH 8.0 and then filter sterilized in a 0.45 micron PVDF filter. The PEG-SH was dissolved to 10% w/v in distilled water and then filter sterilized in a 0.45 micron PVDF filter.

Example 72: Contact Lenses

In another example, the following lenses and materials were each processed through the subsequent examples: Silicone (NuSil, Med 6755); PureVision, balafilcon A; Acuvue Oaysys, senofilcon A; AIR OPTIX, Lotrafilcon B, MJS Lenses, MJS Lens Technology Ltd. All subsequent references to 'lenses', include each of the above lenses and materials.

Example 73: Contact Lenses Dip Coated to Obtain a Bulk Layer of Poly(Ethylene Glycol) (Peg) Hydrogel In another example, commercially available and hydrated lenses were washed in deionized water three times for 30 min each time. The lenses were desiccated in a vacuum chamber for 2-24 hrs.

Lens surfaces were functionalized using nitrogen gas in a standard plasma chamber (Plasma etch PE-50) at settings: 200 mTorr, 3 min, 100 W RF power, 5-20 standard cubic centimeters per minute. Lenses were then used within 1 hour.

The PEG macromers were combined with either deionized water (DI Water), Isopropanol Alcohol (IPA), or Methanol (MeOH) @ 0.2M TEOA to obtain solutions with a total solids concentration of 0.1%, 0.25% and 0.5%. Various concentrations of substrates were used; each solution was at a 10% molar excess of VS (See quantities in table below) and a 0% PEG solution was also prepared as a control.

The volume of substrate detailed below was added to individual vials, followed by the noted volume of PEG-VS. The surface functionalized lenses were added to this solution. The PEG-SH was added and the lenses were placed on a mixing table for 1 hr-24 hrs. The lenses were washed individually in the corresponding substrate for 30 min. For the solvent conditions, consecutive 30 min washes were in 100% IPA, 50% IPA in DI Water, and 100% DI Water. Lenses in the aqueous substrate were only washed in 100% DI water.

The lenses were placed in Phosphate Buffered Saline (PBS) and autoclaved in a wet cycle at 250° F. for 30 min. Lens general comfort and contact angle were determined through wear and direct in-house measurement, respectively.

|  |  | PEG Concentration | | | |
| --- | --- | --- | --- | --- | --- |
|  |  | 0.00% | 0.1% | 0.25% | 0.5% |
| Volume (μL) | PEG-VS | 0.0 | 5.3 | 13.25 | 26.6 |
|  | PEG-SH | 0.0 | 9.7 | 24.25 | 48.4 |
|  | DI H20, IPA, or MeOH @ 0.2M TEOA | 1500 | 1485 | 1462.5 | 1425 |
|  | Total | 1500 | 1500 | 1500 | 1500 |

Example 74: Lenses Dip Coated with Recycled PEG

In another example, the steps of above Example 73 were repeated for contact lenses PureVision, balafilcon A, at a 0.4M concentration of TEOA. The PEG from this process was kept. After 24 hrs, a PEG solution was developed using 50% of the original (750 μL) and 50% fresh or non-previously-used PEG. Example 73 was repeated using this PEG solution.

Example 75: Lenses Surface Activated Using Hydrogen Peroxide and Dip Coated

In another example, dehydrated contact lenses PureVision, balafilcon A, were placed in commercially available Hydrogen Peroxide for 1 hr. The lenses were washed with DI water for 30 min. The coating, washing, autoclave, and testing process was repeated according to Example 73.

Example 76: Lenses Extracted, Desiccated, and Dip Coated

In another example, lenses were placed in 1.5 ml of IPA or MeOH (solvent) and set on a mixing table for 12-18 hrs. The solvent was switched and the lenses were washed in the corresponding solvent for an additional hour. The solvent was replaced with deionized water and the lenses were washed three times for 30 min to 1 hr each time. The lenses were desiccated in a vacuum chamber for 2-24 hrs.

Lens surfaces were functionalized using nitrogen gas in a standard plasma chamber (Plasma etch PE-50) at settings: 200 mTorr, 3 min, 100 W RF power, 5-20 standard cubic centimeters per minute. Lenses were then used within 1 hour. The lenses were coated, washed, autoclaved, and tested according to the aqueous process of Example 73.

Example 77: Lenses Dip Coated and Accelerated Life Tested to Identify the Stability of the Bulk Layer of PEG In another example, the steps of Example 73 were repeated; for contact lenses (PureVision, balafilcon A and MJS Lens Technology Ltd). Post autoclave and testing process, the lenses were placed in PBS and autoclaved once more or placed in sterile saline. The lenses were placed in hybridization ovens (Stovall Life Science Inc) at 20, 40, or 60 degrees Centigrade. The lenses were tested on dates that correspond to six or twelve months of accelerated life testing as detailed by FDA 510K clearance requirements for medical devices generally, and daily wear contacts specifically. Post-testing, the sterile saline was replaced with new sterile saline and the lenses were replaced in the respective hybridization oven.

Example 78: Coating Characterized Via Captive Bubble Contact Angle Testing

In another example, to measure lens contact angles, the captive bubble technique was used. The lens was loaded onto a small plate with a bulbous feature. The lens was submerged in PBS and suspended atop a plate that has a hole through which the convex surface of the lens protrudes downward. A blunt needle was placed just below the surface of the center of the lens. A bubble was then advanced with a syringe pump until it makes contact with the lens, at which point the bubble was retracted until it breaks free from either the lens or the needle. Through a magnifying lens, a high-definition video camera records the entire procedure, after which an image was saved from the frame immediately preceding the moment the bubble detaches from either the lens or the needle. From this image, the angles between the lens and the bubble on both sides of the bubble were calculated in MATLAB and saved as the contact angles for that lens.

Example 79: Lubricity Test Method

A test method was designed and built to observe the affects that the hydrogel coating has on the lubricity of the lens. Three contact lenses were used in this evaluation:
1. Packaged silicone hydrogel lens A
2. Hydrogel coated silicone hydrogel lens A
3. Packaged silicone hydrogel lens B 6 sec A borosilicate glass plate was cleaned and submerged in a tank of PBS. One end of the plate was raised 30 mm with a shim to create a ramp with an angle of ~11 degrees. The test lenses were placed at the top of the ramp and weighted down with a stainless steel bolt, weighting approximately 1.13 grams. The lenses were allowed to slide down the ramp ~152 mm and the time required to reach the bottom of the ramp was recorded. Results:

| Lens Type | Time to Slide (sec) |
|---|---|
| Packaged silicone hydrogel lens A | Lens allowed to slide for X seconds but only slid down X mm |
| Hydrogel coated silicone hydrogel lens A | 2 second |
| Packaged silicone hydrogel lens B 6 sec | 6 seconds |

The results of the tests demonstrate a significant increase in lubricity of the lens coated with hydrogel as compared with the uncoated control.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Example 80

Figure 15A:
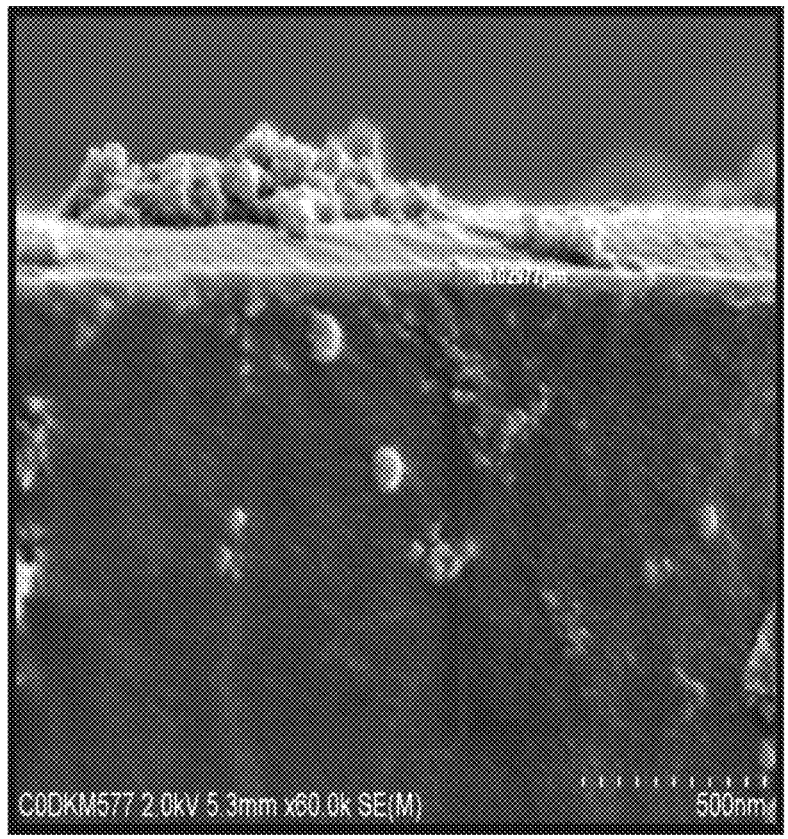
FIGS. 15A-15B show scanning electron microscope images of a polyethylene glycol film formed over a contact lens core.
Figure 15B:
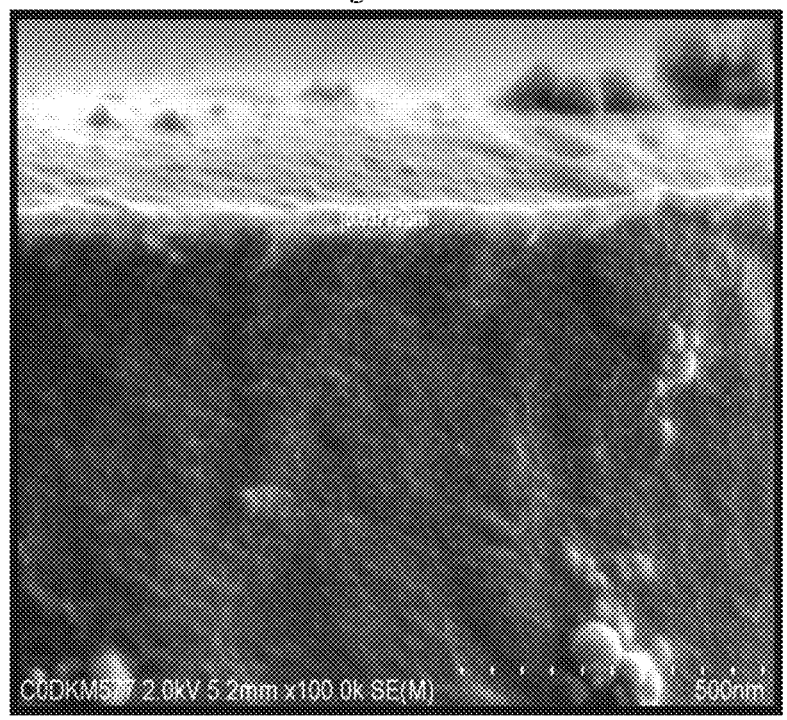
Figure 16:
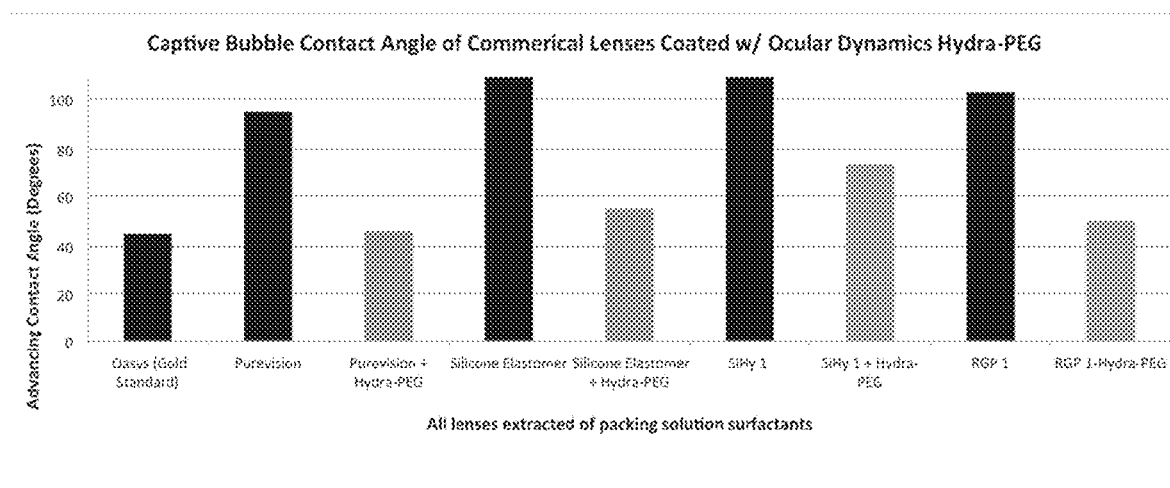
FIG. 16 illustrates contact angles of hydrophilic coatings formed on various commercial contact lenses.

FIGS. 15A and 15B show scanning electron microscope images of PEG layers formed on contact lens cores using the processed described herein. The PEG layer analyzed in FIG. 15A had a measured thickness of 29.77 nm. The PEG layer analyzed in FIG. 15B had a measured thickness of 37.72 nm.

Example 81

Rigid gas permeable contact lenses are processed in accordance with the processes described herein. Commercial RGP lenses are treated with the processes disclosed herein to form hydrophilic coatings on the Bausch & Lomb Boston Lens, Paragon CRT lens, Menicon Rose K, Menicon Lagado Flosi, Menicon Lagado Tyro, Menicon Lagado Onsi, Contamac Optimum Classic, Contamac Optimum Comfort, Contamac Optimum Extra, and Contamac Optimum Extreme.

Example 82

Hybrid RGP lenses are processed in accordance with the processes described herein. Commercial hybrid RGP lenses are treated with the processes disclosed herein to form hydrophilic coatings on the Synergeyes Duette Lens and the Synergeyes Ultra Health.

Example 83

The advancing contact angle was measured for various commercial contact lenses coated with hydrophilic PEG polymer layer as described herein. FIG. 13 shows advancing contact angle data for the commercial contact lenses coated with the PEG coatings disclosed herein. The advancing contact angle was measured for commercial contact lenses before and after coating the lenses with a hydrophilic PEG polymer coating. All of the lenses were treated to extract any packing solution surfactants that were present prior to measuring the advancing contact angle.

The advancing contact angle was measured for an uncoated Oasys lens (Gold Standard), Purevision lens, silicone elastomer lens, silicon hybrid lens, and a rigid gas permeable lens. The advancing contact angle was also measured for a coated Purevision lens, coated silicon elastomer lens, coated silicon hybrid lens, and a coated rigid gas permeable lens.

All solvents used were commercially available and were used without further purification. Starting materials used were either available from commercial sources or prepared according to literature procedures and had experimental data in accordance with those reported.

Example 84: Preparation of Polymer Solutions

The coating solution included two components. The first component was a poly(ethylene glycol) (PEG) molecule end functionalized with vinyl sulfone groups. The second component was a polyacrylamide molecule with pendant amine functional groups. The polymer solutions were prepared at a concentration of 2.5% in deionized water and then filter sterilized through a 0.45 micron PVDF filter.

Example 85: Preparation of Polymer Solutions

The coating solution included two components. The first component was A poly(ethylene glycol) (PEG) molecule end functionalized with succinimidyl ester groups. The second component was a polyacrylamide molecule with pendant amine functional groups. The polymer solutions were prepared at a concentration of 2.5% in deionized water and then filter sterilized through a 0.45 micron PVDF filter.

Example 86: Preparation of Polymer Solutions

The coating solution included two components. The first component was a poly(ethylene glycol) (PEG) molecule end functionalized with vinyl sulfone groups. The second component was a polyacrylamide molecule with pendant thiol functional groups. The polymer solutions were prepared at a concentration of 2.5% in deionized water and then filter sterilized through a 0.45 micron PVDF filter.

Example 87: Contact Lenses

The following lenses and materials were each processed through the subsequent examples: Silicone (NuSil, Med 6755); PureVision, balafilcon A; Acuvue Oaysys, senofilcon A; AIR OPTIX, Lotrafilcon B; Biofinity, Comfilcon A. All subsequent references to 'lenses', include each of the above lenses and materials.

Example 88: Contact Lenses Dip Coated in Aqueous Solution

Commercially available and hydrated lenses were washed in deionized water three times for 30 min each time. The lenses were desiccated in a vacuum chamber for 2-24 hours.

Lens surfaces were functionalized using a reactive ion etch plasma chamber with a 2 minute treatment time. Lenses were then used within 1 hour.

The corresponding PEG and polyacrylamide polymer solutions described in Examples 84, 85, or 86 were combined together followed by adjusting the pH. Polymers were combined such that reactive groups were within 10% of equimolar concentrations. The total solids concentration of the combined polymer solution was adjusted to 0.05% using DI water.

The surface functionalized lenses were added to the combined polymer solutions and then placed on a mixing table for 0.5 hour-24 hours. The lenses were then washed extensively with Phosphate Buffered Saline.

The lenses were placed in Phosphate Buffered Saline (PBS) and autoclaved in a wet cycle at 250° F. for 30 minutes. Lens were then characterized through captive bubble contact angle, protein deposition, and lubricity.

Example 89: Contact Lenses Coated in Autoclave

Commercially available and hydrated lenses were washed in deionized water three times for 30 minutes each time. The lenses were desiccated in a vacuum chamber for 2-24 hours.

Lens surfaces were functionalized using a reactive ion etch plasma chamber with a 2 minute treatment time. Lenses were then used within 1 hour.

The corresponding PEG and polyacrylamide polymer solutions described in Examples 84, 85, or 86 were combined together. Polymers were combined such that reactive groups were within 10% of equimolar concentrations. The total solids concentration of the combined polymer solution was adjusted to 0.05% in saline.

Example 90: Captive Bubble Contact Angle Characterization

To measure lens contact angles, the captive bubble technique was used. The lens was loaded onto a small plate with a bulbous feature. The lens was submerged in PBS and suspended atop a plate that has a hole through which the convex surface of the lens protrudes downward. A blunt needle was placed just below the surface of the center of the lens. A bubble was then advanced with a syringe pump until it made contact with the lens, at which point the bubble was retracted until it broke free from either the lens or the needle. Through a magnifying lens, a high-definition video camera recorded the entire procedure, after which an image was saved from the frame immediately preceding the moment the bubble detached from either the lens or the needle. From this image, the angles between the lens and the bubble on both sides of the bubble were calculated in MATLAB and saved as the contact angles for that lens, as detailed in FIG. 14.

The results from the captive bubble contact angle characterization of the lenses are shown in the table below.

| Lens | Contact Angle |
|---|---|
| Oasys | 35 |
| Coated Oasys | 25 |
| Biofinity | 41 |
| Coated Biofinity | 25 |
| AirOptix | 75 |
| Coated AirOptix | 25 |
| Silicone | 100 |
| Coated Silicone | 25 |

As shown in the table, the applied coatings significantly decreased the contact angle of the lens in comparison to the uncoated lens.

Example 91: Lubricity Characterization

The instrumented scratch testing method included the generation of scratches with a stylus, generally a diamond tip, which was drawn across the sample's surface at a constant speed and a defined normal force (constant or progressively increasing), for a defined distance. Test outputs included the tangential and frictional forces.

By performing the test with a low constant load (to avoid surface damage and deformation) and by using a ball instead of a diamond indenter, it is possible to measure the coefficient of friction between two materials without the creation of wear or damage. In this case, the coefficient of friction was computed by dividing the tangential force by the applied normal force.

Testing was performed using guidance, recommendations and general procedures from ASTM standards (G171, G99, G133, G115, C1624, and D7187), and in accordance with ASTM G171 except for the following: the indenter had a 3 mm radius instead of a 200 micron radius.

A Nano Scratch Tester "NST" from CSM Instruments S/N 01-2767 was used. The software was "Scratch" version 4.48. The following settings were used with the NST: e, Load 100 mN and 200 mN, Scratch Length 1 mm, Speed 2 mm/min, Cantilever HL-125, Static Partner Size Diameter 6 mm, with a Temperature of 21-23° C.

The coefficient of friction for Oasys lenses was 0.036+/−0.009. The coefficient of friction for Oasys lenses was 0.036+/−0.009. The coefficient of friction for coated Oasys lenses was 0.022+/−0.01. The coefficient of friction for coated silicone lenses was 0.055+/−0.003.

Example 92: Protein Resistance Characterization

Various contact lenses listed above (n=4 for each lens type) were soaked in a complex salt solution (CSS) for 18 hours on a shaker to remove any residual blister pack solution. The lenses were then rinsed twice in CSS and blotted on lens paper. Each lens was placed in a vial containing 1 mL of an artificial tear solution (ATS) containing 125I-labeled lysozyme. The vials were capped, sealed with Parafilm, and incubated at 37° C. with shaking for 3 and 7 days.

At the end of the incubation period, each lens was rinsed twice in CSS and blotted on a lens paper. Lenses were then placed in sterile 5 ml (12×75 mm), non-pyrogenic, polypropylene round bottom tubes and radioactive counts were subsequently determined using a Gamma Counter (Perkin Elmer Wallac Wizard 1470 Automatic Gamma Counter, Wellesley, MA, USA). As shown in the table below the coated PureVision lens had a higher protein resistance than the uncoated PureVision lens as indicated by the lower amount of protein present on the lens surface.

| Lens type | Day 3 μg/Lens | Day 7 μg/Lens | Day 3 SD | Day 7 SD |
|---|---|---|---|---|
| PureVision | 25.6970838 | 30.51769217 | 3.003109704 | 4.170355071 |
| Coated PureVision | 12.59044545 | 16.28985614 | 2.039246577 | 1.249256932 |

Example 93: Water Break-Up Time Characterization

Lenses were washed extensively in saline to remove packaging solution. Lenses were then held at the edge using rubber tipped tweezers, dipped into a vial containing phosphate buffered saline, and then pulled out rapidly. The time until the water film began to break and contract across the surface was measured and called the water break-up time. As shown in the table below the coated lenses had a longer water break-up time than the uncoated counterparts. For example, the coated lenses all had water break-up times of greater than 25 seconds.

| Lens | Water Break-up Time (s) |
|---|---|
| Oasys | 10 |
| Coated Oasys | >25 |
| Biofinity | 7.5 |
| Coated Biofinity | >25 |
| AirOptix | 5 |
| Coated AirOptix | >25 |
| Silicone | 0 |
| Coated Silicone | >25 |

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of making a hydrogel coated contact lens comprising:
    reacting an outer surface of a lens core of a contact lens with a hydrophilic polymer population comprising a first polyacrylamide species and a second polyacrylamide species, wherein the first polyacrylamide species comprises a reactive amine moiety at a first portion that forms a covalent attachment to the outer surface of the contact lens; and
    reacting the first polyacrylamide species with the second polyacrylamide species, wherein the second polyacrylamide species comprises a reactive carboxyl moiety that forms a covalent bond to a second portion of the first polyacrylamide species in a second covalent reaction, thereby forming a hydrogel coating on the lens core, wherein the first polyacrylamide species is at least partially cross-linked to the second polyacrylamide species.

2. The method of claim 1, wherein the covalent attachment between the outer surface of the contact lens and the first portion of the first polyacrylamide species is formed by a first nucleophilic conjugate reaction.

3. The method of claim 1, wherein the second covalent reaction is a second nucleophilic conjugate reaction.

4. The method of claim 1, wherein the lens core is a soft contact lens.

5. The method of claim 4, further comprising modifying the outer surface of the contact lens to form a plurality of reactive nucleophilic sites or a plurality of electrophilic sites on the outer surface.

6. The method of claim 5, wherein the plurality of reactive nucleophilic sites or the plurality of electrophilic sites are selected from the group consisting of: hydroxyl, carboxyl, N-hydroxysuccinimide (NHS) ester, sulfo-NHS ester, imidoester, isocyanate, isothiocyanate, acylhalide, arylazide, p-nitrophenyl ester, aldehyde, and sulfonyl chloride.

7. The method of claim 5, wherein the modifying step comprises exposing the outer surface of the contact lens to a gas plasma treatment.

8. The method of claim 1, further comprising adding a bifunctional monomer or a polymer to a prepolymerization mixture used to form the contact lens.

9. The method of claim 8, wherein the bifunctional monomer or the polymer provides additional nucleophilic or electrophilic reactive sites on the outer surface of the contact lens.

10. The method of claim 9, wherein adding the bifunctional monomer or the polymer to the prepolymerization mixture includes one or more of: pH adjustment, plasma activation, light activation, activation of the prepolymerization mixture, wet activation, and adding a monomer that reacts with the contact lens that still leaves reactive sites.

11. The method of claim 1, wherein the lens core comprises polysiloxane.

12. The method of claim 1, wherein the lens core is substantially free of polysiloxane.

13. The method of claim 1, wherein the lens core is a hydrogel core.

14. The method of claim 1, wherein the hydrogel coated contact lens has an oxygen transmissibility (DK/t) of greater than 200.

15. The method of claim 1, wherein the hydrogel coating comprises a thickness between about 1 nm to about 50 nm.

16. The method of claim 1, wherein the lens core comprises an elastic modulus of less than about 1.8 MPa.

17. The method of claim 1, wherein the lens core comprises an equilibrium water content of less than about 1%.

18. The method of claim 1, wherein the lens core comprises an equilibrium water content of less than about 0.5%.

19. The method of claim 1, wherein the lens core comprises an oxygen transmissibility (Dk/t) of greater than about 200.

20. The method of claim 1, wherein the lens core comprises about 50% to about 100% silicone by weight.

* * * * *